US006265423B1

(12) United States Patent
Leblond et al.

(10) Patent No.: US 6,265,423 B1
(45) Date of Patent: Jul. 24, 2001

(54) AROMATIC POLYCYCLIC RETINOID-TYPE DERIVATIVES, METHOD FOR PREPARING SAME, AND USE THEREOF FOR MAKING PHARMACEUTICAL AND COSMETIC COMPOSITIONS

(75) Inventors: Bertrand Leblond, Rouen (FR); Francis Darro, Brussels (BE); Abdallah Devine, Rouen (FR); Véronique Sales-Sallans, Le-Mesnil-Esnard (FR); Pierre Duhamel, Mont-Saint-Aignan (FR); Robert Kiss, Wauthier Braine (BE); Alain-René Schoofs, Courbevoie (FR); Pierre Germain, Saint-Yrieix-la-Perche (FR); Bernard Pourrias, Bievres (FR)

(73) Assignee: Centre Europeen de Bioprospective-Ceb (FR)

( * ) Notice: Subject to any disclaimer, the term of this patent is extended or adjusted under 35 U.S.C. 154(b) by 0 days.

(21) Appl. No.: 09/119,066

(22) Filed: Jul. 15, 1998

Related U.S. Application Data

(63) Continuation of application No. PCT/FR97/00079, filed on Jan. 16, 1997.

(30) Foreign Application Priority Data

Jan. 17, 1996 (FR) .................................. 96 00497

(51) Int. Cl.$^7$ ............................. A61K 31/44; A61P 35/00; A61P 37/00; C07C 63/06; C07D 211/86
(52) U.S. Cl. ........................ 514/354; 514/378; 514/381; 514/438; 514/456; 514/784; 546/322; 548/248; 548/250; 549/71; 549/399; 549/402; 562/490
(58) Field of Search ..................... 514/764, 765, 514/784, 381; 585/25, 26, 435, 436; 562/490; 548/250

(56) References Cited

U.S. PATENT DOCUMENTS

| | | | |
|---|---|---|---|
| 4,326,055 | * | 4/1982 | Loeliger ................................ 542/429 |
| 4,719,238 | * | 1/1988 | Bollag .................................. 514/765 |
| 4,863,969 | * | 9/1989 | Bollag .................................. 514/765 |
| 4,870,219 | * | 9/1989 | Klaus et al. ......................... 570/189 |
| 5,055,622 | * | 10/1991 | Klaus et al. ......................... 568/609 |

FOREIGN PATENT DOCUMENTS

| | | |
|---|---|---|
| 37 15 955 A1 | 11/1987 | (DE) . |
| 0 0002 742 A1 | 7/1979 | (EP) . |

* cited by examiner

Primary Examiner—Jane C. Oswecki
(74) Attorney, Agent, or Firm—Schnader Harrison Segal & Lewis LLP

(57) ABSTRACT

Novel aromatic polycyclic retinoid-type derivatives of general formula (I),

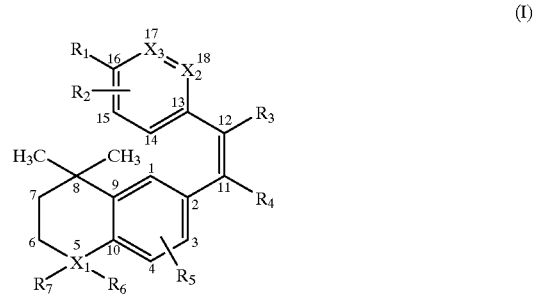

wherein groupings $R_3$ and $R_4$ attached to the double bond between carbons 11 and 12 are cis groupings, and pharmaceutical and cosmetic compositions containing same, are disclosed.

17 Claims, 4 Drawing Sheets

AROMATIC POLYCYCLIC RETINOID-TYPE DERIVATIVES, METHOD FOR PREPARING SAME, AND USE THEREOF FOR MAKING PHARMACEUTICAL AND COSMETIC COMPOSITIONS

This application is a continuation of PCT/FR97/00079, filed Jan. 16, 1997.

This invention relates to aromatic polycyclic derivatives of the retinoid type of general formula:

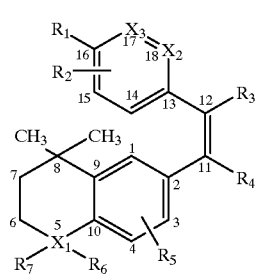

(I)

in which the groups $R_3$ and $R_4$ carried by the double bond between the 11 and 12 carbon are in a cis arrangement and $R_1, R_2, R_3, R_4, R_5, R_6, R_7, X_1, X_2$ and $X_3$ have the following meanings:

$R_1$ represents a hydrogen atom, a lower alkyl group, or a group of formula —$CH_2OH$, —OH, —CHO— —COOH, —$COR_8$, —$CH_2OCOR_9$, —SH, —S-alkyl, —$PO_3H_2$, p-hydroxyphenylaminocarbonyl, tetrazol-5-ylaminocarbonyl, tetrazol-5-yl, 5-trifluoromethyl-tetrazoyl, and when it is possible their salts with physiologically tolerated acids, where $R_8$ and $R_9$ are:

a hydrogen atom, an —OH group, a lower alkyl group, or a group of formula —$OR_{10}$, where $R_{10}$ represents an alkyl group, which may be branched or not, having from 1 to 20 carbon atoms, an alkenyl group which may be branched or not, having from 2 to 20 carbon atoms, an aryl or aralkyl group, or an amine group of formula:

in which r and r', identical or different, represent a hydrogen atom, a lower alkyl group, an aryl or aralkyl group, an α-aminoacid group, a sugar group or a heterocyclic group in which r and r' taken together form a heterocyclic ring.

$R_2$ represents a hydrogen atom, a halogen atom and more particularly a fluorine atom, a lower alkyl group, a group of formula —COOH, $OR_{11}$, —$SR_{11}$, —$(CF_2)_nCF_3$ where n is a whole number between 0 and 10, or a $OCOR_{11}$ group, and when this is possible their salts with physiologically tolerated acids, or an amine group of formula:

in which r and r' have the same meaning as previously, and $R_{11}$ represents a hydrogen atom, a lower alkyl group, a fluoroalkyl group having 1 to 6 carbon atoms and from 3 to 7 fluorine atoms, an aryl group or an aralkyl group.

$R_3$ represents a hydrogen atom, a trifluoromethyl group, an aryl group, an aralkyl group or a lower alkyl group, possibly substituted with a hydroxyl group or with one or more atoms of fluorine, with a lower alkoxy group or with a group of formula —(C═O)$R_{12}$, in which $R_{12}$ represents a hydrogen atom, a lower alkyl group, a hydroxyl group, a lower alkoxy group, or an amine group of formula:

in which r and r' have the same meaning as previously, $R_4$ represents a hydrogen atom or an aryl group, $R_5$ represents a hydrogen atom, a lower alkyl group, a halogen atom, a fluoroalkyl group having 1 to 6 carbon atoms and from 3 to 7 atoms of fluorine, or a group of formula —$OR_{13}$ where $R_{13}$ represents a hydrogen atom, a lower alkyl group, an aryl group or an aralkyl group or a trifluoromethyl group, $X_1$ is chosen from among an atom of carbon, an atom of oxygen or an atom of sulphur, and $R_6$ and $R_7$ are:

methyl or ethyl groups, in the case where $X_1$ is an atom of carbon, nothing in the case where $X_1$ is an atom of oxygen or an atom of sulphur, one or two atoms of oxygen in the case where $X_1$ is an atom of sulphur (the case of a sulphoxide —SO— or a sulphone —$SO_2$—).

$X_2$ and $X_3$, identical or different, represent an atom of carbon, an atom of oxygen or an atom of nitrogen, or $X_2$-$X_3$ may be a single atom of sulphur, oxygen or nitrogen so the nucleus carrying $X_2$ and $X_3$ can be a benzene, pyridine, thiophene, furane, pyrrole nucleus or in the case where $X_2$ is an atom of oxygen and $X_3$ an atom of carbon, $C_{13}$ and $C_{14}$ represent a single, one and the same carbon atom, and then the nucleus carrying $X_2$ and $X_3$ can be an iso-oxazole nucleus.

As examples of pharmaceutically acceptable salts of the previous derivatives, one may mention, in a non-limitative way: the salts of acetic, hydrochloric, cinnamic, citric, formic, hydrobromic, hydriodic, hydrofluoric, malonic, methanesulphonic, oxalic, picric, maleic, lactic, nicotinic, phenylacetic, phosphoric, succinic, sulphuric and tartaric acids, ammonium salts, and salts of piperazine, diethylamine, nicotinamide, urea, sodium, potassium, calcium, magnesium, zinc, lithium, methylamine, dimethylamine, trimethylamine and tris(hydroxymethyl) aminomethane.

The term lower alkyl or alkoxy groups designates groups with 1 to 6 carbon atoms, straight chained or branched such as methyl, ethyl, propyl, isopropyl, butyl, isobutyl, secondary butyl, methoxy, ethoxy, propoxy, isopropoxy, butyloxy, isobutyloxy and secondary butyloxy groups.

Totally trans retinoic acid, a metabolite of vitamin A exhibits a large number of biological properties. Several molecules constructed from chemical modifications of this acid have been synthesised and have been shown to be biologically active. These synthetic analogues and their derivatives are called retinoids according to the definition of Sporn M. B. and Roberts A. B., Found Symp., 113, 1–5, 1985. Among these compounds, one may mention those described in European Patent Applications published under numbers 350 846, 303 186, 253 302, in the PCT International Patent Application published under the number WO 93/11755, or in American Patents U.S. Pat. Nos. 5,300,522, 5,420,273, 4,578,498 and the German Patents 3602473 and 3715955 as well as in the articles by Marcia I. Dawson et al. (J. Med. Chem., 1989, 32, 1504–1517; J. Med. Chem. 1993, 36, 2605–2613).

The compounds of the retinoid type that show activity are used in the treatment of mammals and more particularly humans as chemoprevention and chemotherapy, notably in the treatment of numerous diseases such as dermatosis, acne, Darier's disease, psoriasis, icthyosis and eczema. These compounds are also used for the treatment and the prevention of cancerous diseases and numerous malignant hyperproliferative diseases such as cancers of the breast, the prostate, the lung, the head and the neck as well as certain types of cancer of epithelial origin and myelocytary leukaemias. The compounds of the retinoid type that show activity are also used for the treatment and the prevention of arteriosclerosis, restenosis stemming from neo-intimal hyperproliferation, benign hyperproliferative pathologies such as endometrial hyperplasis, benign hypertrophy of the prostate, proliferative retinopathy, for the treatment of autoimmune diseases and immunological disorders such as erythematic lupus, for the treatment and the prevention of diseases associated with the metabolism of lipids and for the treatment of the effects of the sun on the skin.

However, these compounds of the retinoid type exhibit important secondary effects, notably a strong irritation of the skin and of the mucous membranes, lipidic toxicity, and are even teratogens, which makes their clinical use delicate (Kistler, A. et al. Arch Toxicol., 64: 616–622; "Retinoids in Oncology", edited by Waun Ki Hong & Reuben Lotan, The University of Texas M. F. Anderson Cancer Center, Houston, Tex., USA, Marcel Dekker Inc., pages 127–146; "Retinoids in Clinical Practice", edited by Gideon Koren The Motherisk Program, The Hospital for Sick Children and The University of Toronto, Toronto, Ontario, Canada, Marcel Dekker Inc.).

The harmful effects reported above have led the applicant to look for aromatic polycyclic derivatives of the retinoid type which are active in the treatment and prevention of the preceding diseases but do not show any secondary effects.

In a surprising way, the applicant has provided evidence that the compounds of Formula I in which the groups $R_3$ and $R_4$ of the double bond between carbons 11 and 12 are in cis configuration, show activity greater than that of the corresponding trans isomers or a mixture of cis/trans isomers, and may not show the secondary effects notably teratogenic effects generally associated with the use of compounds of the retinoid type. The prior art and notably the patents and patent applications mentioned above indicate logically the existence of cis and trans isomers because of the double bond between carbon atoms 11 and 12, but concern themselves specifically with compounds with a trans configuration since this configuration is that met with in the reference arotinoid: the acid (E) 4-[2I(5,6,7,8-tetrahydro-5,5,8,8-tetramethyl-naphthalenyl)-1-propenyl]benzoic acid (TTNPB).

Always conforming to the structure of TTNPB, these compounds of the prior art are characterised by the presence of a substituent group, more particularly a methyl group on carbon 11 ($R_4$=—$CH_3$ in Formula 7), while the compounds of the invention have, on the contrary, a substituent group, notably an alkyl group on carbon atom 12 and not on carbon atom 11.

The research work carried out by the applicant on the derivatives of general Formula (I) in which the groups $R_3$ and $R_4$ are in cis configuration, have led her to demonstrate that these compounds show an intrinsic activity that allows them to modulate proliferation and cellular differentiation, and that this permits their application in the treatment and the chemoprevention of diseases such as breast cancer, prostate cancer, lung cancer, cutaneous cancers and promyelocytary leukaemias in non-teratogenic compositions.

Hence, the objectives of this invention are aromatic polycyclic aromatic retinoid derivatives of general Formula (I), previously defined, their method of preparation as well as their use in human and veterinary medicine and in cosmetics.

Among the derivatives of Formula (I), a preferred series is that in which $R_3$ represents a lower alkyl group or a trifluoromethyl group or a —$(CH_2)_n CF_3$ group where n is a whole number between 0 and 10, and $R_4$ represents a hydrogen atom.

Another preferred series of derivatives of Formula (I) according to the invention are those in which $R_2$ represents a hydrogen atom and $R_1$ represents a tetrazoyl group or a —COOH group. Among these compounds, the series of derivatives for which $R_1$ and $R_2$ are other than a —COOH group, exhibit particularly interesting properties; such derivatives are, for example, the compounds designated CB92834, CB77402, CB61692, CB63237 and CB39122 below. These compounds may therefore be clearly distinguished from prior art compounds of the retinoid type that stem from TTNPB and which carry a —COOH group on carbon atom 16.

The invention considers as a specific example the following derivatives of Formula (I):

The acid (Z), 2-[1-(5,6,7,8-tetrahydro-5,5,8,8-tetramethyl-2-naphthalenyl)-2-propenyl]pyridinyl-5-carboxylic acid, designated CB38416 and corresponding to the following formula:

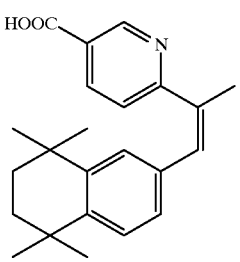

The acid (E) 4-[1-trifluoromethyl-2-(5,6,7,8-tetrahydro-5,5,8,8-tetramethyl-2-naphthalenyl)-1-ethenyl]benzoic acid, designated CB36493 and corresponding to the following formula:

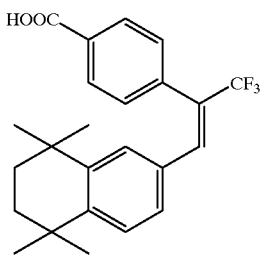

The acid (Z) 4-[1-(5,6,7,8-tetrahydro-3,5,5,8,8-pentamethyl-2-naphthalenyl)-2-propenyl]benzoic acid, designated CB32706 and corresponding to the following formula:

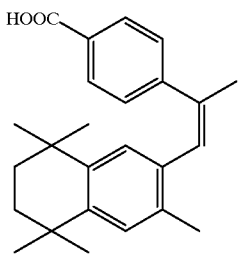

The acid (E) 4-[1-trifluoromethyl-2-(5,6,7,8-tetrahydro-3,5,5,8,8-pentamethyl-2-naphthalenyl)-1-ethenyl]benzoic acid, designated CB62899 and corresponding to the following formula:

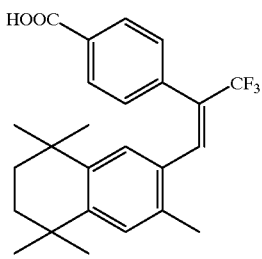

The acid (Z) 4-[1-(3',4'-dihydro-4',4'-dimethyl-1',1'-dioxide-2'H-1'-benzothiopyran-6'-yl)-2-propenyl)benzoic acid, designated CB72484 and corresponding to the following formula:

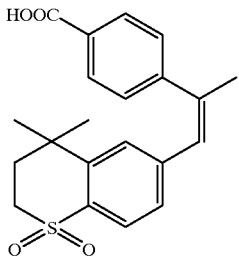

The compound (Z) 5-[4-[1-(5,6,7,8-tetrahydro-5,5,8,8-tetramethyl-2-naphthalenyl)-2-propenyl]phenyl]-1H-tetrazole, designated CB92834 and corresponding to the following formula:

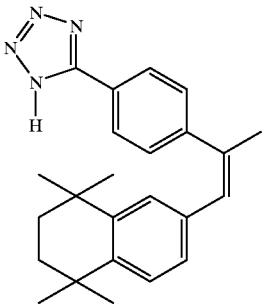

The acid (E) 5-[4-[1-trifluoromethyl-2-(5,6,7,8-tetrahydro-5,5,8,8-tetramethyl-2-naphthalenyl)-1-ethenyl]phenyl]-1H-tetrazole, designated CB77402 and corresponding to the following formula:

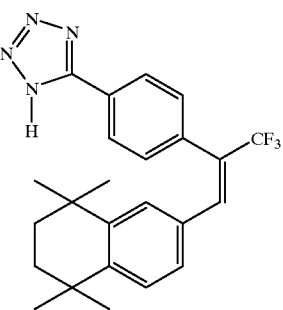

The compound (Z) 5-[4-[1-(5,6,7,8-tetrahydro-3,5,5,8,8-pentamethyl-2-naphthalenyl)-2-propenyl]phenyl]-1H-tetrazole, designated CB61692 and corresponding to the following formula:

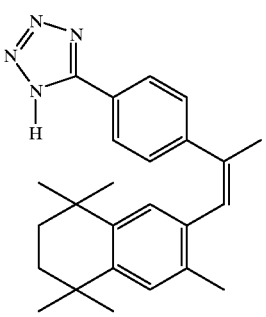

The acid (E) 5-[4-[1-trifluoromethyl-2-(5,6,7,8-tetrahydro-3,5,5,8,8-pentamethyl-2-naphthalenyl)-1-ethenyl]phenyl]-1H-tetrazole, designated CB63237 and corresponding to the following formula:

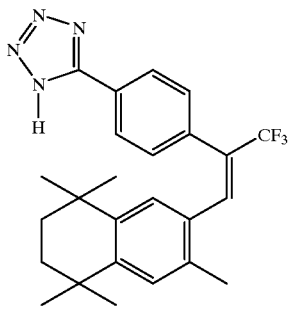

The compound (Z) 5-[4-[1-(3',4'-dihydro-4',4'-dimethyl-1',1'-dioxide-2'H-1'-benzothiopyran-6'-yl)-2-propenyl]phenyl]-1H-tetrazole, designated CB39122 and corresponding to the following formula:

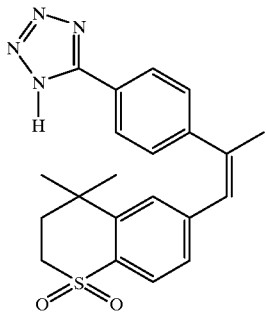

The acid (Z) 2-[1-(5,6,7,8-tetrahydro-5,5,8,8-tetramethyl-2-naphthalenyl)-2-propenyl]thienyl-5-carboxylic acid, designated CB30382 and corresponding to the following formula:

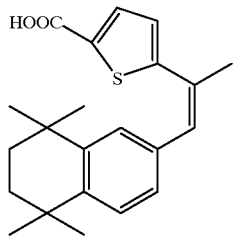

The compound (Z) 5-[2-[1-(5,6,7,8-tetrahydro-5,5,8,8-tetramethyl-2-naphthalenyl)-2-propenyl)]5-thienyl-1H-tetrazole, designated CB92855 and corresponding to the following formula:

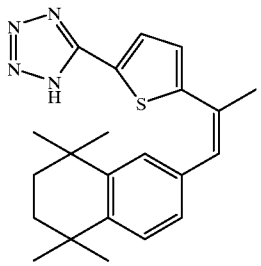

The acid (Z) 5-[1-(5,6,7,8-tetrahydro-5,5,8,8-tetramethyl-2-naphthalenyl)-2-propenyl]pyridinyl-2-carboxylic acid, designated CB16279 and corresponding to the following formula:

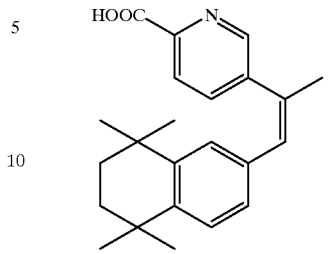

The acid (Z) 2-[1-(5,6,7,8-tetrahydro-3,5,5,8,8-pentamethyl-2-naphthalenyl)-2-propenyl]pyridinyl-5-carboxylic acid, designated CB90525 and corresponding to the following formula:

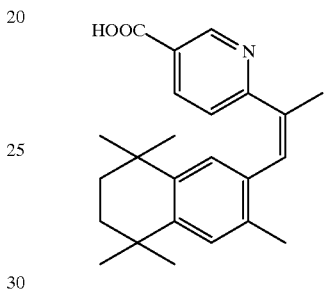

The acid (Z) 5-[1-(5,6,7,8-tetrahydro-3,5,5,8,8-pentamethyl-2-naphthalenyl)-2-propenyl]pyridinyl-2-carboxylic acid, designated CB56004 and corresponding to the following formula:

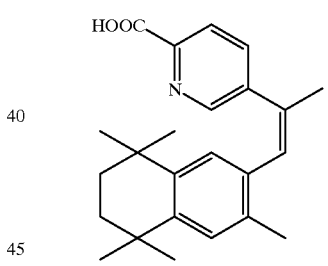

The acid (Z) 5-[1-(5,6,7,8-tetrahydro-5,5,8,8-tetramethyl-2-naphthalenyl)-2-propenyl]isoxazole-3-carboxylic acid, designated CB73069 and corresponding to the following formula:

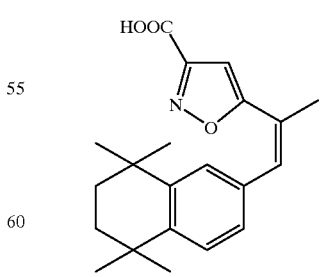

The acid (Z) 5-[1-(5,6,7,8-tetrahydro-3,5,5,8,8-pentamethyl-2-naphthalenyl)-2-propenyl]isoxazole-3-carboxylic acid, designated CB54647 and corresponding to the following formula:

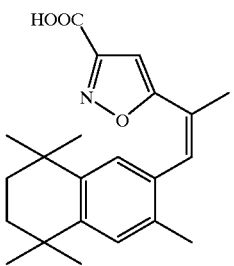

The compound (Z) 1-[4-[1-(5,6,7,8-tetrahydro-5,5,8,8-tetramethyl-2-naphthalenyl)-2-propenyl]phenyl]-5-trifluoromethyl-1H-tetrazole, designated CB29830 and corresponding to the following formula:

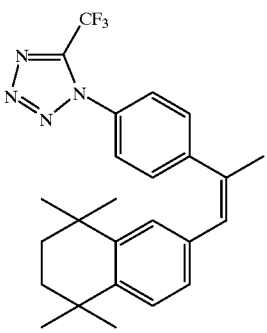

The invention also relates to the preparation of the derivatives of Formula (I) and the use of them for the treatment and the prevention of cancers of the solid tumour type, such as cancers of the breast, lungs, prostate or liver, as well as for the treatment and the prevention of diseases of the skin, such as psoriasis and acne. The invention also relates to pharmaceutical or cosmetic compositions containing as a principle active ingredient at least one derivative of Formula (I).

The derivatives of Formula (I) and their trans configuration isomers can be obtained according to the known Wittig method by condensing a compound of formula:

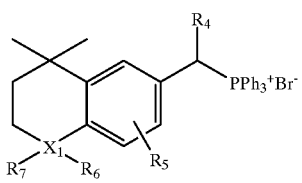

with a compound of formula:

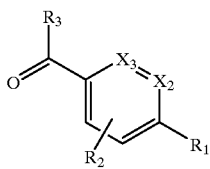

in which $R_1$, $R_2$, $R_3$, $R_4$, $R_5$, $R_6$, $R_7$, $X_1$, $X_2$ and $X_3$ have the same meaning as in Formula (I).

The derivatives of Formula (I) can be prepared by any other method known to those skilled in the art, such as, dehydration of an alcohol corresponding to one or another of the following formulae:

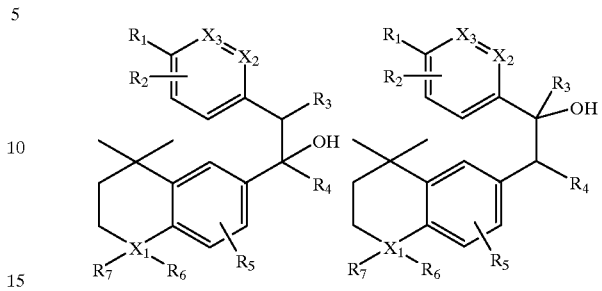

in which $R_1$, $R_2$, $R_3$, $R_4$, $R_5$, $R_6$, $R_7$, $X_1$, $X_2$ and $X_3$ have the same meaning as in Formula (I).

One may also consider a method of the Horner-Emmons, type consisting of condensing a carbonyl compound (aldehyde or ketone) of formula:

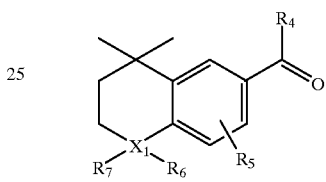

with a phosphonate of formula:

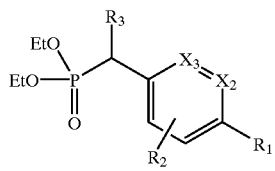

in which $R_1$, $R_2$, $R_3$, $R_4$, $R_5$, $R_6$, $R_7$, $X_1$, $X_2$ and $X_3$ have the same meaning as in Formula (I).

The cis and trans isomeric forms of the derivatives obtained by these various methods can be separated and purified either during the synthesis process by a change of solvent or addition of salt (March, J., Modern Organic Synthesis, 3rd Edition, Wiley Interscience, p. 845–854), or in the final stage, according to known techniques, such as, for example, recrystallisation, preparative HPLC or chromatography.

In addition, it is possible, from derivatives of Formula (I) and from their trans isomers obtained according to previous methods, to prepare other derivatives by usual reactions involving one or more of the groups $R_1$, $R_2$, $R_3$, $R_4$, $R_5$, $R_6$, $R_7$, $X_1$, $X_2$ and $X_3$. For example, one may mention the following reactions.

An ester of a carboxylic acid of Formula (I) in which $R_1$ is a —$COOR_{10}$ group can be saponified by known methods, for example, by treatment with alkaline solutions, more particularly by treatment with a hydro-alcoholic solution of sodium or potassium hydroxide at temperatures between ambient and the boiling point of the reaction mixture. The carboxylic acid thereby obtained can be converted into an amide directly by using ai peptide coupling reaction, for example, by using as ai coupling agent carbonyl di-imidazole (CDI) and as amine the 5-aminotetrazole (Paul R., Anderson G. W., J. Am. Chem. Soc., 82, 4596, 1960).

A carboxylic acid of Formula (I) in which $R_1$ is a —COOH group, can be converted by a known method, for example by treatment with thionyl chloride, in toluene or pyridine, or by phosphorus trichloride or phosphorus pentachloride in toluene, into an acid chloride. This acid chloride can be converted, into an ester by reaction with an alcohol, or into a corresponding amide by reaction with an amine.

A carboxylic acid or a carboxylic acid ester of Formula (I) in which $R_1$ is a —COOH or —COOR$_{10}$ group, can be reduced by known methods in such a way as to give the corresponding alcohol where $R_1$ is a CH$_2$OH group.

A sulphide of Formula (I), or its trans isomer, in which $X_1$ is an atom of sulphur (—S—), can be oxidised to a sulphoxide (—SO—) or a sulphone (—SO$_2$—), $R_6$ and $R_7$ are then identical or different and represent either nothing (the case of a sulphide: —S—), or an oxygen (the case of a sulphoxide: —SO—) or two oxygens (the case of a sulphone —SO$_2$—). The oxidation of a sulphide group can be carried out by using oxidising agents such as periodates (for example sodium periodate) or by using organic peracids such as m-chloroperbenzoic acid (mCPBA). When the oxidation is carried out by using an organic peracid, about 1 equivalent allows one to obtain a sulphoxide while the use of 2 equivalents of peracid leads to the sulphone.

An amide of Formula (I) in which $R_1$ is a —CONrr', can be reduced by known methods in a way that gives an aldehyde ($R_1$=—CHO), for example by di-isobutyl aluminium hydride in solution in toluene, preferably by using THF as reaction solvent at temperatures between −78° C. and ambient.

An aldehyde of Formula (I) in which $R_1$ is a —CHO group, can be oxidised by known methods in a way that gives a carboxylic acid ($R_1$=—COOH) or a carboxylic acid ester ($R_1$=—COOR$_{10}$), for example by the Corey method (Corey E. J. et al., J. Am. Chem. Soc., 90, 5616, 1968) making use of manganese dioxide, sodium cyanide, acetic acid and methanol at ambient temperature.

A nitrile derivative of Formula (I) in which $R_1$ is a —CN group, can be hydrolysed to the corresponding carboxylic acid ($R_1$=—COOH) by known methods, for example, by treatment with alkaline bases, more especially by treatment with a hydro-alcoholic solution of sodium or potassium hydroxide at temperatures between ambient and the boiling point of the reaction mixture.

A nitrile derivative of Formula (I) in which $R_1$ is a —CN group, can be converted into a 1H-tetrazole by known methods, for example by treatment with trimethylsilane azide N$_3$SiMe$_3$, in the presence of not of a catalyst such as dibutyl tin oxide (Bu)$_2$SnO in aromatic solvents preferably toluene or benzene at temperatures between ambient and the boiling point of the reaction mixture.

A brominated, iodated or chlorinated aromatic derivative of Formula (I) in which $R_1$ is an atom of bromine, iodine or chlorine, can be converted by known methods into a nitrile derivative ($R_1$=—CN), for example by the Rosenmund-von Braun reaction using cuprous cyanide in a solvent, preferably dimethyl formamide or quinoline at temperatures between ambient and the boiling point of the reaction mixture.

A brominated, iodated or chlorinated aromatic derivative of Formula (I) in which $R_1$ is an atom of bromine, iodine or chlorine, can be converted by known methods into a carboxylic acid ($R_1$=—COOH), for example by halogen-metal exchange using butyl lithium (primary, secondary or tertiary) in solution in THF with cooling (−78° C. to 0° C.) and condensation of carbon dioxide then being raised again to ambient temperature.

A brominated, iodated or chlorinated aromatic derivative of Formula (I) in which $R_1$ is an atom of bromine, iodine or chlorine, can be converted by known methods into a carboxylic acid ester ($R_1$=—COOR), for example by halogen-metal exchange using butyl lithium (primary, secondary or tertiary) in solution in THF with cooling (−78° C. to 0° C.) and condensation onto an alkyl chloroformate.

The derivatives of Formula (I) in which $R_1$ is a —COOH or -tetrazoyl group, can be converted by known methods into salts by physiologically acceptable, non-toxic, inorganic or organic bases, for example into alkali metal salts or into alkaline earth metal salts, for example sodium, potassium, magnesium or calcium salts as well as ammonium salts or non-toxic amine salts.

A carboxylic acid of Formula (I) in which $R_1$ is a —COOH group can be converted by a known method, for example, by a Curtius type rearrangement, with diphenyl phosphorane azide in the presence of triethylamine in toluene at 80° C., followed by an addition of an alcohol of the ROH type, preferably methyl alcohol (R=Me) or benzyl alcohol (R=benzyl), into carbamate —NHCOOR, which by treatment with 10% aqueous caustic soda (R=Me) or by hydrogenation (R=benzyl) leads to an aniline of Formula (I) where $R_1$ is a —NH$_2$ group.

An aniline of Formula (I) where $R_1$ is a —NH$_2$ group can be converted by known methods of trifluoroacetylation, for example by using 2-(trifluoroacetyloxy)pyridine (TFAP) in ether at temperatures between 0° C. and the boiling point of the reaction mixture (T. Keumi et al., Bull. Chem. Soc. Jpn., 63, 2252, 1990), into the trifluoromethylated amide of Formula (I) where $R_1$ is a —NH(C=O)CF$_3$ group. The trifluoromethylated amide of Formula (I) can be converted by known methods into a chlorinated imine, preferably by using triphenylphosphine and carbon tetrachloride (K. Tamura et al., J. Org. Chem., 58, 32, 1993), to lead to the compound of Formula (I) where $R_1$ is a —N=C(CF$_3$)(Cl) group.

A trifluoroacetimidoyl chloride of Formula (I) where $R_1$ is a —N=C(CF$_3$)(Cl) group can be cyclised by known methods, preferably by sodium azide in acetic acid at 70° C. (D. Armour et al., Bioorg. & Med. Chem. Lett., 6, 1015, 1996) to lead to a tetrazole of formula (I) where $R_1$ is a group with the following formula:

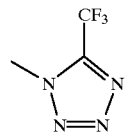

A halogenated compound of Formula (I) where $R_1$ is a bromine, chlorine or iodine atom can be converted by an Arbuzov reaction, preferably by treatment with diethyl phosphite in toluene at the boiling point of the reaction mixture, into a diethyl phosphonate of Formula (I) where $R_1$ is a —P(O) (OEt)$_2$.

A phosphonate of Formula (I) where $R_1$ is a —P(O)(OEt)$_2$ can be hydrolysed by known methods, for example in the presence of trimethylsilyl iodide, to lead to a phosphonic acid of Formula (I) where $R_1$ is a —PO$_3$H$_2$ group.

The Formula (I) derivatives exhibit very interesting properties on differentiation and cellular proliferation, that permit one to envisage their use for therapeutic dermatological and cosmetic purposes. Among therapeutic uses, one may mention the treatment and the prevention of cancers of the solid tumour type such as cancers of the breast, the lungs, the prostate and the liver as well as the treatment and the prevention of skin diseases, such as psoriasis and acne.

In addition, molecular biology work reported below, has permitted definition of activity profiles of the compounds of the invention on retinoic receptors and certain transcriptional factors.

It has recently been suggested that RXR agonist compounds be used in the treatment of non-insulin dependent diabetes and inflammatory and immunitary diseases. As a consequence, the compounds of the invention are useful in the treatment of non-insulin dependent diabetes and inflammatory and immunitary diseases.

Hence, the invention also relates to the use of Formula (I) derivatives for the manufacture of pharmaceutical compositions useful in the treatment or the prevention of cancers as well as for the treatment of non-insulin dependent diabetes and inflammatory and immunitary diseases. They can also be used for the manufacture of cosmetic compositions useful in the treatment or the prevention of diseases of the skin.

As a medicine, the derivatives of the invention are administered in the form of a pharmaceutical composition comprising at least said derivatives, in free form or in the form of a pharmaceutically acceptable salt, in association with a traditional vehicle or diluent. Such compositions, which also form part of the invention, can be presented in a form for administration by an enteral route, for example in the form of tablets, or for administration by a parenteral route, for example in the form of solutions and suspensions that can be injected by an intravenous or muscular route or for administration in the form of a nasal spray.

As a cosmetic, the derivatives of the invention are administered in the form of a cosmetic composition comprising at least said derivatives, in free form or in the form of a pharmaceutically acceptable salt, in association with a traditional vehicle or diluent. Such compositions, which also form part of the invention, can be presented for administration by an enteral route, for example in the form of tablets, or for administration by a parenteral route, for example in the form of solutions and suspensions that can be injected by an intravenous or muscular route or for administration in the form of a nasal spray or advantageously for topic application in the form of creams, ointments, lotions, powders or gels.

The vehicles and diluents that may be used in association with the derivatives of the invention are those generally used in this type of indication.

For the previous indications, the dose depends on the method of administration and the treatment desired. Satisfactory results are obtained when the derivative is administered at a daily dose of between 0.1 mg/kg and about 100 mg/kg. For humans, the administration is carried out, for example, by the intravenous route, in a single dose per day or in fractionated doses several times per day, in the form of unitary doses containing a concentration of from 0.001% to about 0.01% of active substance.

I—ACTIVITY OF FORMULA (I) DERIVATIVES ON CELLULAR PROLIFERATION

A) MTT and SAMBA Tests

Figure 1:
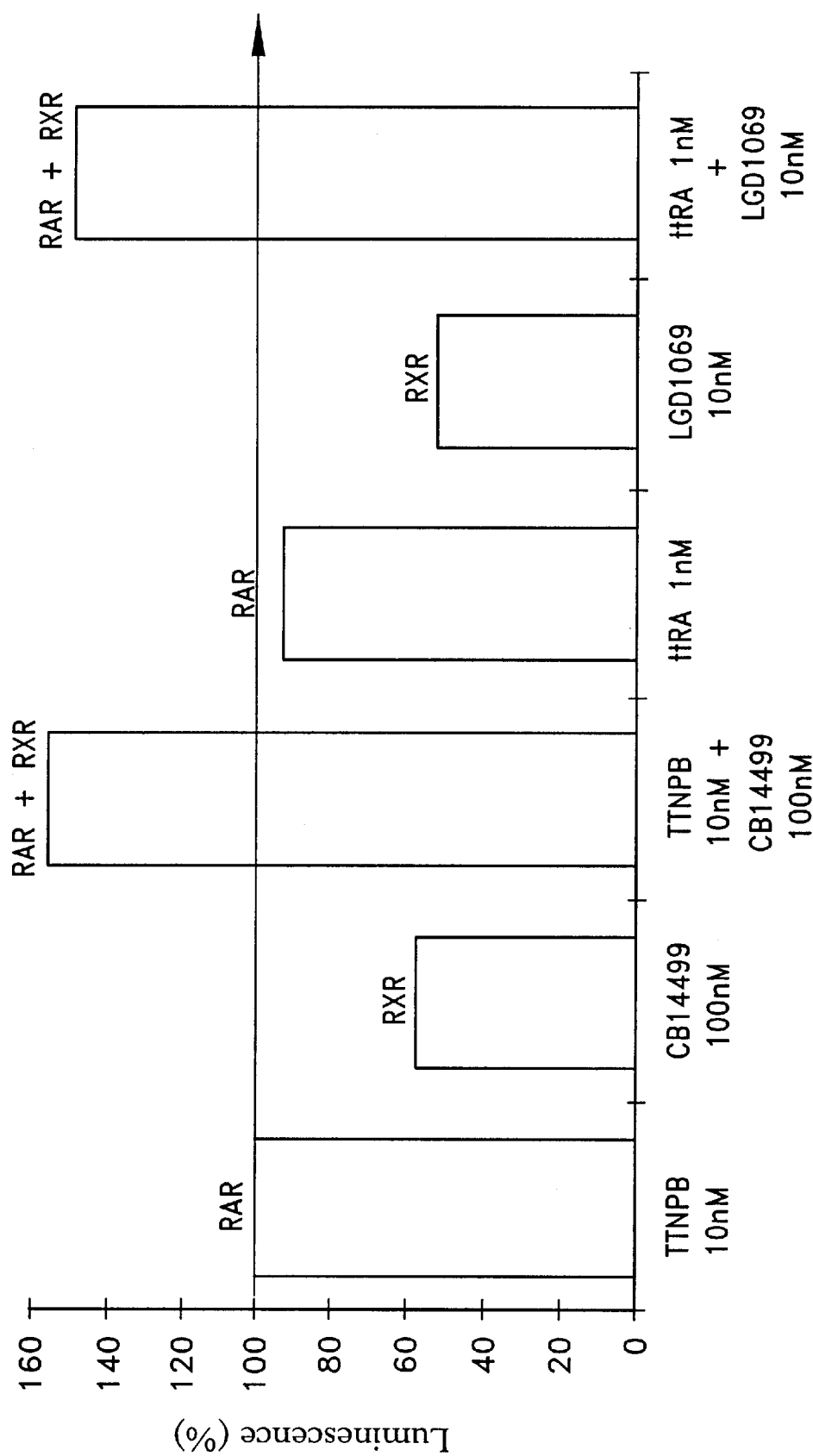
FIG. 1 shows the over-activation induced by a RXR selective molecule in the presence of an RAR specific agonist on the HRL+N model.

The activity of these derivatives on cellular proliferation has been evaluated with the help of the MTT test developed by T. Mosman (J. Immunol. Method., 65, 55– 63, 1983). This test is currently used at the NCI (National Cancer Institute) in the context of the programme of screening anticancer molecules (Alley M. C. et al. Cancer Res., 48, 489–601, 1988). In addition, numerous laboratories specialised in research into chemotherapy and radiotherapy also call upon this model (Arnould R. et al. Anticancer Res. 10, 145–154, 1990 Campling B. G. Leuk. Res., 12, 823–831, 1988; Kasugai S. et al., Japan Pharmacol., 52, 95–100, 1990; Price P. et al. Cancer Res., 50, 1392–1396, 1990).

The molecules which have shown themselves to be the most interesting in the MTT test have been evaluated in an image analysis test called SAMBA. In effect, the recent advances in the field of image analysis have allowed new approaches to the evaluation of different cellular kinetic parameters and the measurement of the distribution of chromatin. The data thereby provided are processed using different statistical tests.

The use of the Système d'Analyses Microscopiques à Balayage Automatique 2005 (SAMBA 2005, Alcatel TITN, France), (System of Microscopic Analyses with Automatic Sweep 2005) permits measurement of the influence of the compounds researched at three levels:

cellular proliferation cellular kinetics the distribution and the texture of the chromatin.

These modifications are representative of the influence of the compound tested on the cellular differentiation.

I—Reactants, Culture Media and Cellular Colonies

The original molecules and said reference products tested have been synthesised following the methods described previously or according to the methods known to those skilled in the art.

The all-trans retinoic acid designated CB16178 and the 13-cis retinoic acid designated CB81808 were acquired from the company Sigma (Saint Quentin Fallavier, France).

Several reference products have been selected:

a) The natural ligands of the two classes of nuclear receptors RAR and RXR known to those skilled in the art:

the all-trans retinoic acid designated CB16178.

the 9-cis retinoic acid prepared according to the method of Corey (Corey E. J., Gilman N. W. and Ganem B. E., J. Am. Chem. Soc., 90, 5616, 1968), designated CB13407 and one of their isomers, the 13-cis retinoic acid designated CB81808.

b) Three reference retinoids known to those skilled in the art:

TTNPB (Loeliger P. et al. Eur. J. Med. Chem., 15, 9–15, 1980) designated CB01570, LGD1069 also designated CB32934 and LGD-CB14499 (Boehm M. F. et al., J. Med. Chem., 37, 2930–2941, 1994).

The cells that were cultured came from the ATCC (American Type Culture Collection). Among the tumour cell lines tested, only the results obtained with four of them are presented below:

A549 (ATCC code: CCL 185) and A-427 (ATCC code: HTB 53) are human pulmonary cancer cells.

ZR-75-1 (ATCC code: CRL 1500) and T47D (ATCC code: HTB 133) are the human mammary cancer cells.

The cellular lines are kept in culture in a monolayer at 37° C. in closed culture dishes (Nunc. Gibco BRL, Life Technologies, Belgium) containing the minimum essential medium (MEM, Gibco) supplemented with 5% of Foetal Calf Serum, (FCS, Gibco), 0.6 mg/ml of glutamine (Gibco) and a mixture of 200 IU/mi of penicillin (Gibco), 200 μg/ml of streptomycin (Gibco) and 0.1 mg/ml of gentamycin (Gibco). The foetal calf serum is decomplemented for 1 hour at 56° C.

2—Experimental Protocols a) MTT Test

The MTT test is carried out according to the method of Carmichael J. et al., Cancer Res., 47, 936–942, 1987 including certain modifications (Etievant C., Anticancer Res., 11, 305–312, 1991).

This test is based on the mitochondrial reduction by living metabolically active cells of the MTT (3-(4,5-dimethylthiazol-2-yl)-2,5-diphenyltetrazolium bromide) of yellowish colour into a blue coloured product, formazan. The quantity of formazan obtained is directly proportional to the number of living cells. After incubation of the cells for 24 hours in microplates with 96 flat bottomed wells, the culture medium is replaced by 100 µl of fresh culture medium containing the drug to be tested. After 72 hours incubation in the presence or not of the molecule to be researched, the culture medium is then replaced by 100 µl of MTT (Sigma, Belgium) dissolved at the rate of 1 mg/ml in RPMI 1640 (Roswell Park Memorial Institute, Gibco).

The microplates are then incubated for 3 hours at 37° C. and centrifuged for 10 minutes at 400 g (GPR centrifuge, Beckman). The MTT solution is replaced by 100 µl of dimethylsulphoxide (Merck). The microplates are agitated (Vari-Shaker, Dynatech) for 10 minutes. Measurement of the optical density is then carried out (DIAS Reader, Dynatech) at the wavelength of 570 nm and at the reference wavelength (maximum absorption of background noise) of 630 nm (Alley M. C. et al., Cancer Res., 48, 489–601, 1988).

In the microplates, the control cells like the treated cells were incubated in a medium without the compounds to be tested for 24 hours. The control cells are incubated in a medium without a drug throughout the whole experiment, while the treated cells are incubated in different media. These media contain the molecule to be tested at various concentrations: $10^{-8}$ M, $10^{-6}$ M and $10^{-4}$ M. All the tests are carried out in 6 duplicates.

Statistical Analysis

The results are presented in the form of a mean±the standard error on the mean (ESM). The statistical comparisons are carried out according to the Fisher Test:
NS*=P<0.05; **=P<0.01; *P<0.001.

b) SAMBA Test

The cells in exponential growth are cultured on small glass slip plates (Kiss R. et al. Eur. J. Cancer, 27, 1268–1274, 1991) at the rate of from $20 \times 10^3$ M to $60 \times 10^3$ M cells/ml (depending on the cellular line being considered) in 3 ml of minimum essential medium (MEM, Gibco). The 18×18 mm slips are placed in Petri dishes of size 35×10 mm (Becton-Dickison). The cells were cultivated for 96 hours. The treatment of the cells, if it takes place, is carried out 24 hours after the transfer. The culture medium is then replaced by media that includes various concentrations of the substances to be studied.

The control cells are cultivated in the absence of drugs.

For each experimental condition, 3 plates are fixed after 96 hours of culture in EFA (75 volumes of 96° ethanol, 20 volumes of neutral 40% formalin and 5 volumes of pure acetic acid) for 20 minutes. The control cells are fixed at the same time. After fixation, the glass slips are mounted on histological plates with the help of Canada balm (DPX, BDH Chemicals) and stored at 4° C. in the dark.

The histological plates supporting the small glass slips are then coloured by the Feulgen reaction (Z. Physiol. Chem., 135, 203–248, 1924) in accordance with the protocol described by Kiss R. et al. (Modern Pathol. 5, 655–660, 1992). All the slips in a given experimental condition are coloured at the same time for one hour in the Feulgen reactant (pararosaline chloride—C.I., Aldrich, France; Noritt PN5, BDH) after hydrolysis in HCl for 1 hour at 22–24° C. The cells are kept at ambient temperature before analysis.

The interest in the Feulgen coloration resides in the possibility of colouring the DNA in a specific and stoichiometric fashion (Giroud F., Cell, 44, 177–188, 1982; Kiss R. et al., J. Histochem. Cytochem., 41, 6, 935–945, 1993). For each experimental condition, 900 nuclei are analysed by the image analyser. Each nucleus is characterised by 15 morphonuclear parameters, of which 1 is of the morphometric type, 5 of the densiometric type and 9 of the textural type (Brugal G. et al., J. Histochem. Cytochem., 27, 144–52, 1979; Pauweis O. and Kiss R., Meth. Find. Exp. Clin. Pharmacol., 15, 113–124, 1993).

These 15 parameters are calculated by specific software, from:

Histograms of optical density values.

Matrices of section lengths (Galloway M. M., Comput. Graph. Image Proc., 4, 172–179, 1975).

Co-occurrence matrices (Haralick R. M. et al., IEE Trans. Syst. Man Cybern. SMC-3, 610–620, 1973).

Statistics and Mathematical Analysis

The measurements of the cellular growth and the morphonuclear characteristics are presented in the forms of a mean (±standard error on the mean: ESM). The comparison of the means is carried out with the aid of the Fisher F test for the probabilities of $p<0.5$; $p<0.01$ and $p<0.001$.

A principal component analysis followed by a canonical transformation is used in order to distinguish the "typical" nuclei from the nuclei treated by the drugs to be tested. These analyses call upon the multi-varied analysis described by Bartels P. H. (Anal. Quant. Cytol., 433–439, 1980).

3—Results a) MTT Test

The results are recorded in Tables 1 to 6 presented below. The mean optical density measured for each experimental condition is expressed as a percentage in relation to the laid down control condition being equal to 100%.

Table 1 below reports the results of the structure/activity research of compounds corresponding to the following general formula on the ZR-75-1 and T-47D lineages.

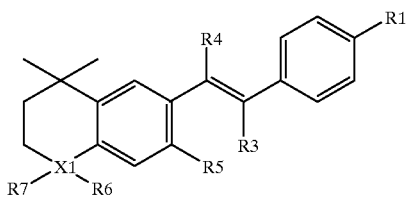

TABLE 1

|  |  |  |  |  |  | ZR-75-1 | | | T-47D | | |
|---|---|---|---|---|---|---|---|---|---|---|---|
|  | $X_1R_7R_6$ | $R_5$ | $R_4$ | $R_3$ | $R_1$ | $10^{-4}$ M | $10^{-6}$ M | $10^{-8}$ M | $10^{-4}$ M | $10^{-6}$ M | $10^{-8}$ M |
| TTNPB | C(Me)$_2$ | H | Me | H | COOH | 15.7 | 69.8 | 60.6 | 3.5 | 61.7 | 58.5 |
| CB01570 |  |  |  |  |  | (4.4) | (14.9) | (18.2) | (0.4) | (1.3) | (0.9) |
| CB77787 | SO$_2$ | OMe | Me | H | COOH | 93.5 | 112.8 | 113.5 | 86.3 | 120.2 | 129.1 |
|  |  |  |  |  |  | (5.6) | (7) | (7.7) |  | (9.1) | (4.1) |

TABLE 1-continued

| | $X_1R_7R_6$ | $R_5$ | $R_4$ | $R_3$ | $R_1$ | ZR-75-1 $10^{-4}$ M | ZR-75-1 $10^{-6}$ M | ZR-75-1 $10^{-8}$ M | T-47D $10^{-4}$ M | T-47D $10^{-6}$ M | T-47D $10^{-8}$ M |
|---|---|---|---|---|---|---|---|---|---|---|---|
| CB65757 | $SO_2$ | OHeptyl | Me | H | COOH | 1 (1.6) | 117.6 (7.3) | 116.3 (6.7) | 0 (0) | 126.1 (3.6) | 124.1 (1.4) |
| CB71802 | $C(Me)_2$ | Me | H | Me | COOH | 7.8 (0.3) | 96 (3.3) | 101.3 (1.8) | 14.3 (1.7) | 113.2 (6.3) | 131.7 (5.5) |
| CB12994 | S | H | H | Me | COOH | 31.8 (2.8) | 125.9 (1.5) | 121.4 (1.6) | '1.8 (0.4) | 51.8 (1) | 67.6 (2.4) |
| CB39356 | $SO_2$ | H | H | Me | COOH | 59.6 (2.6) | 148.4 (0.9) | 133 (2.6) | 36.4 (0.5) | 107.6 (1.8) | 86 (4.3) |
| CB73364 | $C(Me)_2$ | H | H | Me | CONH-tetrazoyl | 0 (0) | 101.1 (1.7) | 119.2 (0.9) | 0 (0) | 53 (1.2) | 62 (2.2) |
| CB62458 | $C(Me)_2$ | H | H | Me | tetrazoyl | 3.2 (1.6) | 102.4 (5.5) | 115.7 (6) | 2.8 (1.5) | 109.5 (4.8) | 116.6 (3.4) |
| CB40747 | $C(Me)_2$ | Me | H | Me | tetrazoyl | 0 (0) | 107.4 (2) | 111.1 (1.7) | 0 (0) | 85.2 (2.8) | 106 (3.4) |
| CB15068 | $SO_2$ | H | H | Me | tetrazoyl | 59.3 (1.3) | 99.9 (1) | 99.2 (1.1) | 32.2 (1.7) | 87.8 (9.3) | 100.6 (0.8) |

The level of proliferation obtained for each lineage and for each product is expressed as a percentage in relation to the control condition (100%±to a maximum, 6% of standard error on the mean).

Table 2 below reports the results of the structure/activity study of compounds corresponding to the following general formula, on the ZR-75-1 and T-47D lineages:

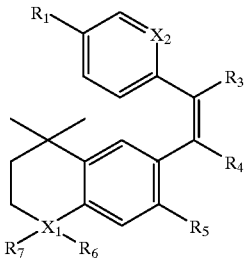

TABLE 2

| | $X_1R_7R_6$ | $X_2$ | $R_5$ | $R_4$ | $R_3$ | $R_1$ | ZR-75-1 $10^{-4}$ M | ZR-75-1 $10^{-6}$ M | ZR-75-1 $10^{-8}$ M | T-47D $10^{-4}$ M | T-47D $10^{-6}$ M | T-47D $10^{-8}$ M |
|---|---|---|---|---|---|---|---|---|---|---|---|---|
| CB28628 | $C(Me)_2$ | CH | H | H | Me | COOH | 19.4 (2.9) | 83.5 (19.8) | 80.8 (19.6) | 4 (0.6) | 59.3 (1.5) | 93.2 (2.4) |
| CB38416 | $C(Me)_2$ | N | H | H | Me | COOH | 55.8 (0.8) | 98.3 (1.9) | 121.8 (4.2) | 42.5 (1.6) | 82.6 (2.5) | 118.8 (4.7) |
| CB36493 | $C(Me)_2$ | CH | H | H | $CF_3$ | COOH | 8.6 (1.3) | 108.0 (4.3) | 108 (4.4) | 21.4 (1.7) | 116.5 (7) | 133.8 (6.6) |
| CB32706 | $C(Me)_2$ | CH | Me | H | Me | COOH | 0.7 (0.2) | 93.1 (5.5) | 95 (2.3) | 0 (0) | 88.6 (3) | 94 (3.6) |
| CB62899 | $C(Me)_2$ | CH | Me | H | $CF_3$ | COOH | 0.4 (1.9) | 111.9 (6) | 112.1 (8.5) | 1.7 (1.5) | 73.7 (7.4) | 128.1 (3.5) |
| CB41666 | S | CH | H | H | Me | COOH | 48.5 (3.1) | 114.7 (2.1) | 112 (1.8) | 28 (1) | 69.5 (2) | 88.7 (3.5) |
| CB72484 | $SO_2$ | CH | H | H | Me | COOH | 128.8 (3) | 137.6 (2.8) | 144.6 (3.4) | 99 (2.5) | 128.5 (2.9) | 129 (4.1) |
| CB92834 | $C(Me)_2$ | CH | H | H | Me | tetrazoyl | 18.7 (2.7) | 39.9 (12.6) | 27.9 (2.9) | 3.5 (0.5) | 83.2 (1.3) | 86.5 (2.7) |
| CB77402 | $C(Me)_2$ | CH | H | H | $CF_3$ | tetrazoyl | 7.5 (0.3) | 96.6 (3.9) | 99.9 (3.5) | 15.4 (1.6) | 118 (4.3) | 127.5 (5.9) |
| CB61692 | $C(Me)_2$ | CH | Me | H | Me | tetrazoyl | 0 (0) | 89.5 (2.9) | 93.2 (1.5) | 0 (0) | 93.8 (2) | 106.4 (1.6) |
| CB63237 | $C(Me)_2$ | CH | Me | H | $CF_3$ | tetrazoyl | 0 (0) | 106.3 (4.6) | 86.5 (2.8) | 4.1 (1.3) | 125.3 (5.6) | 120.4 (4.4) |
| CB39122 | $SO_2$ | CH | H | H | Me | tetrazoyl | 74.2 (1.3) | 97.3 (3.1) | 101.6 (0.6) | 57.1 (2.5) | 100 (3.1) | 102.5 (0.9) |

The level of proliferation obtained for each lineage and for each product is expressed as a percentage in relation to the control condition (100%±to a maximum, 6% of standard error on the mean).

Table 3 below reports the results of the structure/activity study of compounds corresponding to the following general formula, on the ZR-75-1 and T-47D lineages:

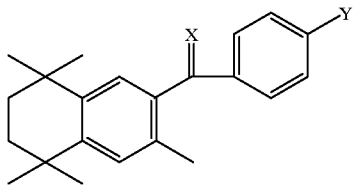

The level of proliferation obtained for each lineage and for each product is expressed as a percentage in relation to the control condition (100%±to a maximum, 6% of standard error on the mean).

Table 5 below reports the results of the structure/activity study of compounds corresponding to the following general formula, on the A549 and A-427 lineages:

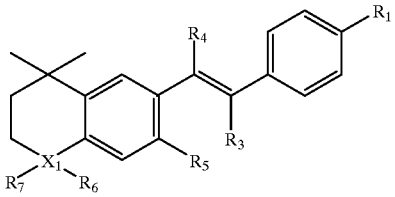

TABLE 3

| | | | ZR-75-1 | | | T-47D | | |
|---|---|---|---|---|---|---|---|---|
| | X | Y | $10^{-4}$ M | $10^{-6}$ M | $10^{-8}$ M | $10^{-4}$ M | $10^{-6}$ M | $10^{-8}$ M |
| LGD-CB14499 | O | COOH | 42.4 (0.6) | 104.5 (1.4) | 106.7 (1.2) | 1.3 (0.6) | 82.7 (3.8) | 88.2 (32.2) |
| LGD1069 CB32934 | $CH_2$ | COOH | 0 (0) | 152.6 (1) | 139.4 (2.5) | 3.3 (0.7) | 99.3 (2.8) | 108 (2.6) |
| CB81616 | O | CONH(4OH—Ph) | 0 (0) | 133.5 (5.2) | 135.7 (4) | 1.4 (0.5) | 96.7 (2.5) | 103.1 (3.1) |
| CB65801 | $CH_2$ | CONH(4OH—Ph) | 0.2 (0.2) | 93.4 (3.3) | 138.3 (3.1) | 1.6 (0.7) | 62.7 (3.1) | 92.8 (2.8) |

The level of proliferation obtained for each lineage and for each product is expressed as a percentage in relation to the control condition (100%±to a maximum, 6% of standard error on the mean).

Table 4 below reports the results of the structure/activity study of compounds corresponding to the following general formula, on the ZR-75-1 and T-47D lineages:

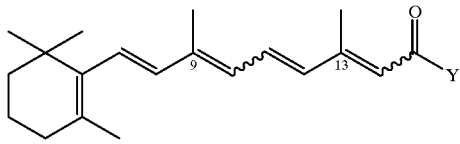

TABLE 4

| | | | | | ZR-75-1 | | | T-47D | | |
|---|---|---|---|---|---|---|---|---|---|---|
| | Bond 9 | Bond 13 | Y | Name | $10^{-4}$ M | $10^{-6}$ M | $10^{-8}$ M | $10^{-4}$ M | $10^{-6}$ M | $10^{-8}$ M |
| CB16178 | trans | trans | OH | all-trans-RA | 7.3 (0.8) | 57.2 (11) | 46.9 (11.7) | 1.8 (0.6) | 52.6 (1.4) | 77.2 (1.4) |
| CB81808 | trans | cis | OH | 13-cis-RA | 2.3 (1.4) | 55 (18.9) | 41.6 (9.5) | 9.94 (0.4) | 51.8 (1.9) | 70.3 (1.8) |
| CB13407 | cis | trans | OH | 9-cis-RA | 39.2 (1.8) | 130.1 1.4 | 137 (2) | 16.3 (1.4) | 91.7 (1.9) | 122 (2.7) |
| CB05764 | trans | trans | 4-amino phenol | 4-HPR | 0.6 (0.1) | 81.9 (2.3) | 97.3 (2.5) | 0 (0) | 66.4 (1.4) | 82.5 (5.1) |

TABLE 5

| | $X_1R_7R_6$ | $R_5$ | $R_4$ | $R_3$ | $R_1$ | A549 $10^{-4}$ M | A549 $10^{-6}$ M | A549 $10^{-8}$ M | A-427 $10^{-4}$ M | A-427 $10^{-6}$ M | A-427 $10^{-8}$ M |
|---|---|---|---|---|---|---|---|---|---|---|---|
| CB01570 TTNPB | $C(Me)_2$ | H | Me | H | COOH | 13.5 (1) | 92.5 (3) | 94.7 (1.3) | 3.6 (0.6) | 78.5 (4.6) | 78.9 (3.4) |
| CB77787 | $SO_2$ | OMe | Me | H | COOH | 102.9 (2.8) | 125.1 (2.6) | 117.9 (2.7) | 163.3 (11) | 110.2 (5.3) | 119.8 (8.01) |
| CB65757 | $SO_2$ | OHeptyl | Me | H | COOH | 0 (0) | 110.9 (8) | 107.6 (705) | 0 (0) | 145.6 (6.8) | 105.5 (5.6) |
| CB71802 | $C(Me)_2$ | Me | H | Me | COOH | 12.5 (0.9) | 86.3 (4) | 80.9 (4.4) | 1 (0.5) | 65.6 (1.3) | 69.7 (2.4) |
| CB12994 | S | H | H | Me | COOH | 53.2 (1.2) | 89 (2.2) | 92.1 (2) | 4.4 (1.1) | 93.6 (2.5) | 107.3 (2.4) |
| CB39356 | $SO_2$ | H | H | Me | COOH | 72 (2.8) | 104.8 (2) | 104.8 (4.2) | 70.7 (1) | 128.9 (3.4) | 124.2 (3.1) |
| CB73364 | $C(Me)_2$ | H | H | Me | CONH-tetrazoyl | 0 (0) | 151.4 (8.1) | 155.6 (6.4) | 0.1 (0.1) | 87.2 (2.4) | 92.7 (1.4) |
| CB62458 | $C(Me)_2$ | H | H | Me | tetrazoyl | 0 (0) | 104.7 (4.3) | 107.3 (3.7) | 0 (0) | 119 (7.8) | 109.6 (6.4) |
| CB40747 | $C(Me)_2$ | Me | H | Me | tetrazoyl | 0 (0) | 191.9 (4.8) | 175.6 (4.8) | 1.7 (0.8) | 83.7 (3) | 100.4 (3.7) |
| CB15068 | $SO_2$ | H | H | Me | tetrazoyl | 81.8 (1.2) | 97.3 (1.1) | 92.7 (3.3) | 24.3 (3) | 98 (5.2) | 88.5 (6.2) |

The level of proliferation obtained for each lineage and for each product is expressed as a percentage in relation to the control condition (100%±to a maximum, 6% of standard error on the mean).

Table 6 below reports the results of the structure/activity study of compounds corresponding to the following general formula, on the A549 and A-427 lineages:

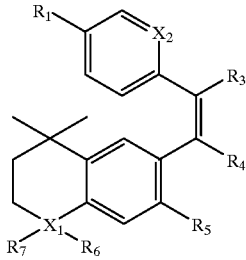

TABLE 6

| | $X_1R_7R_6$ | $X_2$ | $R_5$ | $R_4$ | $R_3$ | $R_1$ | A549 $10^{-4}$ M | A549 $10^{-6}$ M | A549 $10^{-8}$ M | A-427 $10^{-4}$ M | A-427 $10^{-6}$ M | A-427 $10^{-8}$ M |
|---|---|---|---|---|---|---|---|---|---|---|---|---|
| CB28628 | $C(Me)_2$ | CH | H | H | Me | COOH | 12.4 (1) | 93.4 (4.6) | 108.8 (3.7) | 2.5 (0.7) | 86.8 (3) | 86.7 (2.8) |
| CB38416 | $C(Me)_2$ | N | H | H | Me | COOH | 109.3 (4.1) | 104.7 (6.4) | 126 (3.4) | 24.1 (1.8) | 105 (1.5) | 105.8 (2.7) |
| CB36493 | $C(Me)_2$ | CH | H | H | $CF_3$ | COOH | 10.4 (1.4) | 93.7 (2.1) | 98.5 (2.9) | 1.6 (0.6) | 87.2 (4.2) | 89.9 (4.2) |
| CB32706 | $C(Me)_2$ | CH | Me | H | Me | COOH | 6 (0.3) | 103.2 (2.3) | 101.4 (3.4) | 0.8 (0.6) | 99.6 (8) | 102.9 (3) |
| CB62899 | $C(Me)_2$ | CH | Me | R | $CF_3$ | COOH | 0.45 (1.2) | 118.8 (2.5) | 131.2 (4.2) | 0 (0) | 123.8 (7.7) | 115.4 (12) |
| CB41666 | S | CH | H | H | Me | COOH | 63.2 (1.9) | 89.9 (2.3) | 94.5 (1.5) | 7.6 (1.2) | 91.2 (6.6) | 83 (2.5) |
| CB72484 | $SO_2$ | CH | H | H | Me | COOH | 129.4 (2.6) | 111.1 (1.2) | 113.7 (4.1) | 181.5 (5) | 129.6 (2.8) | 131.2 (1.5) |
| CB92834 | $C(Me)_2$ | CH | H | H | Me | tetrazoyl | 14.4 (1.5) | 108.8 (4.5) | 104.7 (2.4) | 3.1 (0.5) | 78.3 (3.3) | 80.5 (2.1) |
| CB77402 | $C(Me)_2$ | CH | H | H | $CF_3$ | tetrazoyl | 10.7 (0.7) | 86 (7.4) | 93.1 (1.6) | 0.2 (0.1) | 77.6 (4.2) | 82.3 (5.4) |
| CB61692 | $C(Me)_2$ | CH | Me | H | Me | tetrazoyl | 0 (0) | 98.2 (2.9) | 105.6 (2.8) | 0.6 (0.6) | 107 (1.7) | 104.7 (2.8) |
| CB63237 | $C(Me)_2$ | CH | Me | H | $CF_3$ | tetrazoyl | 2.1 (0.9) | 140.2 (4.5) | 124 (5) | 4.1 (6) | 147.9 (12.4) | 88.1 (11.1) |
| CB39122 | $SO_2$ | CH | H | H | Me | tetrazoyl | 84.8 (2.2) | 98 (1.2) | 96.2 (3) | 27.1 (2.7) | 96.5 (5) | 93.9 (3.1) |

The level of proliferation obtained for each lineage and for each product is expressed as a percentage in relation to the control condition (100%±to a maximum, 6% of standard error on the mean).

Table 7 below reports the results of the structure/activity study of reference compounds CB16178, CB81808, CB13407, CB01570 and CB32934 on the A549 and A-427 lineages:

TABLE 7

| | | A549 | | | A-427 | | |
|---|---|---|---|---|---|---|---|
| | Name | $10^{-4}$ M | $10^{-6}$ M | $10^{-8}$ M | $10^{-4}$ M | $10^{-6}$ M | $10^{-8}$ M |
| CB16178 | AR-all-trans | 22.3 | 89.2 | 78.8 | 1.5 | 68.2 | 104.3 |
| | | (0.9) | (1.7) | (2.1) | (0.8) | (10.8) | (2.8) |
| CB81808 | AR-13-cis | 23.6 | 85.9 | 77.6 | 6.5 | 99.6 | 100.3 |
| | | (1) | (2.5) | (2.5) | (1.5) | (4.3) | (3.6) |
| CB13407 | AR-9-cis | 38 | 102.3 | 103.5 | 5.9 | 106.3 | 110.8 |
| | | (1.3) | (1.7) | (1.5) | (0.4) | (4.2) | (3.6) |
| CB01570 | TTNPB | 13.5 | 92.5 | 94.7 | 3.6 | 78.5 | 78.9 |
| | | (1) | (3) | (1.3) | (0.6) | (4.6) | (3.4) |
| CB32934 | LGD1069 | 0 | 118.3 | 134.2 | 0.4 | 102.3 | 108.9 |
| | | (0) | (3.9) | (3.8) | (0.3) | (3.2) | (6.2) |

The level of proliferation obtained for each lineage and for each product is expressed as a percentage in relation to the control condition (100%±to a maximum, 6% of standard error on the mean).

Results Relating to the A549 and A-427 Pulmonary Lineages

The reference products are globally inactive on these lineages at concentrations of $10^{-6}$ M and $10^{-8}$ M. Only the all-trans retinoic acid (CB16178) and the 13-cis-retinoic acid (CB81808) inhibit the proliferation of the A549 lineage at $10^{-6}$ M and $10^{-8}$ M. TTNPB (CB01570) inhibits the A-427 lineage at $10^{-6}$ M and $10^{-8}$ M. LGD1069 (CB32934) induces a stimulation of the proliferation of the A549 cells at $10^{-6}$ M and $10^{-8}$ M. Among the derivatives in which the groups $R_3$ and $R_4$ carried by the double bond between carbon atoms 11 and 12 are in the trans configuration, compound CB71802 inhibits the increase of these two pulmonary lineages the most strongly. In contrast to this, a stimulation of the cellular increase is observed with CB39356 (A-427), CB73364 (A549) and CB40747 (A-427). The other molecules show either no activity or little activity on these lineages. Among the derivatives of Formula (I) conforming to this invention, compounds CB92834 and CB77402 show activity on the increase of these two lineages. The other molecules do not exhibit any significant activity on these two lineages.

Results Relating to the Mammary Lineages ZR-75-1 and T47D

Among the reference products, the all-trans retinoic acid (CB16178) and the 13-cis retinoic acid (CB81808) like TTNPB (CB01570) inhibit the cellular increase of the two mammary lineages at the concentrations tested. The 9-cis retinoic acid (CB13407) stimulates the cellular increase at $10^{-6}$ M and $10^{-8}$ M.

The various derivatives in which the groups $R_3$ and $R_4$ carried by the double bond between carbon atoms 11 and 12 are in the trans configuration, like the compound CB62458 and the bio-isosteric compounds CB39356 and CB15068 do not influence the cellular increase of the lineages under consideration. Only compound CB73364 inhibits the increase of the T-47D cells.

Among the derivatives of Formula (I) conforming to this invention, compound CB92834 shows a strongly inhibitive activity on the cellular increase of the two lineages. The other molecules proved to be less powerful or inactive.

Conclusions a) MTT Test

Among the reference retinoids tested: the all-trans retinoic acid (CB16178), the 13-cis retinoic acid (CB81808), the 9-cis retinoic acid (CB13407), TTNPB (CB01570) and LGD1069 (CB32934), TTNPB induces the strongest inhibition of the cellular lineages. Product CB92834 appears to be as active on the MTT test as the reference products tested. Compound CB92834 is more active on the oestrogen-sensitive lineages such as the mammary lineages ZR-75-1 and T-47D than on the pulmonary lineages. The antiproliferative activity of CB92834 on the mammary tumour lineages, determined in vitro with the help of the MTT test is found again and correlates with the results obtained on the SAMBA image analysis system. These two different techniques are evidence of the anti-neoplastic activity of this retinoid.

Quantitative analysis of the image of the nuclei coloured in a specific and stoichiometric way rests on the calculation of 15 morphonuclear parameters determined from:

the histogram of the optical density values matrices of section length co-occurrence matrices.

The statistical processing of the data obtained allows one to determine and to characterise the anti-tumoral action of the retinoids using:

the proliferation index the cellular kinetics the organisation of the distribution and the texture of the chromatin.

b) SAMBA Test

The image analysis of the coloured nuclei allows one to obtain a histogram of the DNA and to calculate a proliferation index. In addition to the study of the kinetics of the cellular cycle, the image analysis of these nuclei through the measurement of 15 parameters and the quantification of the chromatin allows one to determine the influence of the drug on the cytological state of the differentiation.

TTNPB (CB01570) and the compound CB92834 differ in their influence on the morphological differentiation of the T-47D lineage while their capacities for the inhibition of the overall cellular proliferation (MTT Test) of the neoplastic cells prove to be comparable. The dose dependent effect of TTNPB on the value of the different morphonuclear parameters processed by multi-varied analysis strongly suggests a direct correlation between the cytotoxic effect of the molecule and its anti-tumoral activity. Contrary to this, the anti-tumoral effect of CB92834 is not linked to a cytotoxic effect bu: to a modulation of the ratio of cellular gain over cellular loss and to induction of the cellular differentiation.

TTNPB (CB01570) exercises its anti-tumoral activity through a direct cytotoxic (cytocidal) effect while the anti-tumoral power of compound CB92834 would be mediated by an activation of the cellular death and/or an inhibition of the proliferation due to the induction of the cellular differentiation.

The derivatives of Formula (I), and more particularly compounds CB92834 and CB77402, distinguish themselves by their interesting pharmacological properties and can, as a consequence, be used in human or animal therapy as a medicine as well as in cosmetology.

B) Clonogenic Tests

By definition a cell is considered clonogenic if it possesses the ability to proliferate and to give birth to a cellular colony containing a minimum 50 cells. The human tumour stem cells are the clonogenic cells which are the origin of the neoplasic cells which constitute a given tumour. These tumour stem cells are responsible for the recidivism process observable after surgical resection of the primary tumours and are also responsible for the formation of metastases. They have also become the primary target of certain anti-cancer chemotherapies (Fialkow P. J. et al., Am. J. Med., 1977, 63, 125–130; Hamburger A. W. and Salmon S. E., Science, 1977, 197, 461–463; Selby P. et al., N. England J. Med., 1983, 308, 129–134; Steel G. G., Growth kinetics of tumour, Clarendon Press, 1977). At the level of a tumour or of a tumoral cellular lineage, these clonogenic stem cells distinguish themselves from other clonogenic cells of the tumour or of the neoplasic cellular lineage being considered, by the fact that they preserve their ability to proliferate in the absence of any solid support.

A simple method called "a clonogenic test" (colory forming assays or stem cell assay) has been developed by Hamburger A. H. and Salmon S. E. in 1977. This technique is suitable for the culturing in vitro of most of the tumours and tumoral cellular lineages of various histological types. In the context of this test, the neoplasic cells are cultured on a semi-solid culture medium "soft agar" made up of a mixture of agar and agarose. On this selective support, only tumoral stem cells survive and proliferate. In effect, on such a culture medium, the normal cells, such as, for example the fibroblasts do not survive. Under these conditions, as a function of the tumour or of the tumoral cellular lineage being considered, the percentage of tumoral cells capable of proliferating and giving birth to a cellular colony is only between 0.1 and 0.001%. The morphological characteristics and the growth of the cellular colonies are also a function of the histological type of the tumours being considered.

This technique remains the most commonly used and the most suitable for the study of the effects of anti-cancer drugs on the stem cells of human tumours. In effect the first in vitro studies that rely on this type of test indicate that a correct prediction of the response to treatment by chemotherapy is possible in about 60% of cases and that a correct prediction of the resistance of a tumour to a treatment by chemotherapy can be proven in more than 90% of cases (Van Hoff D. D., Semin. Oncol. 1985, 12, 327–331; Bertelsen C. A., Cancer, 1984, 53, 1240–1245). This test allows one to study and to describe the biological properties, the sensitivity to the various anti-cancer agents used in chemotherapy. For one and the same patient, this test allows one to study the heterogeneity of the response to a given drug at the heart of one and the same tumour, between the primary tumour and its metastases and finally between the different metastases (Tanigawa N. et al. Cancer Res., 1984, 44, 2309–2312) The study of the clonogenic increase in the tumoral cells of a given tumour on a semi-solid culture medium seems to be linked to the degree of malignity of the tumour being considered (Dittrich C. et al., J. Clin. Oncol. 1991, 9, 381–388; Von Hoff D. D. et al., Cancer Res. 1983, 43, 1926–1931; Alberts D. S. et al., Lancet, 1980, 2, 340–343; Meyskens F. L. et al. Br. J. Cancer, 1981, 44, 787–797; Salmon S. E. et al. Cancer Research 1980, 74, 300–305; Salmon S. E. et al., Cloning of human tumour stem cells, 1980, 223–245; Von Hoff D. D. et al., Am. J. Med. 1981, 70, 1027–1032).

In the context of the invention, the influence of various retinoids on the growth of the cellular colonies obtained by cultivating the mammary tumoral lineage T-47D on this semi-solid culture medium "soft agar" has been measured. These culture conditions are also called "anchorage-independent" conditions.

1) Materials and Methods a) Reactants, Culture Medium and Tumoral Cellular Lineage Reactants The derivatives of the invention and the reference products tested have been synthesised following the procedures which will be described below and in accordance with procedures known to men skilled in the art.

Commercial tamoxifen, designated CB58707, and 4-hydroxytamoxifen, designated CB05764, were acquired from the company Sigma (Saint Quentin Fallavier, France).

Several reference retinoids, ligands for the two classes of nuclear receptors RAR and RXR, known to men skilled in the art, were selected:

The 9-cis retinoic acid, a natural ligand, designated CB13407.

TTNPB designated CB01570.

An analogue of TTNPB $SR_1$ designated CB28628

LGD1069 designated CB32934.

A culture medium.

The base medium "MEM 25 MM HEPES" (Minimum Essential Medium, Life Technologies, Belgium) contains Eagle salts but no L-glutamine. This medium is well suited to the growth of a range of varied diploid cells or primary mammal cells. To this medium is then added:

a quantity of 5% of FCS (Foetal Calf Serum, Life Technologies, Belgium), decomplemented at 56° C. for 1 hour, 0.6 mg/ml of L-glutamine (Life Technologies, Belgium), 200 IU/ml of penicillin (Life Technologies, Belgium), 200 tg/ml of streptomycin (Life Technologies, Belgium), 0.1 mg/ml of gentamicin (Life Technologies, Belgium), a tumoral cellular lineage.

The human tumoral cellular lineage of mammary origin T-47D used in the context of this work came from the ATCC (American Type Culture Collection, ATCC code: HTB 133).

b) Experimental Protocol

The tumoral cells are maintained in culture in 25 $cm^2$ falcon dishes (Life Technologies, Belgium). They are then trypsinised and individualised. Their rate of viability is determined by coloration with trypan blue (Sigma, Belgium). It must be greater than 90%. In the case where this condition is kept to, a cellular suspension at the desired concentration is prepared in a solution of agar at 0. 3%. The cells are then seeded between two layers of agar (Sigma, Belgium) and in 35 mm Petri dishes (Life Technologies, Belgium). The base layer is made up of a 0.5% solution of agar and the top layer is made up of a 0.3% solution of agar. The cupules are then positioned and held in an incubator at 37° C. and 5% of $CO_2$. Twenty four hours after seeding, the cells are treated by depositing on the top layer, the various products to be tested at concentrations 100 times greater than the final desired concentration since the volume of the treatment solution added is 100 times lower than the total volume of agar placed in the Petri dishes. After treatment, the cupules are kept in the incubator for 21 days. It is advisable to examine, during the course of the experiment, the appearance and the increase of the cellular colonies. If after 10 days, no colony appears or is developing, the experiment must be repeated. In the contrary case, on the 21st day, 100 μl of an MTT solution (3-(4,5-dimethylthiazol-2-yl)-2,5 diphenyl tetrazolium bromide; Sigma, Belgium) dissolved in the RPMI culture medium (Roswell park Memorial Institute, Life Technologies, Belgium), at the concentration of 1 mg/ml are deposited on the top layer of the group of cupules. The cells are kept in contact with this solution for a minimum of 3 hours at 37° C. The metabolically active cells then transform, by mitochondrial reduction, this yellowish solution into blue crystals of formazan thereby allowing the cellular colonies present to be given prominence (Mosmann, 1983; Carmichael et coll., 1987).

Using an inverted microscope at low magnification, the number of clones whose surface area is greater thar. 100 μm² is determined for the group of cupules representing all the different experimental conditions. Then, for each of these experimental conditions, the mean number of cellular colonies±the standard error on the mean (ESM) is calculated.

c) Statistical Analysis

The results obtained under the treated conditions are compared with those obtained under the control condition by means of a statistical analysis of the non-parametric type and in accordance with the Mann-Whitney Test (NS: $P>0.05$; *: $P<0.05$; : $P<0.01$; *: $P<0.001$).

2) Results

The results are presented in Tables 8 to 10. The mean number of cellular colonies determined for each experimental condition is expressed as a percentage in relation to the control condition made equal to 100%.

a) Results Relating to the Reference Products

Table 8 below groups together the results obtained with the chosen reference products.

TABLE 8

| | | Cellular lineage T-47D | | | |
|---|---|---|---|---|---|
| Code | Name | $10^{-7}$ M | $10^{-8}$ M | $10^{-9}$ M | $10^{-10}$ M |
| CB58707 | Tamoxifen | 31.3 ± 3.9 (*) | 46.9 ± 2.6 (*) | 35.5 ± 4.2 (*) | 56.7 ± 3.4 (*) |
| CB01570 | TTNPB | 1.3 ± 0.2 (*) | 2.1 ± 0.4 (*) | 5.5 ± 1 (*) | 34.1 ± 7.9 (*) |
| CB13407 | 9-cis RA | 6.7 ± 1.8 (*) | 45.6 ± 4.8 (*) | 52.8 ± 3.9 (*) | 54.9 ± 7.2 (*) |
| CB05764 | 4-HPR | 18.8 ± 1.1 (*) | 33.6 ± 3 (*) | 83.3 ± 7.3 (NS) | 80.3 ± 12.9 (NS) |
| CB32934 | LGD1069 | Not tested | 24.7 ± 3.3 (*) | 31.1 ± 0.3 (*) | 37 ± 9.3 (*) |
| CB28628 SR1 | Analogue of TTNPB | 21.4 ± 2.4 (*) | 97.6 ± 6.6 (NS) | 89.2 ± 3.6 (NS) | Not tested |

The results obtained show that the chosen reference products inhibit in a different manner, the growth of cellular colonies of the human mammary tumoral lineage T-47D.

Tamoxifen (CB58707), a molecule with anti-oestregen activity, at the concentrations tested (here $10^{-7}$ M to $10^{-10}$ M) induces a significant inhibition in the growth of these colonies but its activity is not dose dependent, which is not the case with its homologue 4-HPR. The latter, strongly active at concentration $10^{-7}$ M loses its significant inhibiting activity beyond the concentration of $10^{-9}$ M. The natural retinoid 9-cis retinoic acid (CB13407) exhibits significant and dose dependent inhibiting activity. Finally the synthetic retinoid TTNPB (CB01570) inhibits very strongly, in a significant and dose dependent manner the growth of cellular colonies of the T-47D lineage. It should be noted that its inhibiting activity is still 66% at the concentration of $10^{-10}$ M. LGD1069, a specific ligand for RXR nuclear receptors, strongly and significantly inhibits the growth of cellular colonies of the T-47D lineage. If its inhibitive activity is feebly dose dependent, it remains nevertheless very high at the concentration of $10^{-8}$ M (63%). The retinoid SRI-CB28628 strongly and significantly inhibits the growth of the cellular colonies at the concentration of $10^{-7}$ M but very rapidly loses its activity beyond the concentration of $10^{-8}$ M.

b) Results Relating to the Series (E) Products

Table 9 below summaries the group of results relating to the retinoids of the trans series (E).

TABLE 9

| | Cellular lineage T-47D | | |
|---|---|---|---|
| Code | $10^{-8}$ M | $10^{-9}$ M | $10^{-10}$ M |
| CB12273 | 71.2 ± 2.9 (*) | 93.9 ± 3.3 (NS) | 92.9 ± 21.7 (NS) |
| CB40341 | 65.6 ± 9.5 (*) | 90.8 ± 0.8 (NS) | 99.1 ± 9.7 (NS) |
| CB71239 | 58 ± 4.1 (*) | 86.6 ± 9.4 (NS) | 95.5 ± 1.7 (NS) |
| CB38973 | 38.6 ± 3.6 (*) | 60.1 ± 2 (*) | 68.4 ± 8.3 (*) |
| CB57201 | 64.8 ± 1.2 (*) | 58.9 ± 11 (*) | 75.2 ± 12.2 (NS) |
| CB71802 | 45.2 ± 4.8 (*) | 92.5 ± 9.6 (NS) | 104.3 ± 2.3 (NS) |
| CB73364 | 10.3 ± 2.8 (*) | 54.9 ± 5.8 (*) | 99.3 ± 7.8 (NS) |

The arotinoids of this trans series (E) induces inhibition of the growth of cellular colonies of the T-47D lineage in a significant manner at the concentration of $10^{-8}$ M. At this concentration, the percentage inhibition of the different products is graded at 69.7% for the product CB73364, at 28.8% for the product CB12273. At the concentration of $10^{-9}$ M only three (CB38973, CB57201 and CB73364) out of the seven products tested inhibit the growth of the cellular colonies. At the concentration of $10^{-10}$ M, only two products (CB38973 and CB57201) out of the seven products significantly inhibit the growth of the colonies. At these two concentrations of $10^{-9}$ M and $10^{-10}$ M, none of the inhibitions induced is greater than 50%.

c) Results Relating to the Products of the cis Series (Z)

Table 10 below summarises the group of results relating to the retinoids of the cis series (Z).

TABLE 9

| Code | Cellular lineage T-47D | | |
|---|---|---|---|
| | $10^{-8}$ M | $10^{-9}$ M | $10^{-10}$ M |
| CB02981 | 48.8 ± 5.3 (*) | 67.6 ± 8.9 (NS) | 80.1 ± 13.2 (NS) |
| CB36493 | 17.4 ± 2 (*) | 24.8 ± 0.5 (*) | 35.8 ± 3.2 (*) |
| CB61692 | 55.7 ± 2.6 (*) | 41.5 ± 5.7 (*) | 90.3 ± 4.7 (NS) |
| CB92834 | 38 ± 2 (*) | 58.9 ± 3.7 (NS) | 82.5 ± 12 (NS) |
| | $10^{-7}$ M | $10^{-8}$ M | $10^{-9}$ M |
| CB16279 | 101.7 ± 3.4 (NS) | 989.8 ± 3.7 (NS) | 110.1 ± 1.5 (NS) |
| CB38416 | 11.6 ± 1.9 (*) | 15.3 ± 1.7 (*) | 20 ± 0.2 (*) |

Among the six products tested in this series, the product CB16279 does not induce any significant modification in the growth of the cellular colonies and this even at the concentration of $10^{-7}$ M. On the other hand, the five other products, at the concentration of $10^{-8}$ M, induce a significant inhibition in the growth of these colonies. At the concentrations of $10^{-9}$ M and $10^{-10}$ M, three products (CB36493, CB61692 and CB38416) out of six and one product (CB36493) out of four significantly inhibit the growth of the cellular colonies of the tumoral lineage T-47D. At these two concentrations, the inhibitions induced by products CB36493, CB61692 and CB38416 are all greater than 50%.

3) Discussion and Conclusion

The results above show that the clonogenic test is a test suited to the selection and to the screening of various retinoids.

Under the same experimental conditions, the inhibiting effects induced by the products of the cis series (Z) on the growth of the cellular colonies of the human mammary tumoral lineage T-47D cultivated on soft agar are for the most part significantly greater than those induced by the products of the trans series (E). One notes that the product CB92834 exhibits a global inhibiting and dose dependent activity as great as that obtained with the best products in the trans series (E). The products of the cis series (Z) show themselves to be more powerful inhibitors of the growth of the tumoral stem cells of the T-47D lineage than the products of the trans series (E). Furthermore, the products CB36493 and CB38416 of the cis series (Z) appear as active as the reference products CB13407 (9-cis RA) and LGD1069. Finally only the reference product TTNPB (CB01570) is more active than the product CB36493 of the cis series (Z).

II—Activities of the Formula I Derivatives on the Retinoic Receptors and Certain Transcriptional Factors I) Models and Reference Molecules The all trans retinoic acid (ttRA) and its stereo-isomers 9-cis, 11-cis and 13-cis bond themselves to and activate more or less selectively, intranuclear receptors called retinoic receptors. An important advance in the molecular action mechanism of the transduction signal of the retinoic acid has been established notably thanks to pioneering work by R. M. Evans et al. (Sciences, 1988, 240, 889–895).

The compounds of the invention of the retinoid or arotinoid type have different selectivity profiles with respect to the sub-types of receptors of the retinoic acid (RARs) and the retinoid X receptors (RXRs).

A large number of recent clinical results have shown that retinoic acid, certain of its isomers and derivatives forming the class of retinoids, are used for the treatment of diseases such as acne, psoriasis and certain cancers (U. Reichert et al., Pharmacology of Retinoids in the Skin, Karger AG Eds, Basel, 1989; M. S. Tallman et al, Retinoids in Cancer Treatment, J. Clin. Pharmacol., 1992, 32, 868–888; Warrell et al., N. Engl. J. Med., 1991, 324, 1385–1393).

These retinoids have also been evaluated in other therapeutic fields such as, arthritis (Vinienti M. P. et al., Using Inhibitors of Metalloproteinases to treat Arthritis, Arthritis Rheumatoidism, 1994, 37, 1115–1126); dyslipidemia (Rottman et al., A RARE Element in the Apolipoprotein AI Gene Distinguishes Between Two Different Retinoic Acid Response pathways, Mol. Cell. Biol., 1991, 3814–3820); the prevention of HIV induced lymphopenia (Yang Y. et al., 9-cis RA Inhibits Activation Driven T-cell Apoptosis: Implications for Retinoid X Receptor Involvement in Thymocyte Development, Proc. Natl. Acad. Sci. USA, 1993, 90, 6170–6174). These therapeutic effects result from the capacity of the retinoic acid and of certain retinoids to control abnormal cellular situations by the modulation of the cellular growth, of the cellular differentiation and/or the apoptosis or programmed cellular death (The Retinoids, Biology, Chemistry and Medicine, M. B. Sporn, A. B. Roberts and D. S. Goodman, Raven Press Eds, 2nd ed, New York 1994). These regulations have been attributed for the large part to the formation of ligand(s)-receptor complexes. These proteins belong to the super-family of nuclear receptors and operate as dependent ligand transcription factors. These are the interactions which are responsible for the transcriptional activation and the associated physiological effects.

Using endogenic and synthetic ligands, this family has been classified into two series named RAR and RXR, each composed of three sub-types of receptors called $\alpha$, $\beta$ and $\gamma$. Furthermore, these retinoids have shown themselves capable of regulating the expression of other genes through an inhibitor effect of transcriptional factors like the complex AP-1 made up of the oncogenic proteins c-Fos and c-Jun. All these receptor proteins modulate the expression of certain genes by selective bonding, in dimer form, to specific regions of the DNA called RAREs (Retinoic Acid Response Elements, M. B. Sporn et al., p.319–349, D. J. Mangelsdorf et al., Proc. Natl. Acad. Sci. USA., 1991, 88, 3559–3563).

The RXR receptors function as homo-dimers or are able to hetero-dimerise themselves with the RAR receptors as well as with the other members of the super-family of intracellular receptors.

The all-trans retinoic acid (ttRA) is the natural ligand of the RAR receptors, while its 9-cis isomer (9-cis RA) is a ligand both for the RXR and RAR receptors in the form of homo-dimers and hetero-dimers (M. B. Sporn, page 5–178, X-K. Zhang et al, Homo-dimer formation of Retinoid X receptor induced by 9-cis RA, Nature, 1992, 358, 587–591, Heyman R. A. et al., 9-cis RA is a high affinity ligand for the retinoic receptor X, Cell, 1992, 68, 397–406, Levin A. A. et al., 9-cis RA stereo-isomer binds and activates the nuclear receptor RXR$\alpha$, Nature, 1992, 355, 359–361).

It has been shown that these receptors are significantly different: the primary structures of the bonding domains (amino-acid composition) are more than 80% different. Similarly, a different distribution of these sub-types of receptors is a function of the nature of the tissues. For example, the RARs are not expressed in the viscera, contrary to this the RXR$\alpha$ mRNA are the most abundant in the liver, the kidneys, the lungs, the intestine and the muscles.

The hormono-dependent routes of the RARs can be activated by the specific RAR ligands which are linked to the RAR part of the RAR-RXR hetero-dimers, while specific RXR ligands show themselves incapable of activating these same routes by fixing themselves onto the RXR part. RXR ligands exhibit an activation synergy for genes responding to the all-trans RA when they are used in association with specific RAR ligands (Roy B. et al., Mol. Cell Biol., 1995, 15, 6481–6487). The RXRs form homo-dimers, in the presence of RXR ligands and regulate the transcription of genes which are distinct from those controlled by the RAR-RXR hetero-dimers (Zhang X-K. et al. quoted above).

Hence retinoids which are selective for the sub-types of receptors will be useful for a selective or independent control of the physiological routes mediated by these same sub-types. By way of comparison a panagonistic agent will be useful to control the physiological routes mediated by several of these sub-types. It appears that retinoids acting selectively on these sub-types will be able to increase the therapeutic efficacy and reduce the profile of secondary effects. A panagonistic agent is defined as an agent which links itself to and activates at least one of the receptors of the RAR sub-family and of the RXR sub-family. A true panagonistic agent activates all the members of the RAR and RXR sub-families.

The all-trans retinoic acid (ttRA), like its 13-cis isomer, has, at the time of any chronic treatment, a powerful effect of hypervitaminose, of mucocutaneous toxicity and of teratogenecity. Furthermore, ttRA is an inducer of its own metabolism which has the direct effect of rapidly reducing its therapeutic efficacy.

This is why, this invention aims to provide new compounds having greater chemical and metabolic stability and different activity profiles in relation to these sub-types of receptors linked to anti-tumoral activities and well established selective anti-proliferative activities. Such a strategy has lead to the formation of molecules which are:

RAR-RXR panagonistic

RAR or RXR selective anti-AP-1 dissociating.

Through their property of co-activation of the RAR proteins, RXR-selective retinoids constitute a new therapeutic advance. At doses where they are inactive themselves, they can increase the activity of RAR-selective retinoids, notably RAR(X, useful in the treatment (regression or remission) of cancers of the leukaemia type, of solid tumours, more particularly cancers of the breast, the head and neck, but also in a more classical way in episodes of acne, severe acne and skin damaged by the sun. The administration of retinoids used in combination, can be concomitant or simultaneous. In this case, the spacing apart of the administration of the retinoids must not exceed a few hours, so that the RXR and RAR retinoids will be in blood concentrations such that the potentialisation is effective.

1) Expression of RAR, RXR and RE Receptors as a Function of Cellular Lineages

MCF-7 cells and HeLa are cultivated in DMFM with phenol red to which 5% foetal calf serum is added. The T47-D cells are cultivated in RPMI to which 10% foetal calf serum is added. The experimental tests are carried out in DMEM without phenol red to which foetal calf serum treated with dextran carbon is added at 3%. The cellular lineages transfected in a stable way, stemming from the MCF-7 and HeLa lineages are established in accordance with the protocol described by D. Gagne et al. (J. Biolumin. Chemilumin., 1994, 9, 201–209). The experiments using the different retinoids are carried out sheltered from the light so as to avoid any isomerisation.

Table 11 below reports the difference of expression of the receptors of retinoic acid and of the receptor to RE oestrogens by the HeLa and MCF-7 cells (Titcomb M. W. et al., Mol. Endocrinol., 1994, 8, 870–877). The results in Table 11 are expressed in fentomoles of receptor per mg of proteins.

TABLE 11

| Type of receptor | HeLa | MCE-7 |
| --- | --- | --- |
| RE | not detected | expressed |
| RARα | 28 | 80 |
| RARβ | 9 | not detected |
| RARγ | 16 | 34 |
| RXRα | 50 | 12 |
| RXRβ | 28 | not detected |
| RXRγ | 9 | not detected |

2) Specificity of the Reference Molecules in Models of Transitory Transfections a) Chimerical Receptors Gal4-RAR Studies of the transactivator specificity of the retinoids have been carried out by transitory transfection of HeLa cells. Two types of chimerical receptors can then be expressed by the cells. The plasmids Gal-RARα, Gal-RARβ and Gal-RARγ (J. Y. Chen et al., EMBO J., 1995, 14, 1187–1197) code for the chimerical receptors Gal4-RAR in which the domain of bonding to the DNA of the yeast protein Gal4 is merged with the E and F regions (regions containing the domain of bonding to the ligand and the activation function AF-2) of the receptors of retinoic acid. The C region (domain of bonding to the DNA) and the A and B regions (AF-1 activation domain) are suppressed.

These chimerical receptors activated by an agonist specifically stimulate the transcription of the gene of the luciferase present in a co-transfected plasmid ((17M)5-βG-Luc) where 17M is the response element of Gal4. The transcriptional co-operation between AF-1 and AF-2 does not exist with this type of receptor.

The use of reference molecules has allowed the validity of the GAL-RAR model to be verified in order to determine the specificity of agonist molecules: this GAL-RAR model translates the affinity of a compound for the domain of bonding to the RAR hormone. The arotinoid TTNPB, at concentration $10^{-8}$ M, is used as a maximum transactivation reference (100%) obtained with a synthetic agonist. Hence TTNPB and all-trans RA are good RAR agonists while Am580 behaves like a RARa specific molecule at a concentration of 10 nM. The compounds described as RXR specific (LGD1069 and LGD-CB14499) do not allow one to observe a good transactivation mediated by RAR. Table 12 below reports these results, where the activity of the compounds is expressed as a percentage of the activity measured for $10^{-8}$ M TTNPB.

The compound designated Am580 is 4-[(5,6,7,8-tetrahydro-5,5,8,8-tetramethyl-2-naphthalenyl)carboxamido]benzoic acid (Shudo K. et al., J. Med. Chem., 1988, 31, 2182–2192).

TABLE 12

GAL4-RAR

| Product | Concentration (Log M) | RARα (%) | RARβ (%) | RARγ (%) |
| --- | --- | --- | --- | --- |
| all-trans RA | −8 | 82 | 104 | 106 |
| | −7 | 102 | 93 | 104 |
| | −6 | 108 | 92 | 111 |
| Am580 | −8 | 110 | 22 | 12 |
| | −7 | 102 | 77 | 64 |
| | −6 | 113 | 111 | 96 |
| TTNPB | −8 | 100 | 100 | 100 |
| | −7 | 101 | 116 | 94 |
| | −6 | 105 | 109 | 112 |
| LGD1069 | −8 | 0 | 1 | 1 |
| | −7 | 7 | 5 | 8 |
| | −6 | 21 | 22 | 29 |
| LGD-CB14499 | −8 | 1 | 0 | 0 |
| | −7 | 4 | 1 | 0 |
| | −6 | 17 | 9 | 13 | b) Chimerical Receptors ERcassettes

The chimerical receptors RAR-ERcassettes have been described by Petkovitch et al. (Nature, 1987, 330, 444–450). The HeLa cells are co-transfected by a plasmid which codes for a retinoic receptor in which the C domain of bonding to the DNA is substituted by that of the receptor to RE oestrogens, and a plasmid which places the expression of the luciferase under the control of an ERE (Element of Response to Oestrogens). The expressed chimerical receptors are designated as RARα-ERcassette, RARβ-ERcassette, RARγ-ERcassette and RXRα-ERcassette. The A, B, D, E and F regions of the natural receptor are preserved as well as the transcriptional co-operation between the activation domains AF-1 and AF-2. These transitory transfection experiments follow the method of co-precipitation to calcium phosphate. The HeLa cells are co-transfected by 0.25 mg of plasmid coding for the chimerical receptor, 1 mg of reporter plasmid and 0.5 mg of expression vector CMV-β-galactosidase used as an internal control of transfection. 24 hours after the transfection, the cells are incubated for 16 hours with the different effectors.

In this type of chimerical receptor, the C domain of bonding to the DNA of RAR is substituted by that of the receptor to the RE oestrogens. The protein obtained is close to the natural RAR receptor and preserves the transcriptional properties of the AF-1 and AF-2 domains. It modulates the transcription by means of an ERE. This RAR-ERcassette model allows one to observe a transcriptional response to a more physiological ligand.

The effect of the natural hormones (all-trans RA and 9-cis RA) is remarkable. These ligands induce an over-expression of luciferase in comparison to the induction brought about by a synthetic compound (TTNPB). This phenomenon is also observed for other responses (cf. notably results of transactivation on the HRLN models). This shows that the RAR-ERcassette constructions reflect a physiological context. The RARα specificity of Am580 is again verified for concentrations less than 10 nM. The profile defined in an RAR-ERcassette for the agonists RXR (LGD1069 and LGD-CB14499) differs from their GAL-RAR profile. In comparison to TTNPB, their transcriptional power appears higher notably through the RARβ-ERcassette. This result can be explained by a hetero-dimerisation of RAR-ERcassette with the endogenous RXR receptors expressed by the transfected HeLa cells. 1 μM LGD1069 permits a co-activation of RAR and RXR, bringing about an over-activation of the hetero-dimer in comparison with the specific RAR activation of TTNPB. The RAR-ERcassette model therefore indicates an RAR activity of a compound and also an RXR activity. Hence any panagonistic molecule causes a maximum transcription greater than that of TTNPB. This observation is confirmed by the fact that if a RAR specific molecule is associated with a RXR specific molecule, an over-expression of luciferase occurs. The use of the RAR-ERcassette construction thus permits one to visualise and to provide evidence for an RXR activity as reported in Table 13 below.

TABLE 13

| | RAR-ERcassettes | | | |
|---|---|---|---|---|
| Product | Concentration (Log M) | RARα (%) | RARβ (%) | RARγ (%) |
| all-trans RA | −9 | 65 | 93 | 86 |
| | −8 | 127 | 128 | 114 |
| | −7 | 249 | 270 | 122 |
| | −6 | 443 | 475 | 189 |
| 9-cis RA | −9 | 7 | 16 | 11 |
| | −8 | 60 | 94 | 56 |
| | −7 | 187 | 212 | 108 |
| | −6 | 348 | 369 | 157 |
| Am580 | −9 | 88 | 6 | 9 |
| | −8 | 113 | 70 | 45 |
| | −7 | 115 | 99 | 93 |
| | −6 | 106 | 89 | 100 |
| TTNPB | −9 | 52 | 93 | 66 |
| | −8 | 100 | 100 | 100 |
| | −7 | 119 | 104 | 97 |
| | −6 | 123 | 116 | 112 |
| LGD1069 | −8 | 14 | 78 | 19 |
| | −7 | 36 | 194 | 41 |
| | −6 | 70 | 237 | 62 |

TABLE 13-continued

| | RAR-ERcassettes | | | |
|---|---|---|---|---|
| Product | Concentration (Log M) | RARα (%) | RARβ (%) | RARγ (%) |
| LGD-CB14499 | −8 | 4 | 10 | 13 |
| | −7 | 12 | 58 | 31 |
| | −6 | 42 | 130 | 66 |

3) Effect of the Reference Retinoids on the Oestrogen-induced Proliferation—Cellular Lineages MCF-7 and T-47D So as to test the anti-proliferation effect of the retinoids, growth experiments under oestrogenic conditions were carried out on cells MCF-7 and T-47D. These are the human oestrogen-dependent mammary cancer cells which express the receptor to RE oestrogens. The effect of the molecules is evaluated after 7 days of culture in oestrogenic conditions (estradiol $10^{-9}$ M) by dosing the cellular DNA. The cells are distributed in 24 well plates at a density of $2 \times 10^4$ cells per well. The tests with the different retinoids are carried out in triplicate and the culture medium is changed after 4 days of growth. The cellular DNA is measured by the method of 4,6-diamidino-2-phenylindole (C. F. Brunck et al., Anal. Biochem., 1979, 92, 497–500). The activity of the compounds is expressed as a percentage, 100% representing the quantity of DNA measured with $10^{-9}$ M estradiol.

Table 14 below shows the concentrations of retinoid required to inhibit by 50% the growth of MCF-7 and T-47D cells, or the percentage inhibition of growth at a concentration of 1 μM. The RAR specific molecules (TTNPB and Am580) exert a stronger inhibiting effect than the natural ligands (all-trans RA and 9-cis RA) and than LGD1069 (RXR agonist). These results confirm those reported by Dawson et al., cancer Res., 1995, 55, 446–451, which have shown that RARα agonists are effective inhibitors of the growth of MCF-7 cells and that the affinity of retinoids for RARα is closely correlated to their anti-proliferation activity. At a concentration of $10^{-8}$ M, LGD1069 is RARα specific and exerts no effect whatsoever on the growth of MCF-7 and T-47D cells in oestrogenic conditions.

TABLE 14

| ANTI-PROLIFERATION EFFECT | | |
|---|---|---|
| Product | T-47D IC$_{50}$ (nM) | MCF-7 IC$_{50}$ (nM) |
| all trans RA | 39.1 | 14.1 +/− 10.3 |
| 9-cis RA | 25.1 +/− 1.4 | not determined |
| Am580 | 74% | 67% |
| TTNPB | 3.3 +/− 1.1 | 0.35 +/− 0.07 |
| LGD1069 | 20% | 33% |

Certain properties of the retinoids have been determined using more developed cellular models. These models consist of cellular lineages transfected in a stable fashion by recombinant plasmids which place the expression of the gene of the luciferase under the control of different nuclear response elements. The observed effects then correspond to physiological regulations and to an activity of endogenic receptors. The tests carried out in duplicate are described below for each of these models.

4) Transactivating Activity of Reference Retinoids Mediated by the Receptors of Retinoic Acid—Cellular Lineages HRLN and HRL+N Transfected in a Stable Fashion The cellular lineages HRLN and HRL+N allow one to study the activation of an RARE by endogenic receptors using ligands at physiological concentrations. These lineages derive from HeLa cells transfected in a stable fashion by a reporter gene which places the expression of the gene of the luciferase under the control of a nuclear response element RARE (RARE$_3$-tk-Luc). The HeLa cells express all the known receptors of the retinoic acid (RARα,β,γ and RXRα,β,γ) with a predominance of RARα and RXRα. The response element RARE used for the HRLN cells corresponds to the sequence of the natural gene of the RARβ receptor (GGTTCAnnnnnAGTTCA). The HRL+N cells comprise the sequence GAGTGAnnnnnCGGTGA.

a) HRLN Lineage

This lineage comprises the response element RARE of the natural gene of the RARβ receptor which controls the expression of the gene of the luciferase. All-trans RA and 9-cis RA induce a dose-dependent activation. An overactivation in comparison to TTNPB is observed at high concentration (1 μM), comparable to that observed with the ERcassette constructions. A co-activation of RAR and of RXR at the level of the hetero-dimer is certainly implied.

The results relating to TTNPB and Am580 indicate the activation induced specifically by the RAR receptors. The $EC_{50}$ values for these two molecules are similar. Am580 induces a transactivation mediated by RARα and TTNPB by RARα,γ as the use of the antagonist RARα Ro 41-5253 shows (Apfel, C. et al., PNAS, USA, 1992, 89, 7129–7133) which totally abolishes the response of Am580 and partially abolishes that of TTNPB. However RARα appears as the predominant receptor for the transactivation in the HeLa cells. The RARα specific ligand LGD1069 transactivates with an $EC_{50}$ of −10 nM, which corresponds to its RXR activity. The HRLN lineage allows clearer evidence to be given of a physiological RAR activity of the compounds, but a weak RXR activity is observed. Table 15 below reports these results where 100% expression corresponds to the induction caused by TTNPB $10^{-8}$ M. The $EC_{50}$ values are determined from results obtained with a range of concentrations going from 1 nM to 1 μM.

TABLE 15

HRLN TRANSACTIVATION

| Product | E max % | $EC_{50}$ (nM) |
|---|---|---|
| all-trans RA | 208 | 2.5 +/− 4 |
| 9-cis RA | 196 | not determined |
| Am580 | 104 | 0.10 +/− 0.06 |
| TTNPB | 100 | 0.55 +/− 0.72 |
| LGD1069 | 73 | 9.4 +/− 6.3 |
| LGD-CB14499 | 30 | not determined | b) HRL+N Lineage

The transactivation results obtained with the HRL+N lineage are comparable to those obtained with the HRLN lineage for the RAR agonist molecules (TTNPB and Am580) and the natural ligands (all-trans RA and 9-cis RA). The RXR agonists (LGD1069 and LGD-CB14499) induce a stronger transactivation with the HRL+N cells and LGD1069 1 μM is more effective than the RAR specific molecules. Furthermore, the association of an RAR agonist and an RXR agonist (for example TTNPB+LGD-CB14499, FIG. 1 in the Appendix) permits a better transactivation than that brought about by either molecule used separately. The HRL+N lineage allows one to visualise a co-activation of the RAR and RXR receptors at the level of the RAR-RXR hetero-dimer. Hence, LGD1069 1 μM having a RAR activity at this concentration behaves as a panagonistic molecule. This result is to be correlated to the over-activation induced by the RXR agonist molecules with the RAR-ERcassettes. The HRL+N lineage allows clear evidence to be given of an RAR and RXR activity of the molecules. These results are reported in Table 16 below where the transcriptional activity of the products is expressed as a percentage, 100% corresponding to the level of activity measured in the presence of TTNPB $10^{-8}$ M.

TABLE 16

HRL+N TRANSACTIVATION

| Product ($10^{-6}$ M) | Emax (%) |
|---|---|
| All-trans RA | 225 |
| Am580 | 99 |
| TTNPB ($10^{-8}$ M) | 100 |
| LGD1069 | 131 |
| LCD-CB14499 | 94 |

FIG. 1 in the Appendix shows the over-activation induced by a RXR selective molecule in the presence of an RAR specific agonist on the HRL+N model.

5) Anti-AP-1 Effect of Reference Retinoids on Oestrogen-dependent Cells Activated by TPA—MTLN Cellular Lineage The anti-factor AP-1 transrepressor effect of retinoids is determined using the MTLN lineage, coming from MCF-7 cells transfected in a stable fashion by a vector p(TRE)$_3$-tk-Luc which places the expression of the gene of luciferase under the control of TPA (12-O-tetradecanoyl-phorbol-13-acetate). TPA activates the AP-1 complex formed from proteins of the family of nuclear proto-oncogenes (c-Jun and c-Fos). This MTLN lineage permits the study of the relationship existing between the oestrogenic routes and AP-1 (M. E. Astruc et al., Endocrinology, 1995, 136, 824–832), and to show the dissociation between the transactivator activity and the anti-AP-1 effect of synthesis retinoids (J. Y. Chen et al., EMBO J., 1995, 14, 1187–1197). The experiments are made with the MTLN cells activated by $10^{-7}$ M TPA.

The results reported in Table 17 below show that the 3 types of retinoic acid receptors expressed by the MCF-7 cells (RARα,γ and RXRα) mediate an inhibitor effect of the AP-1 route. The use of the selective RARE antagonist Ro 41-5253 does not allow the inhibition induced by TTNPB to be totally lifted, which indicates that the activation of RARγ mediates an anti-AP-1 effect. The activation by an RARα agonist (Am580 10 nM) or RXRα (LGD1069 and LGD-CB14499) also causes an inhibition of the AP-1 route. The association of an RAR specific molecule and an RXR specific molecule provokes a strong ant-AP-1 inhibiting effect, there is an additive effect between the to inhibition routes. From its panagonistic profile at 1 μM, LGD1069 appears as the most effective compound tested in this model.

TABLE 17

ANTI-AP-1 EFFECT

| Product | Concentration (Log M) | Inhibition (%) |
|---|---|---|
| All-trans RA | −8 | 22–33 |
|  | −7 | 28–44 |
| 9-cis RA | −8 | 30–37 |
| Am580 | −8 | 40–46 |
|  | −7 | 41–48 |
| TTNPB | −8 | 26–53 |
|  | −7 | 29–54 |

TABLE 17-continued

ANTI-AP-1 EFFECT

| Product | Concentration (Log M) | Inhibition (%) |
|---|---|---|
| LGD1069 | −8 | 18–29 |
|  | −7 | 48–62 |
| LGD-CB14499 | −7 | 17–30 |

The effect of the compounds on the MTLN cells activated by $10^{-7}$ M TPA is expressed as a percentage. 100% represents the maximum level of activity measured with TPA which is 5 to 6 times greater than the base activity of the cells. The inhibitive properties of the products are calculated after deduction of the base activity of the cells. The percentages reported correspond to a range of inhibitions determined from several experiments.

Figure 2:
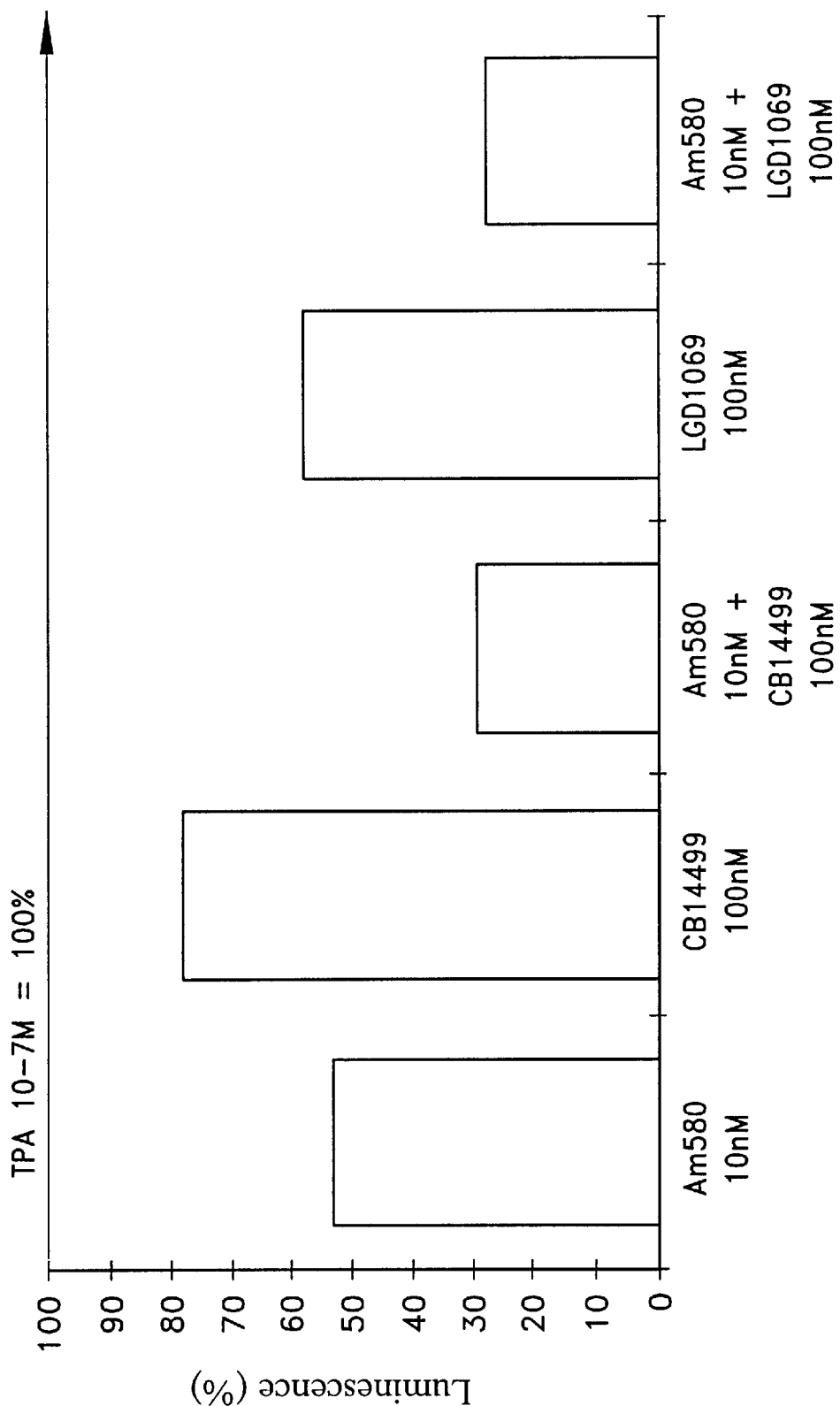
FIG. 2 shows the additive nature of the anti-AP-1 inhibitor effect on the MTLN lineage of an RXR agonist and a selective RAR agonist.

FIG. 2 in the Appendix shows the additive nature of the anti-AP-1 inhibitor effect on the MTLN lineage of an RXR agonist and a selective RAR agonist.

6) Anti-oestrogenic Effect of the Reference Retinoids on the Oestrogen-dependent Cells Activated by Estradiol—MELN Lineage MCF-7 cells express RARα,γ and RXRα. The transfection of MCF-7 cells by an oestrogen-dependent gene (ERE-βGlob-Luc) has permitted the establishment of the MELN cellular lineage, used to determine the anti-oestrogenic activity of the retinoids. These cells contain the gene of the luciferase under the transcriptional control of the promoter of the βGlobine and of the response element ERE isolated from the gene of chicken vitelogenine A2. The experiments are carried out with MELN cells activated by $10^{-9}$ M estradiol. The level of base activity of the MELN cells is obtained with the anti-oestrogen 1 μM 4-OH-tamoxifen (hydroxytamoxifen). This level is always from 8 to 10 times lower than the maximum reference activity measured in the presence of $10^{-9}$ M estradiol which represents 100%. All-trans RA reduces the cellular growth and the expression of oestrogen-dependent genes (E. Demirpence et al., Cancer Res., 1994, 54, 1458–1464), which this MELN lineage allows one to verify.

The RAR selective molecules (Am580 and TTNPB) induce an inhibition of the order of 40%. Am580 at a specific RARα concentration (10 nM) permits maximum inhibition, which indicates that RARα mediates the anti-oestrogenic effect in the MCF-7 cells. The use of the RAR( antagonist Ro 41-5253 raises the inhibitor effect of Am580 and also of TTNPB which, under these conditions, preserves an RARγ activity and loses its RARα activity. The RXR selective compounds (LGD1069 and LGD-CB14499) are inactive. The activation of RXR is therefore not implied in the inhibition of the oestrogenic route by the retinoids in the MCF-7 cells.

These results are reported in Table 18 below, they are perfectly correlated with oestrogen-induced cellular proliferation experiments. The association of an RAR specific agonist and an RXR specific agonist does not allow one to observe an inhibitor effect greater than that exerted by the RAR agonist alone.

TABLE 18

ANTI-OESTROGENIC EFFECT

| Product | Concentration (Log M) | Inhibition (%) |
|---|---|---|
| All-trans RA | −7 | 35 |
| 9-cis RA | −7 | 35 |
| Am580 | −8 | 36–51 |
| TTNPB | −8 | 30–41 |
| LGD1069 | −8 | 0 |
|  | −7 | 0 |
| LGD-CB14499 | −7 | 0 |
|  | −6 | 0 |

The effect of the products tested on the cells activated by $10^{-9}$ M estradiol is expressed as a percentage, the level of base activity being deducted.

6) Conclusion

The reference molecules have allowed one to show the effectiveness and the complementary nature of the different models used and lead to the following conclusions:

chimerical constructions GAL-RAR and RAR-ERcassette allow the determination of the RAR agonist profile of molecules, but also an RXR agonist activity with RAR-ERcassette, the HRLN lineage mainly conveys the activity of a compound mediated by endogenic RARα, the HRL+N lineage also provides evidence of an RXR agonist activity of the retinoids, the anti-oestrogenic effect of the retinoids (oestrogen-induced cellular proliferation and MELN lineage) is mediated by RARα, the anti-AP-1 effect is mediated in the MCF-7 cells (MTLN lineage) by RARα, RARγ and RXRα, and an additive effect exists between the RAR and RXR routes.

B) Activities of the Derivatives of the Retinoid Type of Trans Series (E)

The results obtained with the molecules of the series (E) are to be compared with those shown by the reference molecules and for the SRI3946 molecule (CB24159). This compound is RAR selective.

1) Specificity of the Derivatives Tested

The RAR agonist activity of compounds of the series (E) has been evaluated with the RAR-ERcassette model. At a concentration of 1 μM, the molecules of the invention of this series permit a transactivation mediated by the three types of RAR receptors. Their activity is reported in Table 19 below and, at this concentration, appears comparable to that of TTNPB.

TABLE 19

| | | RAR-ERcassettes | | |
|---|---|---|---|---|
| Product | Concentration (Log M) | RARα (%) | RARβ (%) | RARγ (%) |
| TTNPB | −8 | 100 | 100 | 100 |
| CB24159 | −6 | 113 | 117 | 89 |
| CB73364 | −6 | 74 | 118 | 78 |
| CB12273 | −6 | 90 | 123 | 106 |
| CB57201 | −6 | 73 | 132 | 84 |

2) Effect of the Derivatives of the Trans Series (E) on Oestrogen-induced Proliferation—Cellular Lineages MCF-7 and T-47D Table 20 below reports the effect of the retinoids on the growth of MCF-7 and T-47D cells which is evaluated after 7 days of culture in the presence of $10^{-9}$ M estradiol by dosing the cellular DNA. The CB24159 molecule inhibits the growth of the T-47D cells in a dose dependent manner with an efficacy greater than that of TTNPB. CB73364 exerts an effect comparable to TTNPB. The other molecules induce an inhibition of the order of 50% at the concentration of 0.3 μM which corresponds to their observed RARα activity in specificity at this concentration (cf. RAR-ERcassette model).

TABLE 20

ANTI-PROLIFERATIVE EFFECT

| Product | Concentration (Log M) | T-47D |
|---|---|---|
| CB24159 | | 1.4 +/- 0.2 |
| CB73364 | | 4.1 +/- 0.7 |
| CB71802 | -6 | 72% |
| CB12273 | | 252.8 +/- 109.7 |
| CB57201 | | 233.0 +/- 90.6 |
| CB38973 | -6 | 55% |

3) Transactivating Activity of the Trans Derivatives (E) Mediated by the Retinoic Acid Receptors—HRLN Cellular Lineages As indicated in Table 21 below, the structural modifications carried out on the molecules of the trans series (E) cause a diminution of the high efficacy of this molecules in transactivation. However at 1 μM, they permit induction comparable to that of TTNPB and CB24159. This activity corresponds to the RAR profile of these molecules determined with the RAR-ERcassette model.

TABLE 21

HRLN TRANSACTIVATION

| Product | E max % | $EC_{50}$ (nM) |
|---|---|---|
| TTNPB | 100 | 0.55 +/- .072 |
| CB24159 | 100 | 0.08 +/- 0.10 |
| CB73364 | 89 | 33 |
| CB71802 | 76 | 31.4 +/- 16.9 |
| CB12273 | 106 | 21.4 +/- 5.6 |
| CB57201 | 70 | 55.8 +/- 70.1 |
| CB80660 | 106 | 38.3 +/- 9.5 |
| CB38973 | 89 | 14.9 +/- 12.3 |

4) Anti-oestrogenic Effect of the Trans (E) Derivatives on Oestrogen-dependent Cells Activated by Estradiol—MELN Lineage As indicated in Table 22 below, the CB24159 derivative is the compound that is the most inhibiting of the oestrogenic transcription on the MELN model. Its activity is perfectly correlated with its transcriptional properties mediated by RAR in the HRLN lineage. As for CB24159, the maximum inhibition brought about by the trans (E) molecules is of the order of 30 to 40%. The anti-oestrogenic effect of the retinoids being mediated by RARα in the MCF-7 cells, these compounds exert their inhibition through this receptor, which corresponds to their RARα mediated transcriptional power (cf. HRLN models and RARα-ERcassette).

TABLE 22

ANTI-OESTROGENIC EFFECT

| Product | Concentration (Log M) | Inhibition (%) |
|---|---|---|
| CB24159 | -8 | 31-43 |
| | -7 | 26-43 |
| | -6 | 22-37 |
| CB73364 | -8 | 13 |
| | -7 | 24 |
| | -6 | 20-41 |
| CB71802 | -8 | 5 |
| | -7 | 37 |
| | -6 | 32-48 |
| CB12273 | -8 | 0 |
| | -7 | 7-16 |
| | -6 | 21-41 |
| CB57201 | -8 | 0 |
| | -7 | 1-9 |
| | -6 | 23-41 |
| CB38973 | -6 | 30 |
| CB80660 | -8 | 26 |
| | -7 | 20-42 |
| | -6 | 18-37 |

C) Activities of the Derivatives of the Retinoid Type of the Invention of the cis-series (Z)

These derivatives divide into two families:
carboxylated molecules (substituent $R_1$),
molecules where the carboxyl group is replaced by a tetrazole group.

1) Specificity of the cis Derivatives (Z)

The two types of construction (Gal-RAR and RAR-ERcassette) have been used to provide evidence of the interest of this series.

a) Chimerical Receptors Gal14-RAR

The Gal-RAR constructions have allowed the evaluation of the RAR agonist activity of the derivatives of the cis series (Z). The results reported in Table 23 below show that the reference molecule SRI (CB28628) is completely agonistic for the three types of RAR receptors and permits the same maximum transactivation as TTNPB (selective RAR agonist). The molecules derived from CB28628 appear less effective. The carboxylated molecules (CB36493 and CB16279) are partial agonists at 1 μM for the three RAR receptors while CB38416 is a partial agonist for RARα and RARβ but complete for RARγ. These molecules have the property of inducing an RAR mediated transactivation. The compounds that include a tetrazole group (CB92834 and CB77402) are incapable of transactivating by means of RAR receptors. They are not RAR agonists.

TABLE 23

GAL-RAR

| Product | Concentration (Log M) | RARα (%) | RARβ (%) | RARγ (%) |
|---|---|---|---|---|
| TTNPB | -8 | 100 | 100 | 100 |
| SRI (CB28628) | -7 | 103 | 102 | 106 |
| CB38416 | -6 | 58 | 51 | 99 |
| CB36493 | -6 | 38 | 44 | 50 |
| CB16279 | -6 | 33 | 47 | 59 |
| CB92834 | -6 | 8 | 0 | 2 |
| CB77402 | -6 | 6 | 0 | 0 | b) Chimerical Receptors ERcassettes

As reported in table 24 below, the profile defined with the RAR-ERcassette model for the cis derivatives (Z) differs from the Gal-RAR profile. 10 nM TTNPB shows the maximum transactivation induced by a selective synthetic RAR agonist. SRI (CB28628) is a complete agonist for RARγ-ERcassette and induce an over-activation of RARα-ERcassette and RARβ-ERcassette at 1 μM. This over-activation conveys panagonistic properties (RXR and RAR agonist). The carboxylated compounds (CB30382, CB38416, CB36493 and CB16279) induce a transactivation mediated by the three receptors. An over-activation of RARβ-ERcassette intervenes with these molecules, which conveys an RXR activity. The carboxylated cis derivatives (Z) are also panagonistic. The molecules that include a tetrazole group (CB92834 and CB77402) do not permit transactivation mediated by RARα-ERcassette and RARγ-cassette. However, a partial transactivation of RARβ-ERcassette is observed. Insofar as these compounds are inactive on Gal-RARβ, this partial agonistic effect can be attributed to an RXR activity. Furthermore, the association of CB92834 or CB77402 with a specific RAR agonist permits an over-activation of the effect of the RAR molecule alone for the three RAR-ERcassette receptors, which tends to confirm the RXR agonist activity of CB92834 and CB77402.

TABLE 24

RAR-ERcassettes

| Product | Concentration (Log M) | RARα (%) | RARβ (%) | RARγ (%) |
|---|---|---|---|---|
| TTNPB | −8 | 100 | 100 | 100 |
| SRI (CB28628) | −8 | 35 | 88 | 55 |
|  | −7 | 95 | 115 | 87 |
|  | −6 | 179 | 183 | 92 |
| CB30382 | −7 | 12 | 39 | 29 |
|  | −6 | 93 | 130 | 83 |
| CB38416 | −8 | 0 | 10 | 4 |
|  | −7 | 7 | 57 | 14 |
|  | −6 | 65 | 198 | 62 |
| CB36493 | −8 | 1 | 0 | 0 |
|  | −7 | 15 | 34 | 5 |
|  | −6 | 91 | 205 | 26 |
| CB16279 | −7 | 6 | 60 | 15 |
|  | −6 | 60 | 118 | 71 |
| CB92834 | −8 | 0 | 0 | 2 |
|  | −7 | 9 | 36 | 7 |
|  | −6 | 11 | 43 | 0 |
| CB77402 | −8 | 0 | 0 | 0 |
|  | −7 | 1 | 31 | 0 |
|  | −6 | 8 | 37 | 8 |

2) Effect of the Molecules of the cis Series (Z) on the Oestrogen-induced Proliferation—Cellular Lineages MCF-7 and T-47D Table 25 below reports the effect of the cis derivatives (Z) on the growth of T-47D cells which is evaluated after 7 days of culture in the presence of $10^{-9}$ M estradiol through dosing of the cellular DNA. The carboxylated molecules induce an inhibition of the order of 20 to 50% which corresponds to their partial RARα agonist profile determined in transitory transfections (Gal-RAR and RAR-ERcassette). SRI (CB28628), a complete agonist, allows an inhibition of the order of 70%, comparable to that exerted by Am580. CB92834 is inactive on the oestrogen-induced growth.

TABLE 25

T-47D ANTIPROLIFERATIVE EFFECT

| PRODUCT | Concentration (Log M) | Growth 100% = E2 $10^{-9}$ M |
|---|---|---|
| SRI (CB28628) | −6 | 33 |
| CB36493 | −6 | 68–78 |
| CB30382 | −6 | 73–94 |
| CB38416 | −6 | 50–60 |
| CB16279 | −6 | 84 |
| CB92834 | −6 | 94 |

3) Transactivator Activity of the cis Derivatives (Z) Mediated by the Retinoic Acid Receptors—HRLN and HRL+N Cellular Lineages a) HRLN Lineage The RAR agonist activity of the carboxylated cis derivatives (Z) (CB38416, CB30382, CB36493 and CB16279) observed with the chimerical models is confirmed with the HRLN model, as reported in Table 26 below. At 1 μM, these compounds induce a transactivation close to that of TTNPB. However, the structural modifications carried out on these derivatives bring about, in comparison with the reference SRI (CB28628) a diminution of affinity, and therefore of RAR mediated effectiveness. The compounds that include a tetrazole group (CB92834 and CB77402) are very feebly active, which corresponds to their activity in RAR-ERcassette.

TABLE 26

HRLN TRANSACTIVATION

| Product | E max % |
|---|---|
| TTNPB | 100 |
| SRI (CB28628) | 98 |
| CB30382 | 102 |
| CB38416 | 81 |
| CB36493 | 97 |
| CB92834 | 21 |
| CB77402 | 18 | b) HRL+N Lineage

The HRL+N lineage allows evidence to be provided of an RXR agonist activity. The results reported in Table 27 below are correlated with those obtained with the RAR-ERcassette model. SRI (CB28628) is a panagonistic molecule. It induces a transactivation maximum greater than that of TTNPB. The carboxylated compounds of the cis series (Z) (CB38416, CB16279) appear as panagonistic compounds, in agreement with the results observed in RAR-ERcassette, and bring about a transactivation greater than RAR selective agonists (TTNPB). The non-cyclic CB (Z) molecules that include a tetrazole group (CB92834, CB77402) allow the observation of a weak transactivation, less than that of TTNPB. The association of CB92834 or CB77402 with a specific RAR agonist induces a stronger transactivation than that observed for each compound tested separately, which corresponds to the RXR agonist profile of CB92834 and CB77402.

TABLE 27

HRL+N TRANSACTIVATION

| Product | E max % |
| --- | --- |
| TTNPB | 100 |
| SRI (CB28628) | 158 |
| CB38416 | 131 |
| CB92834 | 42 |
| CB77402 | 33 |

Figure 3:
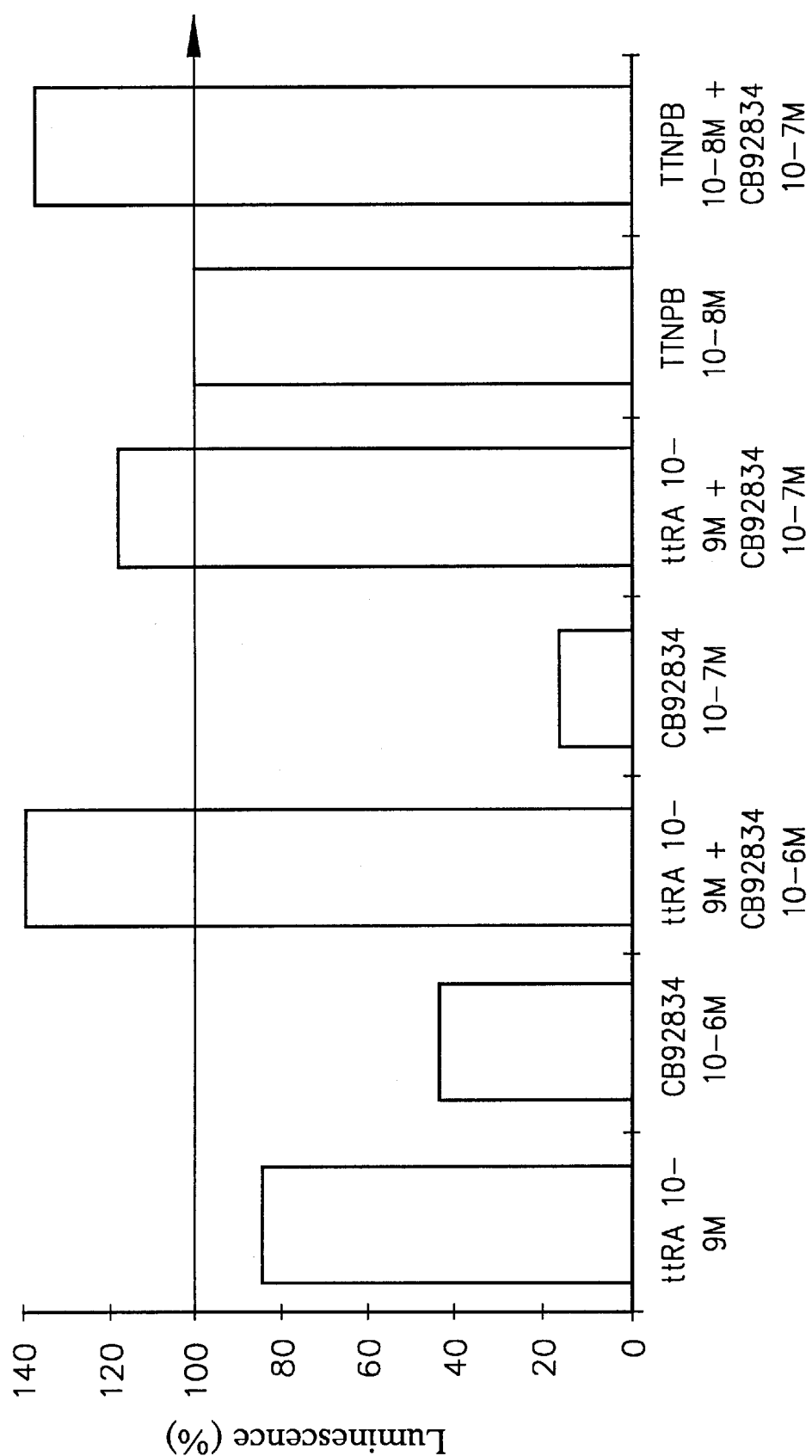
FIG. 3 represents the over-activation by CB92834 of the transactivation induced by a selective RAR agonist on the HRL+N lineage.

FIG. 3 in the Appendix represents the over-activation by CB92834 of the transactivation induced by a selective RAR agonist on the HRL+N lineage.

4) Anti-AP-1 Effect of the cis Derivatives (Z) on Oestrogen-dependent Cells Activated by TPA—MTLN Cellular Lineage The MTLN lineage activated by TPA allows one to study the effect of cis derivatives (Z) on the AP-1 route. The interpretation of the results reported in Table 28 below is based on the conclusions made from effects observed with the reference molecules. The RARα, RARγ and RXRα activations mediate an anti-AP-1 effect in the MCF-7 cells and there is an additivity of the RAR and RXR effects. CB28628 exhibits a strong anti-AP-1 effect on the MCF-7 cells. Like LGD1069, this molecule exerts a strong inhibition from its panagonistic properties. All the molecules of the (Z) series exhibit an inhibitor profile of the AP-1 route. The carboxylated compounds (CB36493 and CB30382) at the concentration of 1 μM exert an inhibitor effect comparable to that of the effect of CB28628. These panagonistic derivatives (cf. RAR-ERcassettes and HRL+N results) induce an anti-AP-1 effect by activation of the RAR and RXR receptors. CB92834 and CB77402 also show an inhibitor profile. The measured inhibition is of the order of 20 to 30%, comparable to that observed for $10^{-8}$ M LGD1069 (RXR selective at this concentration). CB92834 and CB77402 are anti-AP-1 molecules through RXR. In association with a selective RAR agonist, one observes an anti-AP-1 additive effect. These two compounds therefore show the advantage of exerting a transrepression of the AP-1 route without inducing an activation of the transcription of a controlled gene by an RARE.

TABLE 28

ANTI-AP-1 EFFECT MTLN

| Product | Concentration (Log M) | Inhibition (%) |
| --- | --- | --- |
| TTNPB | −8 | 26–53 |
| CB28628 | −7 | 40 |
|  | −6 | 58 |
| CB30382 | −7 | 21 |
|  | −6 | 42–47 |
| CB38416 | −7 | 7–14 |
|  | −6 | 21–25 |
| CB36493 | −7 | 26 |
|  | −6 | 38–46 |
| CB16279 | −6 | 23–26 |
| CB92834 | −7 | 4–9 |
|  | −6 | 20–23 |
| CB77402 | −7 | 21–23 |
|  | −6 | 30–33 |

Figure 4:
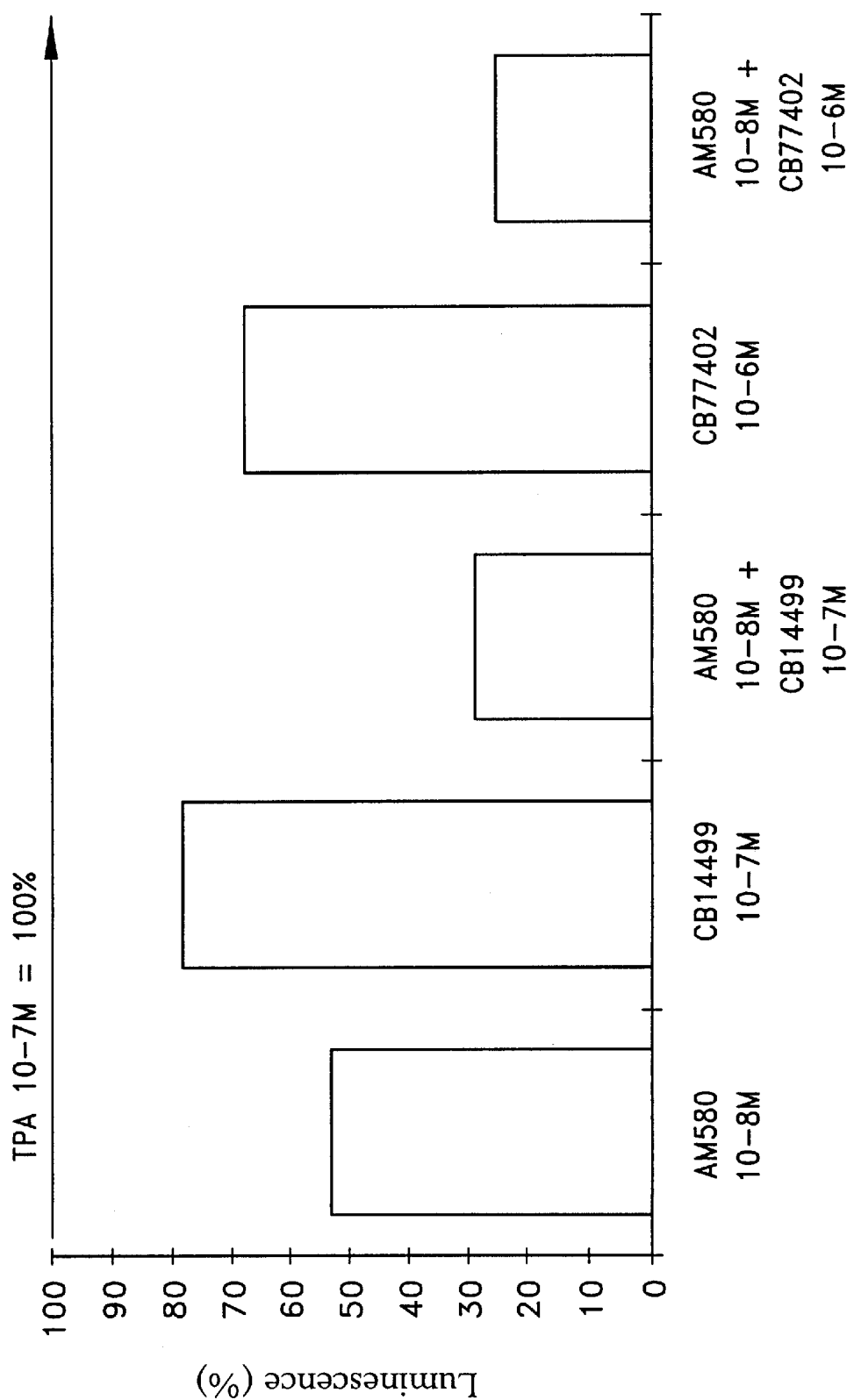
FIG. 4 shows the additive nature of the anti-AP-1 inhibitor effect on the MTLN lineage of CB77402 and of Am580.

FIG. 4 shows the additive nature of the anti-AP-1 inhibitor effect on the MTLN lineage of CB77402 and of Am580.

5) Anti-oestrogenic Effect of the cis Derivatives (Z) on the Oestrogen-dependent Cells Activated by Estradiol—MELN Lineage The use of reference molecules has allowed one to show that the anti-oestrogenic effect of retinoids is mediated by RARα. The anti-oestrogenic action of the cis derivatives (Z) evaluated with the MELN lineage, activated by $10^{-9}$ M estradiol, follows their RARα profile. As reported in Table 29 below, these carboxylated derivatives (CB36493, CB38416, CB30382 and CB16279), partially agonistic, permit a transrepression of a controlled gene by an ERE. CB92834 and CB77402 are inactive, which is in perfect agreement with their incapacity to be RARα activated.

TABLE 29

ANTI-OESTROGENIC EFFECT MELN

| Product | Concentration (Log M) | Inhibition (%) |
| --- | --- | --- |
| TTNPB | −8 | 30–41 |
| SRI (CB28628) | −7 | 31 |
|  | −6 | 29–41 |
| CB30382 | −7 | 0 |
|  | −6 | 2–20 |
| CB38416 | −7 | 0 |
|  | −6 | 19 |
| CB36493 | −7 | 0 |
|  | −6 | 17–32 |
| CB73069 | −6 | 17–21 |
| CB16279 | −6 | 32 |
| CB92834 | −6 | 0 |
| CB77402 | −6 | 0 |

6) Conclusion

The derivatives of the invention of the cis series (Z) exhibit very interesting properties. The compounds CB92834 and CB77402 show an RXR specific activity, in comparison with the carboxylated cis molecules (Z) which are panagonistic (CB36493, CB30382, CB38416, CB16279). Hence, the substitution of the carboxyl group by a tetrazole group brings about a loss of RAR activity and allows orientation of these molecules towards an RXR specificity. These compounds exert an inhibitor effect on the AP-1 route and are inactive on the transcription of a gene controlled by a RARE. Their association with an RAR specific molecule allows optimisation of the anti-AP-1 effect of these molecules.

Other characteristics and advantages of the invention will become apparent on reading the examples which follow relating to the preparation and the analysis of reference compounds and derivatives of the invention, it being understood that these examples should not be interpreted as tending to reduce the scope of the claims.

EXAMPLE 1

Preparation of the acid (E) 4-[1-(5,6,7,8-tetrahydro-3,5,5,8,8-pentamethyl-2-naphthalenyl)-2-propenyl] benzoic acid (CB71802) of formula

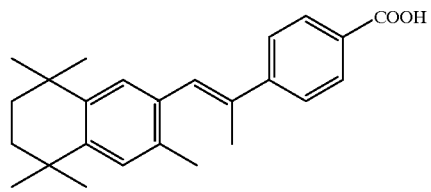

a) Preparation of 2,5-dichloro-2,5-dimethylhexane

Thionyl chloride (25 ml, 341.8 mmol) is added at ambient temperature to a solution of 2,5-dimethyl-2,5-hexanediol (20.0 g, 136.8 mmol) in 250 ml of dichloromethane. The reaction mixture yellows and the agitation is continued for 4 hours. The progress of the reaction is controlled by thin film chromatography (eluent ether: petroleum ether=50:50). At the end of reaction, 250 ml of distilled water is added, it is decanted and the organic phase is neutralised using 2×250 ml of a 10% $NaHCO_3$ solution. The product is dried with $MgSO_4$ filtered and evaporated to dryness. 18.37 g of a solid 2,5-dichloro-2,5-dimethylhexane is obtained (gross yield= 73%).

$NMR^1H$ 200 MHz ($CDCl_3$): 1.57 (s, 12H, Me); 1.92 (s, 4H, —$CH_2$—).

b) Preparation of 1,1,4,4,6,7-hexamethyl-1,2,3,4-tetrahydronaphthalene

Aluminium trichloride (3.0 g, 22.5 mmol) is weighed into a 250 ml three-necked flask fitted with a condenser, a magnetic stirrer and a thermometer. 70 ml of o-xylene (Aldrich) is added and then a solution of 2,5-dichloro-2,5-dimethylhexane (15.00 g, 81.9 mmol) prepared in the previous step, in 30 ml of o-xylene is added with a bromine ampoule. The reaction medium is heated for 3 hours at 100° C., there is a large release of HCl and the reaction mixture becomes dark red. After cooling the reaction medium, it is poured into a water-ice mixture (200 ml). The product is extracted by ether (3×80 ml), washed with a saturated $NaHCO_3$ solution (2×150 ml), the ether phase is dried with $MgSO_4$, filtered and evaporated. The raw product is purified by distillation under vacuum. 15.20 g of a solid 1,1,4,4,6,7-hexamethyl-1,2,3,4-terahydronaphthalene is obtained (yield=86%).

$NMR^1H$ 200 MHz ($CDCl_3$): 1.31 (s, 12H, 1-Me and 4-Me); 1.71 (s, 4H, —$CH_2$—); 2.26 (s, 6H, 6 and 7 Me); 7.11 (s, 2H, ArH).

c) Preparation of 6-bromomethyl-1,1,4,4,7-pentamethyl-1,2,3,4-tetrahydronaphthalene of formula A solution of 1,1,4,4,6,7-hexamethyl-1,2,3,4-terahydronaphthalene (6.91 g, 31.9 mmol), NBS (5.97 g, 33.5 mmol), benzoyl peroxide (0.22 g, 0.9 mmol) in 100 ml of $Ccl_4$ is brought to reflux for 5 hours. The solution is then cooled, concentrated in a rotary evaporator, taken up in ether (100 ml), filtered to remove the succinimide formed (the succinimide being washed with ether) and concentrated. 8.80 g of a raw product is obtained composed ($NMR^1H$ 200 MHz) of about 30% of 1,1,4,4,6,7-hexamethyl-1,2,3,4-tetrahydronaphthalene, about 65% of the 6-bromomethyl-1,1,4,4,7-pentamethyl-1,2,3,4-tetrahydronaphthalene desired and about 5% of a corresponding dibrominated compound. This raw product will be used for the formation of the corresponding phosphonium salt.

$NMR^1H$ 200 MHz ($CDCl_3$) 1.27 (s, 12H, 5,8-$CH_3$); 1.67 (s, 4H, 6,7-$CH_2$—); 2.36 (s, 3H, ArMe); 4.50 (s, 2H, BnzH); 7.05 (s, 1H, ArH ortho Me); 7.22 (s, 1H, ArH meta Me).

d) Preparation of (5,6,7,8-tetrahydro-3,5,5,8,8-pentamethyl-2-naphthalenyl)-methyl triphenylphosphonium bromide of formula The raw 6-bromomethyl-1,1,4,4,7-pentamethyl-1,2,3,4-tetrahydronaphthalene (8.80 g, about 32 mmol) prepared previously is mixed with triphenylphosphine (10.1 g, 38.4 mmol) in solution in 50 ml of dichloromethane for 24 hours, then diluted with ethyl ether (200 ml). The [(5,6,7,8-tetrahydro-3,5,5,8,8-pentamethyl-2-naphthalenyl)-methyl] triphenylphosphonium bromide precipitates, is filtered and washed abundantly with the ether. 10.72 g of white crystals (5,6,7,8-tetrahydro-3,5,5,8,8-pentamethyl-2-naphthalenyl)-methyl-triphenylphosphonium bromide is obtained after drying (yield=60%).

$NMR^1H$ 200 MHz ($CDCl_3$): 0.74 (s, 6H, 5-$CH_3$); 1.15 (s, 6H, 8-$CH_3$); 1.52 (s broad, 2H, 6-$CH_2$); 1.56 (s broad, 2H, 7-$CH_2$); 1.56 (s, 3H, ArMe); 4.98 (d, 2H, —$CH_2$—P J 16.8 Hz); 6.77 (s, 1H, ArH J 2.8 Hz); 6.84 (s, 1H, ArH); 7.78–7.46 (m, 15H, ArH).

e) Preparation of the (E) and (Z) 4-[1-(5,6,7,8-tetrahydro-3,5,5,8,8-pentamethyl-2-naphthalenyl)-2-propenyl] benzonitriles of formulae

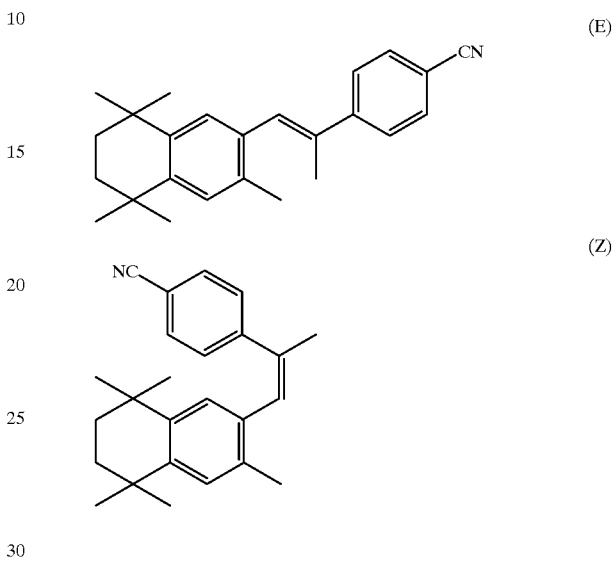

A solution of (5,6,7,8-tetrahydro-3,5,5,8,8-pentamethyl-2-naphthalenyl)-methyl-triphenylphosphonium bromide (3.65 g, 6.5 mmol) prepared previously and NaH (Aldrich, 6.0 mmol) coming from 0.24 g of a dispersion of 60% of NaH in oil in 5 ml of anhydrous DMSO is agitated under argon for 30 minutes, and then a solution of 4-cyanoacetophenone (1.45 g, 10.0 mmol) in 5.5 ml of DMSO is added. The solution is agitated for 6 hours at ambient temperature and then poured over ice (100 g). The product is then extracted with ether (5×100 ml). The raw product is purified by flash chromatography on silica (eluent pure petroleum ether) then purified again by flash chromatography on silica (eluent ether:petroleum ether=1:99) so as to separate the isomers. 0.25 g of a white solid (Z) 4-[1-(5,6,7,8-tetrahydro-3,5,5,8,8-pentamethyl-2-naphthalenyl)-2-propenyl]benzonitrile is obtained (yield=14%) and then 0.20 g of another white solid (E) 4-[1-(5,6,7,8-tetrahydro-3,5,5,8,8-pentamethyl- 2-naphthalenyl)-2-propenyl]benzonitrile (yield=11%) and 0.18 g of a mixture of the two isomers (yield=10%).

Isomer (E)

$NMR^1H$ 200 MHz ($CDCl_3$): 1.28 (s, 12H, 5,8-$CH_3$); 1.68 (s, 4H, 6,7-$CH_2$—); 2.16 (d, 3H, vinyl Me J 0.8 Hz); 2.24 (s, 3H, ArMe); 6.91 (s broad, 1H, vinyl H); 7.13 (s, 1H, ArH); 7.16 (s, 1H, ArH); 7.62 (s, 2H, ArH meta to the CN); 7.63 (s, 2H, ArH ortho to the CN).

Isomer (Z)

$NMR^1H$ 200 MHz ($CDCl_3$): 0.78 (s, 6H, 5-Me); 1.20 (s, 6H, 5,8-Me); 1.40–1.60 (m, 4H, 6.7-$CH_2$); 2.21 (d, 3H, vinyl Me J 1.5 Hz); 2.25 (s, 3H, ArMe); 6.51 (s, 1H, ArH); 6.59 (s broad, 1H, vinyl H); 7.00 (s, 1H, ArH); 7.19 (d, 2H, ArH meta to the CN J 8.4 Hz); 7.46 (d, 2H, ArH ortho to the CN J 8.4 Hz).

f) Preparation of the acid (E) 4-[1-(5,6,7,8-tetrahydro-3,5,5,8,8-pentamethyl-2-naphthalenyl)-2-propenyl]benzoic acid (compound CB71802) of formula

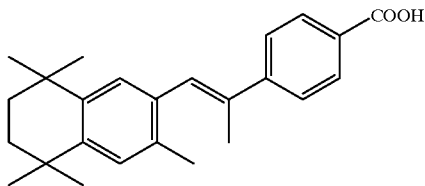

A suspension of the derivative (E) 4-[1-(5,6,7,8-tetrahydro-3,5,5,8,8-pentamethyl-2-naphthalenyl)-2-propenyl]benzonitrile (0.22 g, 0.64 mmol) prepared previously in alcoholic potassium hydroxide (0.94 g, 16.8 mmol KOH in 0.55 ml $H_2O$ and 3.3 ml EtOH) is heated to 70° C. under magnetic stirring for 6 hours. The progress of the reaction is followed by HPLC. After cooling of the reaction medium, it is taken up in water (50 ml), acidified by 1N HCl, extracted with ether (4×20 ml) and the ether phase dried with $MgSO_4$, filtered and evaporated to obtain a raw product which is purified by washing with hexane. After drying at 50° C. (3 hours) in a desiccator under vacuum, 0.18 g of a whitish product, the acid (E) pure 4-[1-(5,6,7,8-tetrahydro-3,5,5,8,8-pentamethyl-2-naphthalenyl)-2-propenyl]benzoic acid is obtained (yield=75%).

m. pt. (° C.)=209–210 (dec.)

NMR$^1$H 200 MHz (CDCl$_3$): 1.29 (s, 12H, 5,8-CH$_3$); 1.69 (s, 4H, 6,7-CH$_2$); 2.19 (d, 3H, vinyl Me J 1.1 Hz); 2.26 (s, 3H, ArMe); 6.95 (s broad, 1H, vinyl H); 7.13 (s, 1H, ArH); 7.19 (s, 1H, ArH); 7.63 (d, 2H, ArH meta to the COOH J 8.4 Hz); 8.11 (d, 2H, ArH ortho to the COOH J 8.4 Hz).

MS EI 70 eV (m/z, % intensity): 362 (M$^+$, 79%); 347 (M$^+$—CH$_3$, 100).

HRMS EI 70 eV: M$_{tr}$=362.2220 for C$_{25}$H$_{30}$O$_2$ M$_{th}$= 362.2246

HPLC: ODS column, Ultrasphere, 5μ, 250×4.6 mm, detector Shimadzu UV, 260 nm, flow rate 1 ml/min, eluent MeOH:H$_2$O=90:10+0.1% TFA, acid (compound CB71802) tr=11.4 min 99.0%; impurities tr=8.0 min 0.5% and tr=9.0 min 0.3%.

IR (pure, cm$^{-1}$): 3400–2500; 2958; 1688, 1604, 1420, 1288, 1186, 1124, 1066, 1016, 908, 850.

EXAMPLE 2

Preparation of the acid (Z) 4-[1-(5,6,7,8-tetrahydro-3,5,5,8,8-pentamethyl-2-naphthalenyl)-2-propenyl] benzoic acid (compound CB32706) of formula

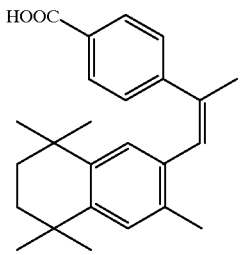

A suspension of the derivative (Z) 4-[1-(5,6,7,8-tetrahydro-3,5,5,8,8-pentamethyl-2-naphthalenyl)-2-propenyl]benzonitrile (30 mg, 0.08 mmol) prepared previously in alcoholic potassium hydroxide (0.21 g, 3.84 KOH in 0.11 ml H$_2$O and 0.7 ml EtOH) is heated to reflux under magnetic stirring for 6 hours. The ethanol is evaporated in a rotating evaporator. The product is taken up in water (20 ml), acidified by 1N HCl, extracted with ether (5×40 ml) and the ether phase dried over MgSO$_4$, filtered and evaporated. The product is recrystallised in hexane, filtered and dried. 110 mg of a white solid, the acid (Z) pure 4-[1-(5,6,7,8-tetrahydro-3,5,5,8,8-pentamethyl-2-naphthalenyl)-2-propenyl]benzoic acid (compound CB32706) is obtained (yield=95%)

m. pt. (° C.)=185.

NMR$^1$H 200 MHz (CDCl$_3$): 0.76 (s, 6H, 2 Me); 1.20 (s, 6H, 2 Me); 1.40–1.60 (m, 4H, 2 —CH$_2$—); 2.23 (d, 3H, vinyl Me J 1.3 Hz); 2.25 (s, 3H, Me); 6.57 (s, 2H, ArH); 6.99 (s, 1H, vinyl H); 7.20–7.30 (m, 2H, ArH); 7.90 (d, 2H, J 8 Hz).

MS EI 70 eV (m/z, % intensity): 362 (M$^+$, 69.5%); 347 (100); 149 (13).

HPLC: ODS column, Ultrasphere, 5μ, 250×4.6 mm, detector Shimadzu UV, 260 nm, flow rate 1 ml/min, eluent: MeOH:H$_2$O=90:10+0.1% TFA, flow rate 1 ml/min, acid (compound CB32706) tr=12.1 min 99.2%; impurities tr=8.0 min 0.5% and tr=9.0 min 0.3%.

IR (cm$^{-1}$): 2926; 1688, 1606, 1418, 1280.

EXAMPLE 3

Preparation of the compound (E) 5-[4-[1-(5,6,7,8-tetrahydro-3,5,5,8,8-pentamethyl-2-naphthalenyl)-2-propenyl]phenyl]-1H-tetrazole (compound CB40747) of formula

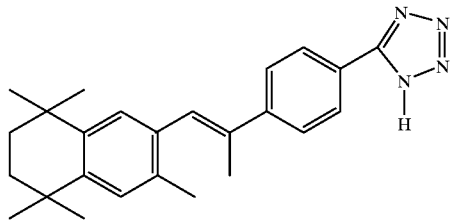

Dibutyl tin oxide (23 mg, 10% mol) and trimethylsilyl azide (0.247 ml, 1.86 mmol, 2 eq.) are added successively to a solution of the (E) and (Z) 4-[1-(5,6,7,8-tetrahydro-3,5,5,8,8-pentamethyl-2-naphthalenyl)-2-propenyl]benzonitriles (0.32 g, 0.93 mmol) previously prepared in anhydrous toluene (5 ml). The reaction medium is heated for 16 hours at reflux (110° C.) under an atmosphere of argon and with magnetic stirring. The product is precipitated with rectified chloroform in order to obtain, after filtration, 31 mg of a white solid the pure compound (E) 5-[4-[1-(5,6,7,8-tetrahydro-3,5,5,8,8-pentamethyl-2-naphthalenyl)-2-propenyl]phenyl]-1H-tetrazole (compound CB40747) after drying in a desiccator under vacuum (with P$_2$O$_5$).

m. pt. (° C.)=256–258 (dec.)

NMR$^1$H 200 MHz (DMSO-D$_6$): 1.24 (s, 12H, 5 and 8-Me); 1.64 (s, 4H, —CH$_2$—); 2.15 (d, 3H, Me J 0.7 Hz); 2.21 (s, 3H, Me); 7.02 (s, 1H, vinyl H); 7.16 (s, 2H, ArH); 7.81 (d, 2H, ArH meta to the tetrazyl J 8.4 Hz); 8.05 (d, 2H, ArH ortho to the tetrazoyl J 8.4 Hz) H$_2$O peak at 3.30; DMSO peak 2.48.

MS EI 70 eV (m/z, % intensity): 386 (M$^+$, 100%); 371 (29), 359 (21), 358 (71), 343 (25), 328 (11), 327 (19) 312 (17).

HRMS EI 70 eV: M$_{tr}$=386.2450 for C$_{25}$H$_{30}$N$_4$ M$_{th}$= 386.2470

HPLC: ODS column, Ultrasphere, 5μ, 250×4.6 mm, detector Shimadzu UV, 260 nm, eluent MeOH:H$_2$O=90:10+ 0.1% TFA, flow rate 1 ml/min, tetrazole (compound CB40747) tr=9.10 min 97.9%; impurity tr=6.75 min 1.53%.

EXAMPLE 4

Preparation of the compound (Z) 5-[4-[1-(5,6,7,8-tetrahydro-3,5,5,8,8-pentamethyl-2-naphthalenyl)-2-propenyl]phenyl]-1H-tetrazole (compound CB61692) of formula

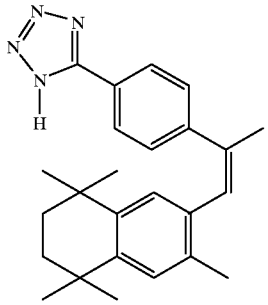

Dibutyl tin oxide (22.3 mg, 0.09 mmol, 10% mol) and trimethylsilyl azide (0.19 ml, 1.40 mmol), are added successively to a solution of the previous (Z) 4-[1-(5,6,7,8-tetrahydro-3,5,5,8,8-pentamethyl-2-naphthalenyl)-2-propenyl]benzonitrile (0.24 g, 0.10 mmol) in anhydrous toluene (1.4 ml). The reaction medium is heated for 23 hours at reflux (110° C.) under an atmosphere of argon and with magnetic stirring. After cooling the reaction medium, the toluene is evaporated and the raw product purified by flash chromatography on silica (eluent dichloromethane:methanol=90:10). 0.30 g of a product is obtained which is dissolved in a minimum of chloroform and precipitated by hexane. After filtration and washing with hexane and then drying in a desiccator, 0.18 g of a white solid the compound (Z) 5-[4-[1-(5,6,7,8-tetrahydro-3,5,5,8,8-pentamethyl-2-naphthalenyl)-2-propenyl]phenyl]-1H-tetrazole (compound CB61692) (yield 66%).

m. pt. (° C.)=210

NMR$^1$H 200 MHz (DMSO-D$_6$): 0.68 (s, 6H, Me); 1.15 (s, 6H, Me); 1.30 (s, 4H, —CH$_2$—); 2.23 (d, 6H, Me); 6.54 (s, 1H, ArH); 6.59 (s broad, 1H, vinyl H); 7.31 (s, 1H, ArH); 7.35 (d, 2H, ArH meta to the tetrazole J 8.2 Hz); 7.90 (d, 2H, ArH ortho to the tetrazole J 8.2 Hz).

MS EI 70 eV (m/z, % intensity): 386 (M$^+$, 100%); 371 (31), 359 (21), 358 (73), 343 (29), 328 (16), 327 (21), 312 (21).

HRMS EI 70 eV: M$_{tr}$=386.2466 for C$_{25}$H$_{30}$N$_4$ M$_{th}$= 386.2470

HPLC: ODS column, Ultrasphere, 5μ, 250×4.6 mm, detector Shimadzu UV, 260 nm, flow rate 1 ml/min; eluent MeOH:H$_2$O=90:10+0.1% TFA, tetrazole (compound CB61692) tr=8.8 min 98.1%; impurities tr=8.0 min 0.3% and tr=12.0 min 1.6%.

EXAMPLES 5 AND 6

Preparation of the acids (E) and (Z) 4-[1-(3',4'-dihydro-4',4'-dimethyl-1',1'-dioxide-2'H-1'-benzothiopyran-6'-yl)-2-propenyl]benzoic acid (compounds CB39356 and CB72484) of formulae

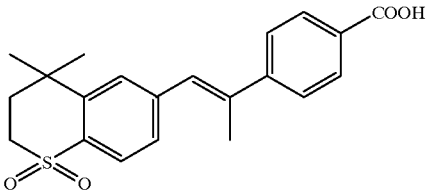

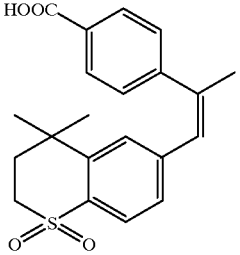

a) Preparation of 3-methylbut-2-enyl-4'-bromophenyl sulphide

A solution of 4-bromothiophenol (12.7 g, 61 mmol) in 18.5 ml of anhydrous THF is added drop by drop at ambient temperature to a solution of sodium hydride at 60% in a dispersion in mineral oil (3.2 g, 80 mmol) in 31 ml of anhydrous THF. The mixture is agitated at ambient temperature for 30 minutes and then a solution of 1-bromo-3-methyl-but-2-ene (7.7 ml, 67 mmol) in 15.5 ml of anhydrous THF and sodium iodide (1.83 g, 12 mmol) is added. The reaction medium is agitated at ambient temperature for 12 hours. It is hydrolysed at 0° C. with 30 ml of water. After returning to ambient temperature, it is extracted with ether (5×50 ml), dried over MgSO$_4$ and the solvents evaporated. 18.23 g of a yellowish oil, 3-methylbut- 2-enyl-4'-bromophenyl sulphide is obtained (gross yield=100%).

NMR$^1$H 200 MHz (CDCl$_3$): 1.60 (s, 3H, Me); 1.70 (s, 3H, Me); 3.50 (d, 2H, —CH$_2$— J 7.7 Hz); 5.20–5.30 (m, 1H vinyl H); 7.13–7.24 (m, 2H, ArH); 7.33–7.39 (m, 2H, ArH).

b) Preparation of 6-bromo-4,4-dimethyl-3,4-dihydro-2H-1-benzothiopyran

Aluminium trichloride (8.9 g, 67 mmol) is added at −10° C. to a solution of the raw 3-methylbut-2-enyl-4'-bromophenyl sulphide (18.23 g, 61 mmol) prepared in the previous step in 600 ml of dichloromethane. The reaction medium is agitated at this temperature for 3 hours and then poured over 500 ml of a volume to volume mixture of ice and water. This is extracted with dichloromethane and the organic phase is washed with a saturated aqueous solution of NaHCO$_3$, then dried over MgSO$_4$, filtered and evaporated. The raw product is purified by flash chromatography on silica (eluent petroleum ether:ethyl ether=100:5). 12.62 g of an oil 6-bromo-4,4-dimethyl-3,4-dihydro-2H-1-benzothiopyran is obtained (yield=80%).

NMR$^1$H 200 MHz (CDCl$_3$): 1.30 (s, 6H, 2 Me); 1.80–2.00 (m, 2H, —CH$_2$—); 2.80–3.05 (m, 2H, —CH$_2$—S); 6.85–7.60 (m, 3H, ArH).

c) Preparation of 6-formyl-4,4-dimethyl-3,4-dihydro-2H-1-benzothiopyran

The 6-bromo-4,4-dimethyl-3,4-dihydro-2H-1-benzothiopyran (2.62 g, 10 mmol) prepared in the previous step (b) and in solution in 5 ml of anhydrous THF, is added at 66° C. to magnesium (0.30 g, 12 mmol) in 1 ml of anhydrous THF. The mixture is agitated at reflux of the THF until quasi-complete consumption of the magnesium (30 minutes). The reaction medium is then cooled to −10° C. and at this temperature, the N-formylmorpholine (1.2 ml, 12 mmol) in 2 ml of THF is added. At the end of the addition, the reaction medium is brought to ambient temperature for 1 hour. After hydrolysis by 10 ml of an aqueous saturated NH$_4$Cl solution at 0° C. and extraction with ethyl ether (5×30 ml), the organic phase is dried over MgSO$_4$, filtered and evaporated. The raw product is purified by flash chromatography on silica (eluent petroleum ether:ethyl ether:100:5). 2.00 g of 6-formyl-4,4-dimethyl-3,4-dihydro-2H-1-benzothiopyran is obtained (yield=61%).

NMR$^1$H 200 MHz (CDCl$_3$): 1.60 (s, 6H, 2 Me); 1.90–2.00 (m, 2H, —CH$_2$—); 3.00–3.10 (m, 2H, —CH$_2$—S); 7.10–7.25 (m, 1H, ArH); 7.45–7.55 (m, 1H, ArH); 7.60 (m, 1H, Ar—H); 9.85 (s, 1H CHO).

d) Preparation of 6-(hydroxymethyl-4,4-dimethyl-3,4-dihydro-2H-1-benzothiopyran

Sodium borohydride (NaBH$_4$) (0.36 g, 9.7 mmol) is added at 0° C. to a solution of the previous 6-formyl-4,4-dimethyl-3,4-dihydro-2H-1-benzothiopyran (2.00 g, 9.7 mmol) in 20 ml of ethanol. The agitation was continued at this temperature for 30 minutes. After evaporation of the ethanol, it is taken up again in 100 ml of ethyl ether and acidified by an aqueous 3N solution of HCl to pH 1. The mixture is extracted with ether, dried over MgSO$_4$ filtered and the solvents evaporated. The crude product is purified by flash chromatography on silica (eluent petroleum ether:ethyl ether:100:10). 1.85 g of 6-(hydroxymethyl-4,4-dimethyl-3,4-dihydro-2H-1-benzothiopyrane is obtained (gross yield=92%).

NMR$^1$H 200 MHz (CDCl$_3$): 1.30 (s, 6H, 2 Me); 1.90–1.96 (m, 2H, —CH$_2$—); 2.97–3.03 (m, 2H, —CH$_2$—S); 4.56 (s, 2H, BnzH); 6.96–7.07 (m, 2H, ArH); 7.23–7.33 (m, 1H, ArH).

e) Preparation of 6-(bromomethyl-4,4-dimethyl-3,4-dihydro-2H-1-benzothiopyrane

Phosphorus tribromide (1 ml, 10.7 mmol) is added drop by drop with a syringe at between 20 and 25° C. to a solution of the previous 6-(hydroxymethyl-4,4-dimethyl-3,4-dihydro-2H-1-benzothiopyrane (1.85 g, 8.9 mmol) in 6.2 ml of anhydrous toluene. The mixture was left to agitate for 1 hour and then hydrolysed at 0° C. by ice and then by water. This was then extracted with ethyl ether, dried over MgSO$_4$, filtered and the solvents evaporated. 2.14 g of 6-(bromomethyl-4,4-dimethyl-3,4-dihydro-2H-1-benzothiopyrane is obtained (gross yield=88%).

NMR$^1$H 200 MHz (CDCl$_3$): 1.30 (s, 6H, 2 Me); 1.89–1.95 (m, 2H, —CH$_2$—); 2.97–3.03 (m, 2H, —CH$_2$—S); 4.44 (s, 2H, BnzH); 7.03 (s, 2H, ArH); 7.33 (s, 1H, ArH).

f) Preparation of (4,4-dimethyl-3,4-dihydro-2H-1-benzothiopyranyl)-6-methyltriphenylphosphonium bromide The 6-(bromomethyl-4,4-dimethyl-3,4-dihydro-2H-1-benzothiopyrane from the previous step (2.14 g, 7.8 mmol) is mixed at ambient temperature with triphenylphosphine (2.52 g, 9.6 mmol) in solution in 7 ml of dichloromethane for 18 hours, then diluted with ethyl ether (50 ml). The (4,4-dimethyl-3,4-dihydro-2H-1-benzothiopyranyl)-6-methyltriphenylphosphonium bromide precipitates, is filtered and washed thoroughly with ether. 4.36 g of white crystals which are dried in a desiccator and used as it is (gross yield=100%).

NMR$^1$H 200 MHz (CDCl$_3$): 1.00 (s, 6H, 2 Me); 1.76–1.82 (m, 2H, —CH$_2$—); 2.89–2.95 (m, 2H, —CH$_2$—S); 5.23 (d, 2H, BnzH J 14 Hz); 6.60–6.10 (m, 1H, ArH); 6.80–6.85 (m, 1H, ArH); 7.15 (m, 1H, ArH); 7.55–7.85 (m, 15H, —PPh$_3$).

g) Preparation of the compounds (E) and (Z) 4-[1-(3',4'-dihydro-4',4'-dimethyl-2'H-1'-benzothiopyran-6'-yl)-2-propenyl]benzonitriles of respective formulae

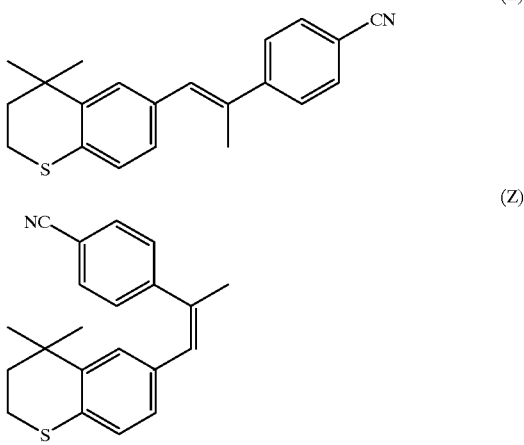

A solution of 4,4-dimethyl-3,4-dihydro-2H-1-benzothiopyranyl)-6-methyltriphenylphosphonium bromide from the previous step (2.41 g, 4.5 mmol), NaH (Aldrich, 4.1 mmol) coming from 0.16 g of a 60% dispersion of NaH in oil, in 2.5 ml of anhydrous DMSO is agitated under argon for 20 minutes and then a solution of 4-cyanoacetophenone (0.54 g, 3.75 mmol) in 5 ml of DMSO. The solution is agitated for 24 hours at ambient temperature and then poured over ice (70 g). The mixture is then extracted with ether (5×50 ml). The raw product is then purified by flash chromatography on silica (eluent petroleum ether:ethyl ether=100:10). 0.24 g of a pure solid the (E) compound 4-[1-(3',4'-dihydro-4',4'-dimethyl-2'H-1'-benzothiopyran-6'-yl)-2-propenyl]benzonitrile (yield=20%) and 0.13 g of a solid, the (Z) compound 4-[1-(3',4'-dihydro-4',4'-dimethyl-2'H-1'-benzothiopyran-6'-yl)-2-propenyl]benzonitrile (yield=11%).

Isomer (E)

NMR$^1$H 200 MHz (CDCl$_3$): 1.33 (s, 6H, 2 Me); 1.93–1.99 (m, 2H, —CH$_2$—); 2.26 (s, 3H, vinyl Me); 3.03–3.06 (m, 2H, —CH$_2$—S); 6.83 (s, 1H, vinyl H); 7.07 (m, 2H, ArH); 6.78–6.87 (m, 2H, ArH); 7.33 (s, 1H, ArH); 7.50–7.70 (m, 2H, ArH).

Isomer (Z)

NMR$^1$H 200 MHz (CDCl$_3$): 1.10 (s, 6H, 2 Me); 1.56–1.86 (m, 2H, —CH$_2$—); 2.16 (s, 3H, vinyl Me); 2.90–2.96 (m, 2H, —CH$_2$—S); 6.46 (s, 1H, vinyl H); 6.60 (dd, 1H, ArH J 1.9 Hz J 8.1 Hz); 6.78–6.87 (m, 2H, ArH); 7.28 (dd, 2H, ArH J 1.8 Hz, J 6.8 Hz); 7.54 (dd, 2H, ArH J 1.8 Hz, J 6.8 Hz).

h) Preparation of the compound (E) 4-[1-{3',4'-dihydro-4',4'-dimethyl-1',1'-dioxide-2'H-1'-benzothiopyran-6'-yl)-2-propenyl]benzonitrile of formula

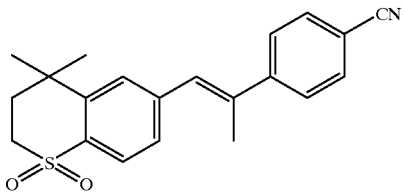

70–75% meta-chloroperbenzoic acid (0.37 g, 1.5 mmol) is added at 0° C. to a solution of the previous (E) compound 4-[1-(3',4'-dihydro-4',4'-dimethyl-2'H-1'-benzothiopyran-6'-yl)-2-propenyl]benzonitrile (0.24 g, 0.75 mmol) in 7 ml of chloroform. Agitation is continued at this temperature for 2 hours 30 minutes. The reaction medium is diluted by 15 ml of chloroform, then washed with an aqueous 5% $Na_2CO_3$ solution (3×5 ml). The organic phase is dried over $MgSO_4$, filtered then evaporated. 0.25 g of a solid the (E) compound 4-[1-{3',4'-dihydro-4',4'-dimethyl-1',1'-dioxide-2'H-1'-benzothiopyran-6'-yl)-2-propenyl]benzonitrile is obtained (gross yield=96%).

NMR[1]H 200 MHz ($CDCl_3$): 1.41 (s, 6H, 2 Me); 2.23 (s, 3H, vinyl Me); 2.37–2.45 (m, 2H, —$CH_2$—); 3.36–3.42 (m, 2H, —$CH_2$—S); 6.85 (s, 1H, vinyl H); 7.24–7.38 (m, 2H, ArH); 7.56–7.67 (m, 4H, ArH); 7.90 (d, 1H, ArH J 8.1 Hz).

i) Preparation of the compound (Z) 4-[1-{3',4'-dihydro-4',4'-dimethyl-1',1'-dioxide-2'H-1'-benzothiopyran-6'-yl)-2-propenyl]benzonitrile of formula

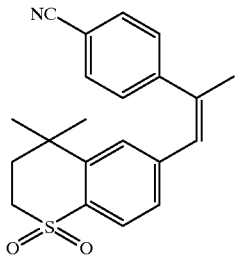

70–75% meta-chloroperbenzoic acid (0.32 g, 1.3 mmol) is added at 0° C. to a solution of the previous (Z) compound 4-[1-(3',4'-dihydro-4',4'-dimethyl-2'H-1'-benzothiopyran-6'-yl)-2-propenyl]benzonitrile (0.21 g, 0.65 mmol) in 6.1 ml of chloroform. Agitation is continued at this temperature for 3 hours. The reaction medium is diluted by 15 ml of chloroform, then washed with an aqueous 5% $Na_2CO_3$ solution (3×5 ml). The organic phase is dried over $MgSO_4$, filtered then evaporated. 0.21 g of a solid the (Z) compound 4-[1-{3',4'-dihydro-4',4'-dimethyl-1',1'-dioxide-2'H-1'-benzothiopyran-6'-yl)-2-propenyl]benzonitrile is obtained (gross yield=95%).

NMR[1]H 200 MHz ($CDCl_3$): 0.95 (s, 6H, 2 Me); 2.15 (s, 3H, vinyl Me); 2.20–2.30 (m, 2H, —$CH_2$—); 3.25–3.35 (m, 2H, —$CH_2$—S); 6.50 (s, 1H, vinyl H); 6.75 (s, 1H, ArH); 7.00 (dd, 1H, ArH J 1.3 Hz); 7.20 (m, 2H, ArH); 7.55 (d, 2H, J 7.5 Hz, ArH); 7.5 (d, 1H, J 7.5 Hz, ArH).

j) Preparation of the acid (E) 4-[1-(3',4'-dihydro-4',4'-dimethyl-1',1'-dioxide-2'H-1'-benzothiopyran-6'-yl)-2-propenyl]benzoic acid (compound CB39356) and the acid (Z) 4-[1-(3',4'-dihydro-4',4'-dimethyl-1',1'-dioxide-2'H-1'-benzothiopyran-6'-yl)-2-propenyl]benzoic acid (compound CB72484) of following respective formulae

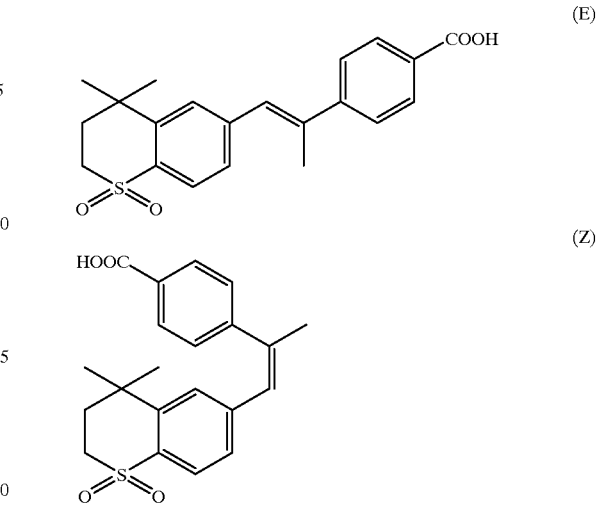

A suspension of the mixture of the (E) and (Z) compounds 4-[1-(3',4'-dihydro-4',4'-dimethyl-2'H-1'-benzothiopyran-6'-yl)-2-propenyl]benzonitriles (0.39 g, 0.75 mmol) in solution in ethanolic potassium hydroxide (KOH 0.5 g, 9.0 mmol, $H_2O$ 0.25 ml and EtOH 1.6 ml) is heated at reflux under magnetic stirring for 5 hours. The ethanol is evaporated in a rotary evaporator, taken up in water (50 ml), acidified with 3N HCl, extracted (3×25 ml) with ether and the ether phase dried over $MgSO_4$, filtered and evaporated. The raw product is purified by preparative HPLC on a Waters column HR $C_{18}$ (25×100 mm) with as eluent $CH_3CN:H_2O$=100:100+0.1% TFA. 15.8 mg of a white solid, the acid (E) 4-[1-(3',4'-dihydro-4',4'-dimethyl-1',1'-dioxide-2'H-1'-benzothiopyran-6'-yl)-2-propenyl]benzoic acid (yield=6%) (compound CB39356) and 17.2 mg of a white solid, the acid (Z) 4-[1-(3',4'-dihydro-4',4'-dimethyl-1',1'-dioxide-2'H-1'-benzothiopyran-6'-yl)-2-propenyl]benzoic acid (compound CB72484) (yield=6%).

Acid (E) 4-[1-(3',4'-dihydro-4',4'-dimethyl-1',1'-dioxide-2'H-1'-benzothiopyran-6'-yl)-2-propenyl]benzoic acid (compound CB39356).

m.pt. (° C.)=270–274

NMR[1]H 200 MHz ($CDCl_3$): 1.35 (s, 6H, 2 Me); 2.19 (d, 3H, vinyl Me J 1.0 Hz); 2.31–2.37 (m, 2H, —$CH_2$—); 3.30–3.36 (m, 2H, —$CH_2$—S); 6.80 (s, 1H, vinyl H); 7.30 (m, 2H, ArH); 7.49 (d, 2H, ArH J 8.3 Hz); 7.82 (d, 1H, ArH J 8.1 Hz); 7.97 (d, 2H, ArH J 8.3 Hz,).

MS EI 70 ev (m/z, % intensity): 370 ($M^+$, 100%); 338 (30); 337 (43); 44 (74); 40 (45).

MSHR EI 70 ev: $M_{tr}$=370.1257 for $C_{21}H_{22}O_4S$ $M_{th}$=370.1239.

HPLC: Column Waters HR $C_{18}$, 8×100 mm, 6μ, Waters UV detector 486 to 300 nm, flow rate 2.5 ml/min, eluent $CH_3CN:H_2O$=50:50+0.1% TFA, acid (compound CB39356) tr=4.52 min 98.8%.

Acid (Z) 4-[1-(3',4'-dihydro-4',4'-dimethyl-1',1'-dioxide-2'H-1'-benzothiopyran-6'-yl)-2-propenyl]benzoic acid (compound CB72484).

m.pt. (° C.)=210

NMR[1]H 200 MHz ($CDCl_3$): 1.02 (s, 6H, 2 Me); 2.20 (d, 3H, vinyl Me J 1.4 Hz); 2.23–2.27 (m, 2H, —$CH_2$—); 3.25–3.31 (m, 2H, $CH_2$—S); 6.52 (s, 1H, vinyl H); 6.82 (d, 1H, ArH J 1.3 Hz); 7.03 (dd, 1H, ArH J 8.3 Hz J 1.4 Hz); 7.24 (d, 2H, ArH J 7.9 Hz); 7.67 (d, 1H, ArH J 1.3 Hz,); 8.03 (d, 2H, ArH J 8.3 Hz).

MS EI 70 ev (m/z, % intensity): 370 (M+, 100%); 33B (10); 337 (44).

MSHR EI 70 ev: $M_{tr}$=370.1265 for $C_{21}H_{22}O_4S$ $M_{th}$=370.1239.

HPLC: Column Waters HR $C_{18}$, 8×100 mm, 6μ, Waters UV detector 486 to 260 nm, flow rate 2.5 ml/min, eluent $CH_3CN:H_2O$=50:50=0.1% TFA, acid (compound CB72484) tr=5.51 min 97.8%.

EXAMPLE 7

Preparation of compound (Z) 5-[4-[1-(3',4'-dihydro-4'4'-dimethyl-1',1'-dioxide-2'H-1'-benzothiopyran-6'-yl)-2-propenyl]phenyl]-1H-tetrazole (compound CB39122) of the following formula

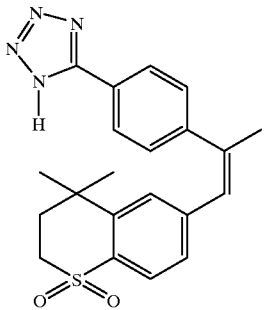

Dibutyl tin oxide (30 mg, 0.11 mmol) and trimethylsilyl azide (0.24 ml, 1.80 mmol), are added successively to a solution of the (Z) compound 4-[1-(3',4'-dihydro-4'4'-dimethyl-1',1'-dioxide-2'H-1'-benzothiopyran-6'-yl)-2-propenyl]benzonitrile (0.31 g, 0.90 mmol) in anhydrous toluene. The reaction medium is heated for 15 hours at reflux (110° C.) under an atmosphere of argon and with magnetic stirring. The mixture is purified by flash chromatography on silica (eluent $CH_2Cl_2$:MeOH=95:5). 0.16 g of a solid the compound (Z) 5-[4-[1-(3',4'-dihydro-4'4'-dimethyl-1',1'-dioxide-2'H-1'-benzothiopyran-6'-yl)-2-propenyl]phenyl]-1H-tetrazole (compound CB39122) is obtained (yield=46%).

m.pt. (° C.)=94

NMR$^1$H 200 MHz (CDCl$_3$): 1.05 (s, 6H, 2 Me); 2.24 (s, 5H, vinyl Me and —CH$_2$—); 3.25 (m, 2H); 6.50 (s, 1H, vinyl H); 6.91–6.98 (m, 2H, ArH); 7.23–7.27 (m, 2H, ArH); 7.62 (d, 1H, ArH J 8 Hz); 7.98 (d, 2H, ArH J 8 Hz,).

MS EI 70 ev (m/z, % intensity): 394 (M+, 42.9°); 354 (59); 321 (61); 293 (69); 44 (100).

MSHR EI 70 ev: $M_{th}$=394.1464 for $C_{21}H_{22}N_4O_2S$ $M_{tr}$=394.1489.

HPLC: Column Waters HR $C_{18}$, 8×100 mm, 6μ, Waters UV detector 486 to 260 nm, flow rate 2.5 ml/min, eluent MeOH:$H_2O$=75:25=0.1% TFA, sulphone (CB39122) tr=4.6 min 97.5%; impurities tr=4.3 1.9%; tr=5.1 0.5%.

EXAMPLE 8

Preparation of compound (E) 5-[4-[1-(3',4'-dihydro-4'4'-dimethyl-1',1'-dioxide-2'H-1'-benzothiopyran-6'-yl)-2-propenyl]phenyl]-1H-tetrazole (compound CB15068) of the following formula

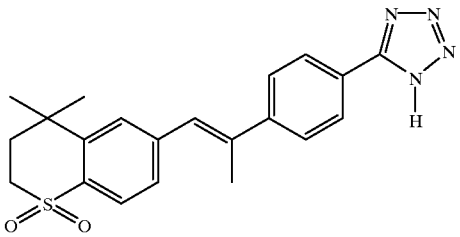

Dibutyl tin oxide (22.4 mg, 0.09 mmol) and trimethylsilyl azide (0.20 ml, 1.5 mmol), are added successively to a solution of the (E) compound 4-[1-(3',4'-dihydro-4'4'-dimethyl-1',1'-dioxide-2'H-1'-benzothiopyran-6'-yl)-2-propenyl]benzonitrile (0.31 g, 0.75 mmol) in anhydrous toluene. The reaction medium is heated for 15 hours at reflux (110° C.) under an atmosphere of argon and with magnetic stirring. The mixture is purified by preparative HPLC on a Waters column HR $C_{18}$ (25×100 mm) with eluent MeOH:$H_2O$=75:25=0.1% TFA. After evaporation and drying in a desiccator, 50 mg of a white solid the compound (E) 5-[4-[1-(3',4'-dihydro-4'4'4-dimethyl-1',1'-dioxide-2'H-1'-benzothiopyran-6'-yl)-2-propenyl]phenyl]-1H-tetrazole (compound CB15068) is obtained (yield=17%).

m.pt. (° C.)=224

NMR$^1$H 200 MHz (DMSO-d$_6$): 1.38 (s, 611, 2 Me); 2.41 (s, 5H, vinyl Me and —CH$_2$—); 3.30–3.45 (m, 1H, —CH$_2$—S); 3.50–3.60 (m, 1H, —CH$_2$—S); 7.12 (s, 1H, vinyl H) 7.53 (d, 2H, ArH J 8.5 Hz); 7.65 (s, 1H, ArH); 7.76–7.87 (m, 3H, ArH); 8.07 (d, 1H, ArH J 8.5 Hz).

MS EI 70 ev (m/z, % intensity): 394 (M+, 100%); 351 (47); 321 (38); 293 (39).

MSHR EI 70 ev: $M_{tr}$=394.1492 for $C_{21}H_{22}N_4O_2S$ $M_{th}$=394.1464.

HPLC: Column Waters HR $C_{18}$, 8×100 mm, 6μ, Waters UV detector 486 to 260 nm, flow rate 2.5 ml/min, eluent MeOH: $H_2O$=75:25=0.1% TFA, (CB15068) tr=2.2 min 100%.

EXAMPLE 9

Preparation of the compound (E) 4-[1-(5,6,7,8-tetrahydro-5,5,8,8-tetramethyl-2-naphthalenyl)-2-propenyl]-N-(tetrazol-5-yl)-benzamide (compound CB73364) of the following formula

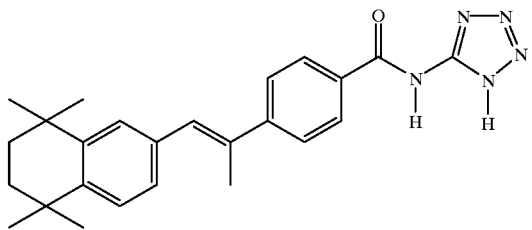

a) Preparation of 1,1,4,4,6-pentamethyl-1,2,3,4-tetrahydronaphthalene i) Aluminium trichloride (3.0 g, 22.5 mmol) is weighed into a 250 ml three-necked flask fitted with a condenser, a magnetic stirrer and a thermometer. 70 ml of anhydrous toluene (distilled and dried with a 4 Å molecular sieve) is added and then a solution of 2,5-dichloro-2,5-dimethylhexane (15.00 g, 81.9 mmol) in 30 ml of anhydrous benzene is added through a bromine ampoule. The reaction medium is heated at 100° C. for 2 hours. There is a large release of HCl and the reaction medium becomes dark red. After cooling the reaction medium, this is poured over an ice/water mixture (200 ml), extracted with ether (3×80 ml), washed with a saturated solution of $NaHCO_3$ (2×150 ml) and the ether phase dried with $MgSO_4$, filtered and evaporated. The raw product is purified by distillation under vacuum. 12.76 g of 1,1,4,4,6-pentamethyl-1,2,3,4-tetrahydronaphthalene is obtained (yield=77%) [b.pt.=66–67° C. under 1.5 mm Hg].

$NMR^1H$ 80 MHz ($CDCl_3$): 1.20 (s, 12H, 1,4-Me); 1.60 (s, 4H, —$CH_2$—); 2.25 (s, 3H, 6-Me); 6.80–7.30 (m, 3H, ArH).

(ii) Anhydrous $AlCl_3$ (Aldrich, 13.3 g, 100 mmol) is added at 0° C. in small quantities to a solution of distilled toluene (20.0 g, 217.0 mmol) and 2,2,5,5-tetramethyltetrahydrofurane (Aldrich, 12.5 g, 97.5 mmol). The cold bath is then removed and the reaction medium. agitated for 72 hours. Then 100 ml of 3N HCl solution is added, the organic phase separated and the aqueous phase extracted with ether (3×75 ml). The organic phases are collected together, washed with a saturated solution of $NaHCO_3$, dried over $MgSO_4$, filtered and evaporated. The raw product obtained is distilled under vacuum. 12.2 g of an oil 1,1,4,4,6-pentamethyl-1,2,3,4-tetrahydronaphthalene that crystallises in the cold is obtained (yield=62%).

$NMR^1H$ 80 MHz ($CDCl_3$): 1.20 (s, 12H, 1,4-Me); 1.60 (s, 4H, —$CH_2$—); 2.25 (s, 3H, 6-Me); 6.80–7.30 (m, 3H, ArH).

b) Preparation of 6-bromomethyl-1,1,4,4-tetramethyl-1,2,3,4-tetrahydronaphthalene A solution of 1,1,4,4,6-pentamethyl-1,1,4,4-tetrahydronaphthalene (2.14 g, 60.0 mmol), NBS (11.21 g, 63.0 mmol), benzoyl peroxide (0.436 g, 1.80 mmol) in 120 ml of $CCl_4$ is brought to reflux for 1 hour. The solution is then cooled, diluted with petroleum ether (120 ml), filtered and concentrated giving a yellowish oil. This is distilled (128–134° C., 1.2 mm Hg) to obtain 9.24 g of a colourless oil, 6-bromomethyl-1,1,4,4-tetramethyl-1,2,3,4-tetrahydronaphthalene (yield=55%).

$NMR^1H$ 80 MHz ($CDCl_3$): 1.25 (s, 12H, Me); 1.65 (s, 4H, —$CH_2$—); 4.40 (s, 2H, BnzH); 7.2–7.0 (m, 3H, ArH).

c) Preparation of (5,6,7,8-tetrahydro-5,5,8,8-tetramethyl-2-naphthalenyl)methyl-triphenyl-phosphonium bromide The 6-bromomethyl-1,1,4,4-tetramethyl-1,2,3,4-tetrahydronaphthalene (9.0 g, 32.0 mmol) prepared in the previous step is mixed with triphenylphosphine (10.1 g, 38.4 mmol) in solution in 50 ml of dichloromethane for 24 hours, and then diluted with ethyl ether (200 ml). The (5,6,7,8-tetrahydro-5,5,8,8-tetramethyl-2-naphthalenyl)methyl-triphenyl-phosphonium bromide precipitates, is filtered and washed with ether. The white crystals obtained (15.0 g, yield 86%) are dried in a desiccator.

m.pt (° C.)=270–271

$NMR^1H$ 200 MHz ($CDCl_3$): 0.54 and 0.88 (2s, 12H, 5,8-Me); 1.53 (s, 4H, 6,7-$CH_2$—); 5.13 (d, 1H, —$CH_2$P J 14 Hz); 6.88–6.75 (m, 2H, 1- and 3-ArH); 7.02 (d, 1H, 4-ArH J 8 Hz); 7.8–7.5 (m, 15H, —$Pph_3$).

d) Preparation of the compounds (E) and (Z) 4-[1-(5,6,7,8-tetrahydro-5,5,8,8-tetramethyl-2-naphthalenyl)-2propenyl]benzonitriles of respective formulae

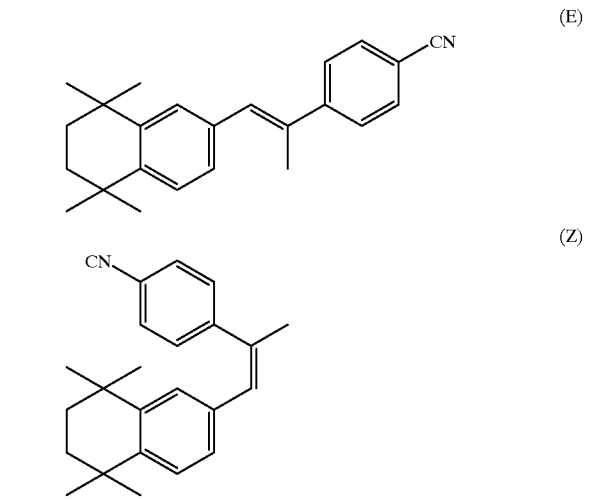

A solution of (5,6,7,8-tetrahydro-5,5,8,8-tetramethyl-2-naphthalenyl)methyl-triphenyl-phosphonium bromide (6.25 g, 11.5 mmol) and NaH (10.5 mmol), coming from 0.42 g of a dispersion of 60% NaH in oil, in 35 ml of anhydrous DMSO is agitated under argon for 20 minutes, during which a solution of 4-cyanoacetophenone (1.45 g, 10.0 mmol) in 15 ml of DMSO is added. The solution is agitated for 6 hours at ambient temperature then poured over ice (150 g). This was then extracted with ether (125 ml, 3×50 ml). The raw product is then purified by three successive flash chromatographies on silica (1st eluent hexane:acetone=5:95, 2nd eluent hexane:acetone=4:96, 3rd eluent hexane:acetone=2.5:97.5) so as to separate the (E) and the (Z) 4-[1-(5,6,7,8-tetrahydro-5,5,8,8-tetramethyl-2-naphthalenyl)-2-propenyl]benzonitriles. In order to obtain the pure (Z) isomer (less polar than the (E)isomer), the different fractions are verified by HPLC. The (E)isomer crystallises in the fractions coming from the flash chromatography. It is filtered, washed with hexane and dried at the palette pump. Its purity is determined by HPLC analysis.

0.57 g of (E) 4-[1-(5,6,7,8-tetrahydro-5,5,8,8-tetramethyl-2-naphthalenyl)-2-propenyl]benzonitrile is obtained in the form of a white solid (yield of pure compound=17.5%). 0.96 g of (Z) 4-[1-(5,6,7,8-tetrahydro-5,5,8,8-tetramethyl-2-naphthalenyl)-2-propenyl]benzonitrile is obtained in the form of a white solid (yield=30%). 0.70 g of a mixture of the two isomers is also obtained (yield of mixture=18%).

Isomer (E)

m.pt. (° C.)=173

$NMR^1H$ 200 MHz ($CDCl_3$): 1.29 (2s, 12H, 5,8-$CH_3$); 1.69 (s, 4H, 6,7-$CH_2$—); 2.29 (d, 3H, vinyl Me J 1.3 Hz); 6.87 (s broad, 1H, vinyl H); 7.13 (dd, 1H, 3-ArH J 8 Hz, J 1.9 Hz); 7.28 (m, 1H, 1-ArH); 7.31 (d, 1H, 4-ArH J 8.4 Hz); 7.60 (m, 4H, ArH ortho and meta to the CN).

HPLC: Lichrosorb L5-25F column, 5µ, 250×4.6 mm; eluent EtOAc:hexane=5:95.

flow rate: 1 ml/min, UV detection at 260 nm; isomer (E) tr=6.25 min 98.8%.

Isomer (Z)

m.pt. (° C.)=126

$NMR^1H$ 200 MHz ($CDCl_3$): 0.95 and 1.19 (2 s, 12H, 5,8-$CH_3$); 1.57 (s, 4H, 6,7-$CH_2$—); 2.16 (d, 3H, vinyl Me J 1.2 Hz); 6.49 (d, 1H, vinyl H J 1.2 Hz); 6.72 (m, 1H, 3-ArH);

6.73 (s, 1H, 1-ArH); 7.07 (d, 1H, 4-ArH J 8.6 Hz); 7.30 (d, 2H, ArH meta to the CN J 8 Hz); 7.56 (d, 2H, ArH ortho to the CN J 8 Hz).

HPLC: Lichrosorb L5-25F column, 5µ, 250×4.6 mm; eluent EtOAc:hexane=5:95.

flow rate: 1 ml/min, UV detection at 260 nm; isomer (Z) tr=6.8 min 98.3%, impurity isomer (E) tr=6.29 min 1.1%.

f) Preparation of the acid (E) 4-[1-(5,6,7,8-tetrahydro-5,5,8,8-tetramethyl-2-naphthalenyl)-2-propenyl]benzoic acid of formula

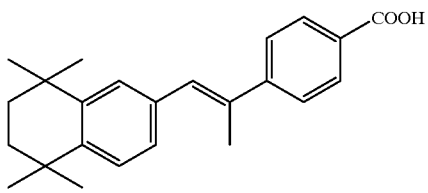

A suspension of the derivative (E) 4-[1-(5,6,7,8-tetrahydro-5,5,8,8-tetramethyl-2-naphthalenyl)-2-propenyl]benzonitrile (0.44 g, 1.20 mmol) in solution in alcoholic potassium hydroxide (0.94 g, 16.8 mmol KOH in 0.55 ml $H_2O$ and 3.3 ml EtOH) is heated to reflux under magnetic stirring for 4 hours. The progress of the reaction is followed by CCM (eluent acetone:hexane=10:90). The ethanol is evaporated in a rotary evaporator, the product taken up in water (50 ml), acidified with 1N HCl and extracted 3 times with ether. The ether phase is dried with $MgSO_4$, filtered and evaporated to obtain, after washing with pentane and drying, 0.40 g of a white powder the acid (E) 4-[1-(5,6,7,8-tetrahydro-5,5,8,8-tetramethyl-2-naphthalenyl)-2-propenyl]benzoic acid (yield=96%).

m.pt. (° C.): 230–2

NMR$^1$H 200 MHz ($CDCl_3$): 1.29 and 1.30 (2 s, 12H, 5,8-$CH_3$); 1.69 (s, 4H, 6,7-$CH_3$); 2.32 (s, 3H, vinyl Me); 6.91 (s, 1H, vinyl H); 7.16 (d, 1H, 3-ArH J 8 Hz), 7.29 (s, 1H, 1-ArH); 7.31 (d, 1H, 4-ArH J 7.9 Hz); 7.60 (d, 2H, ArH meta to the COOH J 8.4 Hz); 7.60 (d, 2H, ArH ortho to the COOH J 8.4 Hz).

HPLC: Ultrasphere ODS column, 5µ, 250×4.6 mm, UV detection at 260 nm, eluent MeOH:$H_2O$=90:10=0.1% TFA, pressure about 2500 psi, acid tr=12.7 min 99.9%, impurity tr=9.1 min 0.1%.

IR (pure, cm$^{-1}$): 3400–2200, 2928, 1672, 1602, 1424, 1280.

Micro-analysis

Tr.%C 82.6%H 7.95 calc.%C 8272%H 810

MS EI 70 ev (m/z): 348 (M$^+$, 75%); 333 (M$^+$—$CH_3$, 100).

g) Preparation of the compound (E) 4-[1-(5,6,7,8-tetrahydro-5,5,8,8-tetramethyl-2-naphthalenyl)-2-propenyl]-N-(tetrazol-5-yl)-benzamide (compound CB73364) of the following formula

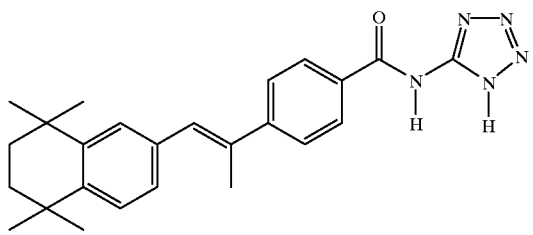

1 equivalent of N,N'-carbonyldi-imidazole (Aldrich, 0.46 g, 0.29 mmol) is added, at ambient temperature to a solution of acid (E) 4-[1-(5,6,7,8-tetrahydro-5,5,8,8-tetramethyl-2-naphthalenyl)-2-propenyl]benzoic acid (0.10 g, 0.29 mmol) in 5 ml of anhydrous THF. Half an hour later, 1 equivalent of 5-aminotetrazole monohydrate (Aldrich, 0.30 g, 0.29 mmol) is added. The magnetic stirring is continued for 15 hours 30 minutes. A white precipitate forms in the reaction medium. The mixture is evaporated to dryness and 10 ml of HCl is added. The solution is filtered and the filtrate washed with water and with methanol. After drying one night in a desiccator (with $P_2O_5$), 15 mg of a white solid is obtained the compound (E) 4-[1-(5,6,7,8-tetrahydro-5,5,8,8-tetramethyl-2-naphthalenyl)-2-propenyl]-N-(tetrazol-5-yl)-benzamide (compound CB73364) (yield=12%).

m.pt. (° C.)=318–321.

NMR$^1$H 200 MHz (DMSO $D_6$): 1.24 (s, 12H, 5,8-$CH_3$); 1.64 (s, 4H, 6,7-$CH_2$—); 2.27 (d, 3H, vinyl Me); 7.03 (s broad, 1H, vinyl H); 7.15–7.45 (m, 3H, ArH); 7.75 (d, 2H, ArH meta to the COOH J 8.4 Hz); 8.11 (d, 2H, ArH ortho to the COOH J 8.4 Hz). $H_2O$ signal at 3.58, DMSO signal 2.49.

MS DIC (isobutane) 200 ev (m/z, % intensity): 416 (M$^+$+1, 100%); 172 (22), 154 (48).

EXAMPLE 10

Preparation of the compound (E) 5-[4-[1-(5,6,7,8-tetrahydro-5,5,8,8-tetramethyl-2-naphthalenyl)-2-propenyl]phenyl]-1H-tetrazole (compound CB62458) of formula

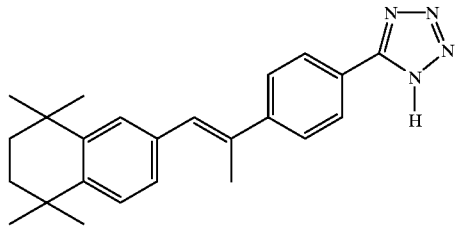

Dibutyl tin oxide (15.1 mg, 10% mol) and 2 equivalents of trimethylsilyl azide (0.19 ml, 1.46 mmol), are added successively to a solution of the (E) compound 4-[1-(5,6,7,8-tetrahydro-5,5,8,8-tetramethyl-2-naphthalenyl)-2-propenyl]benzonitrile (0.24 g, 0.73 mmol) in anhydrous toluene (1.25 ml). The reaction medium is heated for 16 hours at reflux (110° C.) under an atmosphere of argon and with magnetic stirring. The mixture is purified by flash chromatography on silica (eluent $CH_2Cl_2$ then MeOH:$CH_2Cl_2$=5:95) to obtain, after evaporation, 0.13 g of a white powder (E) 5-[4-[1-(5,6,7,8-tetrahydro-5,5,8,8-tetramethyl-2-naphthalenyl)-2-propenyl]phenyl]-1H-tetrazole (compound CB62458) (yield=48%).

m.pt. (° C.)=224–225.

NMR$^1$H 200 MHz (CDCl$_3$+DMSO D$_6$): 1.02 and 1.03 (2 s, 12H, 5,8-CH$_3$); 1.43 (s, 4H, 6,7-CH$_3$); 2.08 (d, 3H, Me J 1 Hz); 6.63 (s broad, 1H, vinyl H); 6.85–7.10 (m, 3H, ArH); 7.40 (d, 2H, ArH meta from the tetrazoyl J 8.4 Hz); 7.81 (d, 2H ArH ortho from the tetrazoyl J 8.4 Hz).

MS EI 70 ev (m/z, % intensity): 372 (M$^+$, 100%); 357 (28); 344 (74); 329 (31); 313 (23); 298 (13).

MSHR EI 70 ev: M$_{tr}$=372.2312 for C$_{24}$H$_{28}$N$_4$ M$_{th}$= 372.2314.

HPLC: ODS Column, Ultrasphere, 5μ, 250×4.6 mm, Shimadzu UV detector, 260 nm, eluent MeOH:H$_2$O=90:10+ 0.1% TFA, tetrazole (CB62458) tr=11.5 min 99.4%, impurity tetrazole (CB92834) tr=8.5 min 0.5%.

EXAMPLE 11

Preparation of the compound (Z) 5-[4-[1-(5,6,7,8-tetrahydro-5,5,8,8-tetramethyl-2-naphthalenyl)-2-propenyl]phenyl]-1H-tetrazole (compound CB92834) of formula

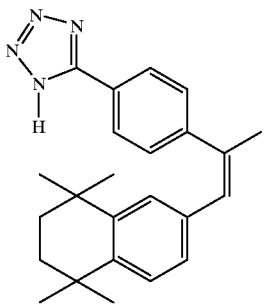

Dibutyl tin oxide (75 mg, 10% mol) and trimethylsilyl azide (0.97 ml, 7.28 mmol), are added successively to a solution of the (Z) compound 4-[1-(5,6,7,8-tetrahydro-5,5,8,8-tetramethyl-2-naphthalenyl)-2-propenyl]benzonitrile (1.20 g, 3.64 mmol) in anhydrous toluene (6.25 ml). The reaction medium is heated for 16 hours at reflux (110° C.) under an atmosphere of argon and with magnetic stirring. The mixture is purified by flash chromatography on silica (eluent CH$_2$Cl$_2$ then MeOH:CH$_2$Cl$_2$=5:95) to obtain, after evaporation, washing with hexane and drying at the palette pump, 0.99 g of a white powder, the compound (Z) 5-[4-[1-(5,6,7,8-tetrahydro-5,5,8,8-tetramethyl-2-naphthalenyl)-2-propenyl]phenyl]-1H-tetrazole (compound CB92834) (yield=73%).

m.pt. (° C.)=191–3.

NMR$^1$H 200 MHz (CDCl$_3$): 0.91 and 1.14 (2 s, 12H, 5,8-CH$_3$); 1.50 (s, 4H, 6,7-CH$_3$); 2.15 (d, 3H, Me J 1.2 Hz); 6.46 (s broad, 1H, vinyl H); 6.72 (dd, 1H, 3-ArH J 8.1 Hz J 1.5 Hz); 6.82 (d, 1H, 1-ArH J 1.6 Hz); 7.01 (d, 1H, 4-ArH J 8.2 Hz); 7.32 (d, 2H, ArH meta from the tetrazoyl J 8.1 Hz); 8.03 (d, 2H ArH ortho from the tetrazoyl J 8.1 Hz).

NMR$^{13}$C 50 MHz (CDCl$_3$): 26.7; 31.3; 31.6; 33.8; 33.9; 34.8; 122.3; 126.0; 127.4; 127.6; 127.9; 129.3; 133.7; 136.0; 143.2; 144.1; 148.2.

MS EI 70 ev (m/z, % intensity): 372 (M$^+$, 100%); 357 (M$^+$—CH$_3$, 20); 344 (70); 329 (23); 313 (17).

MSHR EI 70 ev: M$_{tr}$=372.2332 for C$_{24}$H$_{28}$N$_4$ M$_{th}$= 372.2314.

HPLC: ODS Column, Ultrasphere, 5μ, 250×4.6 mm, Shimadzu UV detector, 260 nm, eluent MeOH:H$_2$O=90:10+ 0.1% TFA, tetrazole (CB92834) tr=8.25 min 98.5%, impurity tetrazole (CB62458) tr=11.2 min 1.5%.

EXAMPLE 12

Preparation of the acid (E) 4-[1-trifluoromethyl-2-(5,6,7,8-tetrahydro-5,5,8,8 -tetramethyl-2-naphthalenyl)-1-ethenyl]benzoic acid (compound CB36493) of formula

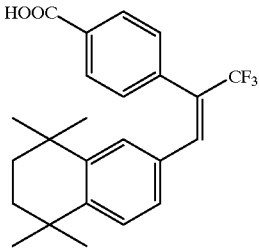

a) Preparation of 1-(4-benzonitrile)-2,2,2-trifluoroethanol

A solution of 4-cyanobenzaldehyde (Aldrich, 1.48 g, 11.28 mmol) and (trifluoromethyl)trimethylsilane (Fluka, 2 ml, 13.53 mmol) in 12 ml of THF is cooled to 0° C. and then a catalytic quantity of tetrabutylammonium fluoride TBAF, 1M in the THF (0.1 ml, 0.1 mmol) is added. The solution immediately becomes pale yellow and the solution is brought to ambient temperature for 4 hours. The reaction is followed by thin layer chromatography. At the end of reaction, the mixture is hydrolysed by 1N HCl, water is added and it is extracted with ether (150 ml), dried over MgSO$_4$, filtered and evaporated to obtain 2.15 g of a solid, 1-(4-benzonitrile)-2,2,2-trifluoroethanol, (gross yield= 95%).

NMR$^1$H 200 MHz (CDCl$_3$): 3.56 (s broad, 1H mobile, —OH); 5.08 (q, 1H, BnzH J 6.4 Hz); 7.55–7.70 (m, 4H, ArH).

NMR$^{19}$F 100 MHz (CDCl$_3$): −78.64 (d, 3F, J 2.9 Hz).

IR (pure, cm$^{-1}$): 3384, 2242, 1616, 1506, 1410, 1348, 1260, 1130.

b) 1-(4-benzonitrile)-2,2,2-trifluoroethane-1,1-diol

A solution of 1-(4-benzonitrile)-2,2,2-trifluoroethanol (2.15 g, 10.7 mmol) and PCC (3.45 g, 16.0 mmol) in 150 ml of dichloromethane is brought to reflux for 24 hours with vigorous magnetic stirring and an argon atmosphere. At the end of reaction, the reaction medium is cooled, filtered on florisil (Et$_2$O) where a raw product is obtained containing the expected diol in a mixture with about 15% of the starting alcohol (detection by gas phase chromatography). This mixture is purified by flash chromatography on silica (eluent Et$_2$O:petroleum ether=20:80) to obtain a first fraction containing 0.70 g of a mixture of alcohol and diol, then a second fraction containing 1.40 g of a white solid, 1-(4-benzonitrile)-2,2,2-trifluoroethane-1,1-diol. (yield=60%).

IR (pure, cm$^{-1}$): 3240 (broad), 2246, 1504, 1406, 1248, 1154, 1056, 1018, 922.

c) Preparation of 4-(cyano)-α,α,α-trifluoroacetophenone

A solution of 1-(4-benzonitrile)-2,2,2-trifluoroethane-1,1-diol (1.36 g, 6.26 mmol) in toluene (50 ml) is brought to reflux for 3 hours in a 100 ml Dean-Stark flask with magnetic stirring. After cooling the reaction medium, and evaporation to dryness 1.25 g of 4-(cyano)-α,α,α-trifluoroacetophenone is obtained (gross yield=100%).

m.pt. (° C.)=105

IR (pure, cm$^{-1}$): 2232, 1724, 1606, 1410, 1148, 938, 856.

d) Preparation of the compound (E) 4-[1-trifluoromethyl-2-(5,6,7,8-tetrahydro-5,5,8,8-tetramethyl-2-naphthalenyl)-1-ethenyl]benzonitrile of formula

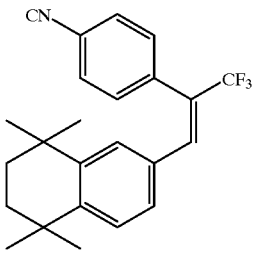

A solution of (5,6,7,8-tetrahydro-5,5,8,8-tetramethyl-2-naphthalenyl)methyl triphenylphosphonium bromide (4.28 g, 7.87 mmol), NaH (Aldrich, 7.18 mmol) coming from 0.29 g of a 60% dispersion of NaH in oil, in anhydrous DMSO is agitated under argon for 20 minutes during which a solution of 4-(cyano)-α,α,α-trifluoroacetophenone (1.25 g, 6.26 mmol) in 10 ml of DMSO is added. The solution is agitated for 5 hours at ambient temperature and then poured over ice (100 g). It is then extracted with ether (3×50 ml). The raw product is then purified by flash chromatography on silica (eluent Et$_2$O:petroleum ether=1:99). Each fraction is analysed by HPLC to verify that there is only one isomer and that the purity is sufficient. 1.35 g of a solid, (E) 4-[1-trifluoromethyl-2-(5,6,7,8-tetrahydro-5,5,8,8-tetramethyl-2-naphthalenyl)-1-ethenyl]benzonitrile is obtained (yield=56%) which is recrystallised in hexane to obtain 1.10 g of pure solid (recryst. yield=46%). 0.08 g of (Z) 4-[1-trifluoromethyl-2-(5,6,7,8-tetrahydro-5,5,8,8-tetramethyl-2-naphthalenyl)-1-ethenyl]benzonitrile is obtained (yield=4%) which is recrystallised in hexane to obtain 0.04 g of pure solid (recryst. yield=2%).

Isomer (E)

m. pt. (° C.)=131–132

NMR$^1$H 200 MHz (CDCl$_3$): 0.96 and 1.19 (2 s, 12H, 5,8-CH$_3$); 1.58 (s, 4H, 6,7-CH$_2$); 6.49 (dd, 1H, 3-ArH J 1.8 Hz J 8.3 Hz); 6.77 (d, 1H, 1-ArH J 1.8 Hz); 7.13 (d, 1H, 4-ArH J 8.3 Hz); 7.23 (d, 1H, vinyl H J 1.8 Hz); 7.44 (d, 2H, AH meta to the CN J 8.2 Hz); 7.70 (d, 2H, ArH ortho to the CN J 8.2 Hz).

NMR$^{19}$F 100 MHz (CDCl$_3$): −65.6 (s, 3 F, —CF$_3$).

HPLC: Lichrosorb L5-25F column, 5μ, 250×4.6 mm; eluent AcOEt:hexane=3:97, flow rate: 1 ml/min, UV detection at 260 nm; isomer (E) tr=6.6 min 99.8%.

Isomer (Z)

m. pt. (° C.)=131–132

NMR$^1$H 200 MHz (CDCl$_3$): 1.29 (s, 12H, 5,8-CH$_3$); 1.69 (s, 4H, 6,7-CH$_2$); 7.05 (s broad, 1H, vinyl H); 7.19 (dd, 1H 3-ArH J 8 Hz J 1.9 Hz); 7.32 (d, 1H, 4-ArH J 8 Hz); 7.38 (d, 1H, 1-ArH J 1.9 Hz); 7.56 (d, 2H, ArH meta from the CN J 8.2 Hz); 7.68 (d, 2H, ArH ortho from the CN J 8.2 Hz).

NMR$^{19}$F 100 MHz (CDCl$_3$): −56.6 (s, 3F, —CF$_3$).

HPLC: Lichrosorb L5-25F column, 5μ, 250×4.6 mm; eluent AcOEt:hexane=3:97, flow rate: 1 ml/min, UV detection at 260 nm; isomer (Z) tr=12.6 min 95.2%, isomer (E) tr=6.6 min 3.5%.

e) Preparation of the acid (E) 4-[1-trifluoromethyl-2-(5,6,7,8-tetrahydro-5,5,8,8-tetramethyl-2-naphthalenyl)-1-ethenyl]benzoic acid (compound CB36493) of formula

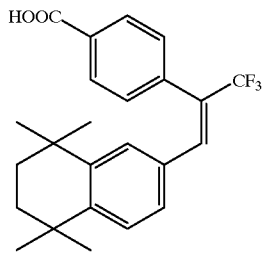

A suspension of derivative (E) 4-[1-trifluoromethyl-2-(5,6,7,8-tetrahydro-5,5,8,8-tetramethyl-2-naphthalenyl)-1-ethenyl]benzonitrile (0.50 g, 1.30 mmol) in solution in alcoholic potassium hydroxide (0.94 g, 16.8 mmol KOH in 0.55 ml H$_2$O and 3.3 ml EtOH) is heated to reflux under magnetic stirring for 5 hours. The progress of the reaction is followed by CCM. The ethanol is evaporated in a rotary evaporator, the product taken up in water (50 ml), acidified with 1N HCl and extracted with ether (3×60 ml). The ether phase is dried with MgSO$_4$, filtered and evaporated to obtain a raw product that is purified by flash chromatography on silica (eluent Et$_2$O:petroleum ether 50:50, height of the silica=5 cm). After evaporation of the fractions, a light orange solid is obtained that is washed in pentane (×2). After filtration and drying at 50° C. (24 hours) in a desiccator under vacuum, 0.19 g of a off-white solid is obtained, the pure acid (E) 4-[1-trifluoromethyl-2-(5,6,7,8-tetrahydro-5,5,8,8-tetramethyl-2-naphthalenyl)-1-ethenyl]benzoic acid (compound CB36493) (yield=36%).

m. pt. (° C.)=161–162

NMR$^1$H 200 MHz (CDCl$_3$): 0.96 and 1.19 (2s, 12H, 5,8-CH$_3$); 1.57 (s, 4H, 6,7-CH$_2$); 6.77 (dd, 1H, 3-ArH J 1.8 Hz J 8.2 Hz); 6.88 (d, 1H, 1-ArH J 1.8 Hz); 7.11 (d, 1H, 4-ArH J 8.2 Hz); 7.21 (d, 1H, vinyl H J 1.6 Hz); 7.46 (d, 2H, ArH meta from the COOH J 8.2 Hz); 8.16 (d, 2H, ArH ortho from the COOH J 8.2 Hz).

NMR$^{19}$F 100 MHz (CDCl$_3$): −65.7 (s, 3F, —CF$_3$).

MS EI 70 ev (m/z, % intensity): 402 (M$^+$, 51%); 387 (M$^+$—CH$_3$, 100); 345 (16).

HRMS EI 70 ev: M$_{tr}$=402.1815 for C$_{24}$H$_{25}$F$_3$O$_2$ M$_{tr}$=402.1807.

HPLC: ODS Column, Ultrasphere, 5μ, 250×4.6 mm, Shimadzu UV detector, 260 nm, flow rate 1 ml/min, eluent MeOH:H$_2$O=90:10=0.1% TFA, acid (CB36493) tr=7.63 min 99.5%, impurities tr=6.41 min 0.15%; tr=4.4 min 0.08%.

IR (pure, cm$^{-1}$): 2958, 1692, 1608, 1416, 1284, 1160, 1105, 922, 858.

EXAMPLE 13

Preparation of compound (E) 5-[4-[1-trifluoromethyl-2-(5,6,7,8-tetrahydro-5,5,8,8-tetramethyl-2-naphthalenyl)-1-ethenyl]phenyl]-1H-tetrazole (compound CB77402) of formula

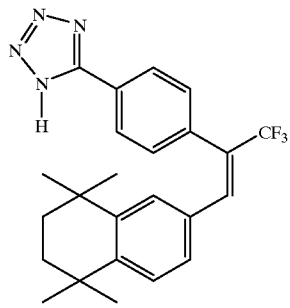

Dibutyl tin oxide (15.1 mg, 10% mol) and trimethylsilyl azide (0.16 ml, 1.22 mmol), are added successively to a solution of the (E) compound 4-[1-trifluoromethyl-2-(5,6,7,8-tetrahydro-5,5,8,8-tetramethyl-2-naphthalenyl)-1-ethenyl]benzonitrile (0.24 g, 0.61 mmol) in anhydrous toluene (1.25 ml). The reaction medium is heated for 16 hours at reflux (110° C.) under an atmosphere of argon and with magnetic stirring. The mixture is purified by flash chromatography on silica (eluent $CH_2Cl_2$ then $MeOH:CH_2Cl_2$=5:95) to obtain, after evaporation and washing with pentane, a greenish powder, compound (E) 5-[4-[1-trifluoromethyl-2-(5,6,7,8-tetrahydro-5,5,8,8-tetramethyl-2-naphthalenyl)-1-ethenyl]phenyl]-1H-tetrazole (compound CB77402) (yield=58%), which is dried at 50° C. (24 hours) in a desiccator. This solid can be recrystallised with chloroform.

m. pt. (° C.)=210–211

NMR$^1$H 200 MHz (CDCl$_3$): 0.94 and 1.16 (2 s, 12H, 5,8-CH$_3$); 1.54 (s, 4H, 6,7-CH$_2$); 6.77 (dd, 1H, 3-ArH J 1.7 Hz J 8.2 Hz); 6.93 (d, 1H, 1-ArH J 1.7 Hz); 7.09 (d, 1H, 4-ArH J 8.2 Hz); 7.21 (d, 1H, vinyl H J 1.4 Hz); 7.50 (d, 2H, ArH meta from the tetrazoyl J 8.2 Hz); 8.17 (d, 2H, ArH ortho from the tetrazoyl J 8.2 Hz).

NMR$^{19}$F 100 MHz (CDCl$_3$): –65.76 (s, 3F, —CF$_3$).

MS EI 70 ev (m/z, % intensity): 426 (M$^+$, 100%); 411 (M$^+$—CH$_3$, 74); 398 (80), 383 (35); 368 (15); 352 (16); 341 (11); 326 (10).

HRMS EI 70 ev: M$_{tr}$=426.2005 for C$_{24}$H$_{25}$F$_3$N$_4$ M$_{th}$=426.2031.

HPLC: ODS Column, Ultrasphere, 5µ, 250×4.6 mm, Shimadzu UV detector, 260 nm, flow rate 1 ml/min, eluent MeOH:H$_2$O=90:10=0.1% TFA, tetrazole (CB77402) tr=6.11 min 98.5%, impurities: acid (CB36493) tr=7.57 min 1.1%; unknown tr=12.07 min 0.15%.

EXAMPLE 14

Preparation of the acid (E) 4-[1-trifluoromethyl-2-(5,6,7,8-tetrahydro-3,5,5,8,8-pentamethyl-2-naphthalenyl)-1-ethenyl]benzoic acid (compound CB62899) of formula

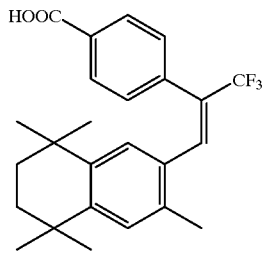

a) Preparation of compound (E) 4-[1-(5,6,7,8-tetrahydro-3,5,5,8,8-pentamethyl-2-naphthalenyl)-2-(trifluoromethyl)-ethen-2-yl)]benzonitrile of formula

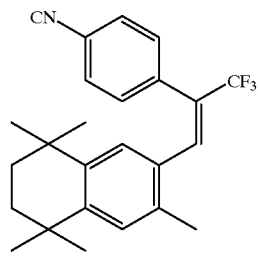

(5,6,7,8-tetrahydro-3,5,5,8,8-pentamethyl-2-naphthalenyl)methyltriphenylphosphonium bromide (1.75 g, 3.14 mmol) in solution in 10 ml of anhydrous THF was introduced into a 50 ml flask fitted with magnetic stirring and under an atmosphere of argon. A solution of tBuOK in THF (3.26 ml, 3.26 mmol) is added drop by drop at –78° C. and the agitation is continued at –70° C. for 2 hours. A solution of 4-(cyano)-α,α,α-trifluoracetophenone (0.50 g, 2.51 mmol) in 2.5 ml of THF is added with a syringe. The agitation is continued and the temperature is allowed to rise again to ambient during 4 hours 30 minutes. The mixture is hydrolysed at 0° C. by a 6N solution of HCl (7 ml) and then 15 ml of distilled water is added before extracting with dichloromethane (3×50 ml). This is dried over MgSO$_4$, filtered and the solvents evaporated. The raw product is then purified by flash chromatography on silica (eluent ethyl ether:petroleum ether=1.5:98.5). 0.65 g is obtained of a white solid (E) 4-[1-trifluoromethyl-2-(5,6,7,8-tetrahydro-3,5,5,8,8-pentamethyl-2-naphthalenyl)-1-ethenyl]benzonitrile of formula:

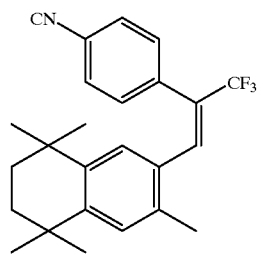

(yield=65%) then 0.01 g of (Z) 4-[1-trifluoromethyl-2-(5,6,7,8-tetrahydro-3,5,5,8,8-pentamethyl-2-naphthalenyl)-1-ethenyl]benzonitrile (yield=1%).

Isomer (E)

m. Pt. (° C.)=89–90

NMR$^1$H 200 MHz (CDCl$_3$): 0.76 and 1.21 (2s, 12H, 5,8-CH$_3$); 1.40–1.65 (m, 4H, 6,7-CH$_2$); 2.32 (s, 3H, Me); 6.54 (s, 1H, ArH); 7.06 (s, 1H, vinyl H); 7.36 (d, 2H, ArH); 7.45 (m, 1H, ArH); 7.60 (d, 2H, ArH).

NMR19F 100 MHz (CDCl$_3$): –65.0 (s, 3F, —CF$_3$).

Isomer (Z)

NMR$^1$H 200 MHz (CDCl$_3$): 1.26 (d, 12H, Me J 1.6 Hz); 1.67 (s, 4H, 6,7-CH$_2$); 2.27 (s, 3H, Me); 7.11 (s, 1H, ArH); 7.13 (s, 1H, ArH); 7.25 (s, 1H, vinyl H); 7.58 (d, 2H, ArH meta to the CN J 8.4 Hz); 7.70 (d, 2H, ArH ortho to the CN J 8.4 Hz).

NMR$^{19}$F 100 MHz (CDCl$_3$): –56.8 (s, 3F, —CF$_3$)

b) Preparation of the acid (E) 4-[1-trifluoromethyl-2-(5,6,7,8-tetrahydro-3,5,5,8,8-pentamethyl-2-naphthalenyl)-1-ethenyl]benzoic acid (compound CB62899) of formula

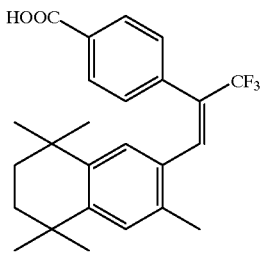

A suspension of compound (E) 4-[1-trifluoromethyl-2-(5,6,7,8-tetrahydro-3,5,5,8,8-pentamethyl-2-naphthalenyl)-1-ethenyl]benzonitrile (0.56 g, 1.41 mmol) in solution in alcoholic potassium hydroxide (2.00 g, 35.71 mmol KOH in 6.6 ml H$_2$O and 1 ml EtOH) is heated to reflux under magnetic stirring for 5 hours. The progress of the reaction is followed by CCM. The ethanol is evaporated in a rotary evaporator, the product taken up in water (50 ml), acidified with 1N HCl and extracted with ether (3×80 ml). The ether phase is dried with MgSO$_4$, filtered and evaporated to obtain a raw product that is purified by flash chromatography on silica (eluent ether:petroleum ether 70:30). After evaporation of the fractions, 0.44 g of a pure white solid is obtained, the acid (E) 4-[1-trifluoromethyl-2-(5,6,7,8-tetrahydro-3,5,5,8,8-pentamethyl-2-naphthalenyl)-1-ethenyl]benzoic acid (compound CB62899) (yield=75%).

m.pt. (° C.)=151 (Köfler test rig)

NMR$^1$H 200 MHz (CDCl$_3$): 0.73 and 1.19 (2s, 12H, 5,8-CH$_3$); 1.40–1.60 (m, 4H, 6,7-CH$_2$); 2.32 (s, 3H, Me); 6.60(s, 1H, ArH); 7.04 (s, 1H, ArH); 7.37 (d, 2H, ArH J 8.2 Hz); 7.42 (s, 1H, vinyl H); 8.06 (d, 2H, ArH J 8.2 Hz).

NMR$^{19}$F 100 MHz (CDCl$_3$): –65.1 (s, 3F, —CF$_3$).

MS EI 70 ev (m/z, % intensity): 416 (M$^+$, 47%); 401 (M$^+$—CH$_3$, 100); 359 (11).

HRMS EI 70 ev: M$_{tr}$=416.1962 for C$_{25}$H$_{27}$F$_3$O$_2$ M$_{tr}$=416.1963.

HPLC: ODS Column, Ultrasphere, 5$\mu$, 250×4.6 mm, Shimadzu UV detector, 260 nm, flow rate 1 ml/min, eluent MeOH:H$_2$O=90:10=0.1% TFA, acid (CB62899) tr=9.5 min 97%, impurity tr=11.2 min 2.65%.

EXAMPLE 15

Preparation of compound (E) 5-[4-[1-trifluoromethyl-2-(5,6,7,8-tetrahydro-3,5,5,8,8-pentamethyl-2-naphthalenyl)-1-ethenyl]phenyl]-1H-tetrazole (compound CB63237) of formula

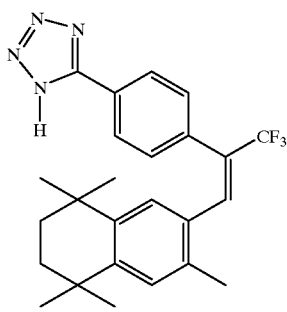

Dibutyl tin oxide (15.1 mg, 10% mol) and trimethylsilyl azide (0.16 ml, 1.22 mmol), are added successively to a solution of the (E) compound 4-[1-trifluoromethyl-2-(5,6,7,8-tetrahydro-3,5,5,8,8-pentamethyl-2-naphthalenyl)-1-ethenyl]benzonitrile (0.24 g, 0.60 mmol) in anhydrous toluene (1.25 ml). The reaction medium is heated for 16 hours at reflux (110° C.) under an atmosphere of argon and with magnetic stirring. The mixture is purified by flash chromatography on silica (eluent CH$_2$Cl$_2$ then MeOH:CH$_2$Cl$_2$=5:95) to obtain, after evaporation and washing with pentane and drying, 0.13 g of a white solid, compound (E) 5-[4-[1-trifluoromethyl-2-(5,6,1,8-tetrahydro-3,5,5,8,8-pentamethyl-2-naphthalenyl)-1-ethenyl]phenyl]-1H-tetrazole (compound CB63237) (yield=49%).

m. pt. (° C.)=203–205

NMR$^1$H 200 MHz (DMSO): 0.73 and 1.19 (2s, 12H, 5,8-CH$_3$); 1.40–1.65 (s, 4H, 6,7-CH$_2$); 2.34 (s, 3H, Me); 6.60 (s, 1H, ArH); 7.12 (s, 1H, ArH); 7.46 (d, 2H, ArH J 8.4 Hz); 7.54 (s, 1H, vinyl H); 8.02 (d, 2H, ArH J 8.4 Hz).

NMR$^{19}$F 100 MHz (CDCl$_3$): –67.9 (s, 3F, —CF$_3$).

MS EI 70 ev (m/z, % intensity): 440 (M$^+$, 90%); 425 (M$^+$—CH$_3$, 100); 412 (31), 397 (29); 366 (10); 198 (12).

HRMS EI 70 ev: M$_{tr}$=440.2178 for C$_{25}$H$_{27}$F$_3$N$_4$ M$_{th}$=440.2169.

HPLC: ODS Column, Ultrasphere, 5$\mu$, 250×4.6 mm, Shimadzu UV detector, 260 nm, flow rate 1 ml/min, eluent MeOH:H$_2$O=90:10=0.1% TFA, tetrazole (CB63237) tr=7.60 min 97.7%, impurities: tr=8.9 min 1.9%.

EXAMPLE 16

Preparation of compound (E) [1-(5,6,7,8-tetrahydro-5,5,8,8-tetramethyl-2-naphthalenyl)-1-(phenyl)-2-ethenyl]benzene (compound CB04854) of the following formula

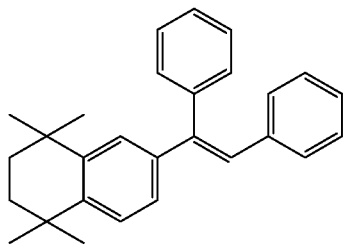

a) Preparation of 1,1,4,4-tetramethyl-1,2,3,4-tetrahydronaphthalene

Aluminium trichloride (0.60 g, 4.49 mmol) is weighed into a 100 ml three-necked flask fitted with a condenser, a magnetic stirrer and a thermometer. 20 ml of anhydrous benzene is added and then a solution of 2,5-dichloro-2,5-dimethylhexane (3.00 g, 16.38 mmol) in 10 ml of anhydrous benzene is added through a bromine ampoule. The reaction medium is heated to reflux for 4 hours. There is a large release of HCl and the reaction medium becomes dark red. After cooling the reaction medium, this is poured over ar ice/water mixture (100 ml), extracted with ether (3×50 ml), washed with a saturated solution of NaHCO$_3$ (2×100 ml) and the ether phase dried with MgSO$_4$, filtered and evaporated. The raw product is purified by flash chromatography on silica (eluent petroleum ether). 1.95 g (yield=63%) of a colourless liquid, 1,1,4,4-tetramethyl-1,2,3,4-tetrahydronaphthalene is obtained.

b.pt.=74° C. under 0.5 mm Hg].

NMR$^1$H 80 MHz (CDCl$_3$): 1.28 (s, 12H, 1,4-Me); 1.68 (s, 4H, —CH$_2$—); 7.05–7.40 (m, 4H, ArH).

b) Preparation of 4-bromophenylacetyl chloride

Thionyl chloride (2.5 ml, 34.8 mmol) is added at ambient temperature to a solution of 4-bromophenylacetic acid (Aldrich, 5 g, 23.2 mmol) in 10 ml of toluene. The reaction medium is brought to reflux for 2 hours. After returning to ambient temperature, the toluene is evaporated and 5.55 g of raw 4-bromophenylacetyl chloride is obtained (gross yield=100%).

c) Preparation of 4-[1-(5,6,7,8-tetrahydro-5,5,8,8-tetramethyl-2-naphthalenyl)-1-oxo-2-ethyl]bromobenzene of formula

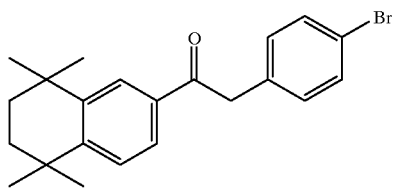

Aluminium trichloride (4.33 g, 32.5 mmol) and 4-bromophenylacetyl chloride (5.55 g, 23.2 mmol) are added successively at −30° C. to a solution of 1,1,4,4-tetramethyl-1,2,3,4-tetrahydronaphthalene (4.36 g, 23.2 mmol) in 300 ml of dichloromethane. The temperature is allowed to rise to 0° C. in 30 minutes, the reaction mixture is poured over 400 ml of a volume to volume mixture of ice and water and this is extracted with dichloromethane. The organic phase is dried over MgSO$_4$, filtered and evaporated. The raw product is purified by crystallisation in hexane to obtain 5.69 g of a white solid, 4-[1-(5,6,7,8-tetrahydro-5,5,8,8-tetramethyl-2-naphthalenyl)-1-oxo-2-ethyl]bromobenzene (yield=63%).

m.pt. (° C.)=197

NMR$^1$H 200 MHz (CDCl$_3$): 1.31 (s, 6H, 2 Me); 1.32 (s, 6H, 2 Me); 1.72 (s, 4H, 2 —CH$_2$—); 4.22 (s, 2H, BnzH); 7.16 (d, 2H, ArH J 8.5 Hz); 7.44 (d, 2H, ArH J 8.5 Hz); 7.41 (d, 1H, ArH, J 8.5 Hz); 7.77 (dd, 1H, ArH J 1.8 Hz J 8.5 Hz); 8.02 (d, 1H, ArH J 1.8 Hz).

NMR$^{13}$C 50 MHz (CDCl$_3$): 31.6; 31.8; 34.4; 34.7; 34.8; 44.7; 120.8; 125.7; 127.0; 127.1; 131.3 (2C); 131.6 (2C); 133.8; 133.9; 145.4; 151.0; 196.6.

MS IC butane (m/z, % intensity): 387, 385 (MH$^+$, 100%, 97%).

d) Preparation of 4-[1-(5,6,7,8-tetrahydro-5,5,8,8-tetramethyl-2-naphthalenyl)-1-(phenyl)-1-(hydroxy)-2-ethyl]bromobenzene of formula

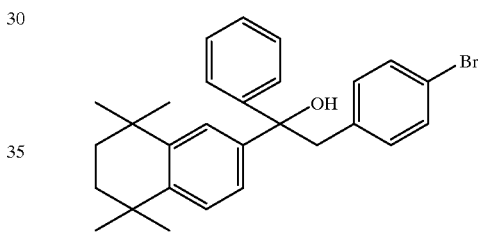

A 1.4 M solution of phenyl lithium in a mixture of toluene:ether of 3:1 (8.6 ml, 12.0 mmol) is added at −70° C. to a solution of 4-[1-(5,6,7,8-tetrahydro-5,5,8,8-tetramethyl-2-naphthalenyl)-1-oxo-2-ethyl]bromobenzene (3.85 g, 10.0 mmol) in 30 ml of THF. The agitation was continued for 45 minutes at −70° C. and then the mixture was hydrolysed by 25 ml of a saturated solution of NH$_4$Cl. The temperature of the mixture rises to ambient and it is extracted with ether (5×50 ml), dried over MgSO$_4$, filtered and evaporated. The raw product is purified by flash chromatography on silica (eluent, petroleum ether:ether=100:5). 2.48 g of a white solid is obtained, the compound 4-[1-(5,6,7,8-tetrahydro-5,5,8,8-tetramethyl-2-naphthalenyl)-1-(phenyl)-1-(hydroxy)-2-ethyl]bromobenzene, (yield=53%).

m.pt. (° C.)=130–132

NMR$^1$H 200 MHz (CDCl$_3$): 1.20 (s, 12H, 4 Me); 1.60 (s, 4H, 3 —CH$_2$—); 3.52 (s, 2H, BnzH); 6.22 (d, 2H, ArH J 8 Hz); 7.05 (dd, 1H, J 3 Hz J 8 Hz); 7.15–7.45 (m, 10H, ArH).

e) Preparation of the (E) and (Z) compounds 4-[1-(5,6,7,8-tetrahydro-5,5,8,8-tetramethyl-2-naphthalenyl)-1-(phenyl)-2-ethenyl]bromobenzenes of respective following formulae

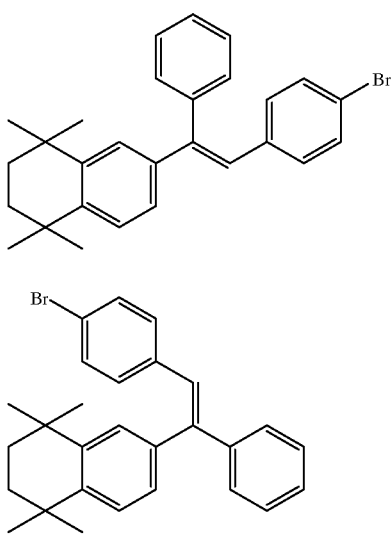

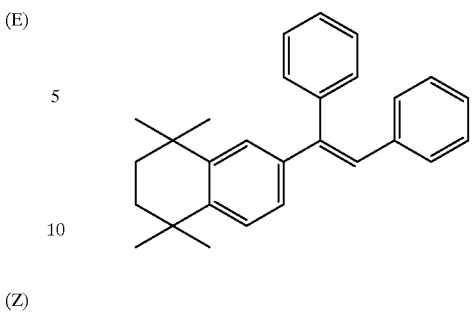

A solution of 3N HCl (8.5 ml, 25.5 mmol) is added at ambient temperature to a solution of 4-[1-(5,6,7,8-tetrahydro-5,5,8,8-tetramethyl-2-naphthalenyl)-1-(phenyl)-1-(hydroxy)-2-ethyl]bromobenzene (2.48 g, 5.34 mmol) in 26 ml of ethanol. The reaction mixture is refluxed for 2 hours. After returning to ambient temperature, 25 ml of water is added and the mixture extracted with ether (5×50 ml), dried over MgSO₄, filtered and evaporated. The raw product is recrystallised in ethanol and after filtering and drying 0.60 g of a white solid is obtained, the (E) compound 4-[1-(5,6,7,8-tetrahydro-5,5,8,8-tetramethyl-2-naphthalenyl)-1-(phenyl)-2-ethenyl]bromobenzene (yield= 25%). The filtrate is evaporated to dryness and then the raw product is obtained and purified by flash chromatography on silica (eluent petroleum ether). 1.11 g of an oil is obtained the (Z) compound 4-[1-(5,6,7,8-tetrahydro-5,5,8,8-tetramethyl-2-naphthalenyl)-1-(phenyl)-2-ethenyl]bromobenzene (yield=47%) (containing about 10% of the (E)isomer determined by NMR$^1$H).

Isomer (E)

m.pt. (° C.) 147

NMR$^1$H 200 MHz (CDCl$_3$) 1.10 (s, 6H, 2 Me); 1.15 (s, 6H, 2 Me); 1.62 (s, 4H, 2 —CH$_2$—); 6.80–6.90 (m, 3H, vinyl H and ArH); 6.95–7.05 (m, 1H, ArH); 7.10–7.35 (m, 9H, ArH).

Isomer (Z)

m.pt. (° C.) 114

NMR$^1$H 200 MHz (CDCl$_3$): 1.05 (s, 6H, 2 Me); 1.27 (s, 6H, 2 Me); 1.65 (s, 4H, 2 —CH$_2$—); 6.80–6.90 (m, 3H, vinyl H and ArH); 7.07–7.12 (m, 1H, ArH); 7.15–7.40 (m, 9H, ArH).

f) Preparation of the (E) compound [1-(5,6,7,8-tetrahydro-5,5,8,8-tetramethyl-2-naphthalenyl)-1-(phenyl)-2-ethenyl]benzene (compound CB04854) of formula A 1.6 M solution of n-butyl lithium in hexane (0.12 ml, 0.19 mmol) is added at −70° C. to a solution of (E) 4-[1-(5,6,7,8-tetrahydro-5,5,8,8-tetramethyl-2-naphthalenyl)-1-(phenyl)-2-ethenyl]bromobenzene (80 mg, 0.18 mmol) in 2.2 ml of THF. The mixture is agitated at −70° C. for 30 minutes and then the temperature is allowed to rise to −10° C. The mixture is hydrolysed by 3 ml of a 3N solution of HCl, extracted with ethyl ether (5×20 ml), dried over MgSO$_4$, filtered and evaporated. The raw product is recrystallised in methanol and after filtration and drying 50 mg of a white solid is obtained, the (E) compound [1-(5,6,7,8-tetrahydro-5,5,8,8-tetramethyl-2-naphthalenyl)-1-(phenyl)-2-ethenyl]benzene (compound CB04854) (yield= 75%).

m.pt. (° C.) 157

NMR$^1$H 200 MHz (CDCl$_3$): 1.25 (s, 6H, 2 Me); 1.30 (s, 6H, 2 Me); 1.65 (s, 4H, 2 —CH$_2$—); 6.80–7.10 (m, 6H, vinyl H and ArH); 7.15–7.35 (m, 8H, ArH).

MS EI 70 ev (m/z, % intensity): 366 (M$^+$, 100%); 351 (52), 179 (25).

HRMS EI 70 ev: M$_{tr}$=366.2339 for C$_{28}$H$_{30}$ M$_{th}$= 366.2347.

EXAMPLE 17

Preparation of the (E) acid 4-[1-(5,6,7,8-tetrahydro-5,5,8,8-tetramethyl-2-naphthalenyl)-1-(phenyl)-2-ethenyl]benzoic acid (compound CB01585) of formula

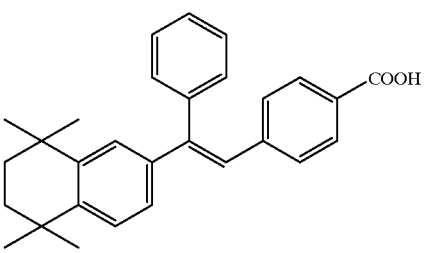

a) Preparation of the (E) compound 4-[1-(5,6,7,3-tetrahydro-5,5,8,8-tetramethyl-2-naphthalenyl)-1-(phenyl)-2-ethenyl]benzonitrile of formula

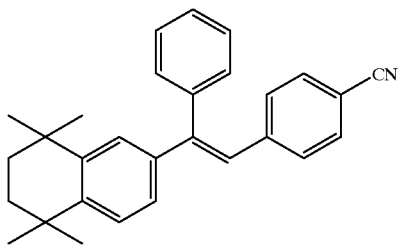

Copper cyanide (55 mg, 0.61 mmol) is added at ambient temperature to a solution of the (E) compound 4-[1-(5,6,7,8-tetrahydro-5,5,8,8-tetramethyl-2-naphthalenyl)-1-(phenyl)-2-ethenyl]bromobenzene (0.24 g, 0.53 mmol) in 1 ml of anhydrous DMF. The reaction medium is refluxed for 4 hours. After returning to ambient temperature, the reaction medium is diluted with ether (100 ml) and filtered on celite. The organic phase is washed with a saturated solution of NaHCO$_3$ (3×25 ml), dried over MgSO$_4$, filtered and evaporated. The raw product is; purified by flash chromatography on silica (eluent petroleum ether:ether=100:2). 30 mg of a solid is, obtained, the (E) compound 4-[1-(5,6,7,8-tetrahydro-5,5,8,8-tetramethyl-2-naphthalenyl)-1-(phenyl)-2-ethenyl]benzonitrile (yield=14%).

m.pt. (° C.) 191–193

NMR$^1$H 200 MHz (CDCl$_3$): 1.10 (s, 6H, 2 Me); 1.15 (s, 6H, 2 Me); 6.90 (s, 1H, vinyl H); 6.78–7.10 (m, 3H, ArH); 7.15–7.50 (m, 9H, ArH).

MS EI 70 ev (m/z, % intensity): 391 (M$^+$, 100%); 376 (90), 204 (40).

b) Preparation of the (E) acid 4-[1-(5,6,7,8-tetrahydro-5,5,8,8-tetramethyl-2-naphthalenyl)-1-(phenyl)-2-ethenyl] benzoic acid (compound CB01585)

A suspension of compound (E) 4-[1-(5,6,7,8-tetrahydro-5,5,8,8-tetramethyl-2-naphthalenyl)-1-(phenyl)-2-ethenyl] benzonitrile (30 mg, 0.076 mmol) in solution in alcoholic potassium hydroxide (42 mg, 0.75 mmol KOH in 0.1 ml H$_2$O and 1 ml EtOH) is heated to reflux under magnetic stirring for 12 hours. The ethanol is evaporated in a rotary evaporator, the product taken up in water (10 ml), acidified with 3N HCl and extracted with ether (3×15 ml). The ether phase is dried over MgSO$_4$, filtered and evaporated. The product is washed with pentane, filtered and dried. 20 mg of a white solid is obtained, the acid (E) 4-[1-(5,6,7,8-tetrahydro-5,5,8,8-tetramethyl-2-naphthalenyl)-1-(phenyl)-2-ethenyl]benzoic acid (compound CB01585) (yield=64%).

m.pt. (° C.)=240–241

NMR$^1$H 200 MHz (CDCl$_3$): 1.20 (s, 6H, 2 Me); 1.25 (s, 6H, 2 Me); 1.65 (s, 4H, 2 —CH$_2$—); 4.40–5.15 (m, 1H, mobile H); 6.80–7.40 (m, 11H); 7.60 (d, 2H, J 8.1 Hz).

MS EI 70 ev (m/z, % intensity): 410 (M$^+$, 100%); 395 (60.9), 223 (17.5); 178 (10.2).

HRMS EI 70 ev: M$_{tr}$=410.2238 for C$_{29}$H$_{30}$O$_2$ M$_{th}$=410.2246.

HPLC: Column Waters HR C$_{18}$, 8×100 mm, 6μ, Waters UV detector 486 to 260 nm, flow rate 3 ml/min, eluent MeOH:H$_2$O=90:10=0.1% TFA, acid (CB01585) tr=5.0 min 97.0%.

EXAMPLE 18

Preparation of the (Z) acid 2-[1-(5,6,7,8-tetrahydro-5,5,8,8-tetramethyl-2-naphthalenyl)-2-propenyl] pyridinyl-5-carboxylic acid (compound CB38416) of formula

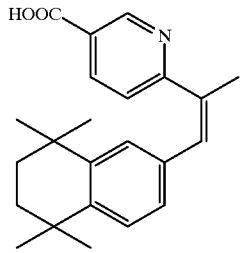

a) Preparation of the (E) and (Z) methyl 2-[1-(5,6,7,8-tetrahydro-5,5,8,8-tetramethyl-2-naphthalenyl)-2-propenyl] pyridinyl-5-carboxylates with respective following formulae

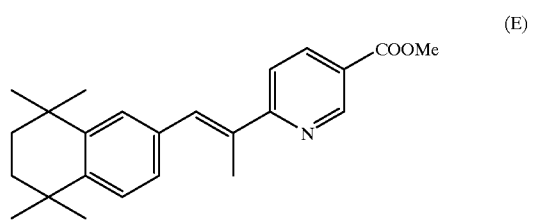

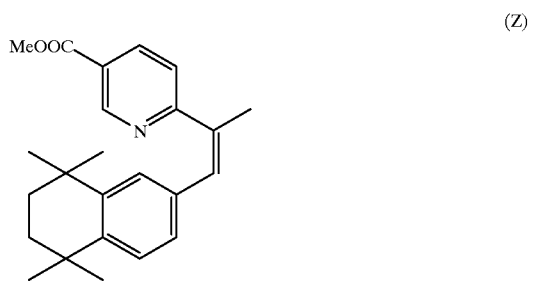

A solution of (5,6,7,8-tetrahydro-5,5,8,8-tetramethyl-2-naphthalenyl)-methyl triphenylphosphonium bromide (1.80 g, 3.3 mmol), NaH (Aldrich, 3.3 mmol) coming from 0.12 g of a 60% dispersion of NaH in oil, in anhydrous DMSO is agitated under argon for 30 minutes. Then a solution of methyl 2-acetylpyridine-5-carboxylate (0.50 g, 2.79 mmol) in 1 ml of DMSO is added. The solution is agitated for 70 hours at ambient temperature and then poured over ice (50 g). The product is extracted with ether (5×50 ml). The raw product is purified by flash chromatography on silica (eluent petroleum ether:ethyl ether=100:10). 0.64 g of a mixture of (E) and (Z) methyl 2-[1-(5,6,7,8-tetrahydro-5,5,8,8-tetramethyl-2-naphthalenyl)-2-propenyl]pyridinyl-5-carboxylate is obtained (yield=63%) in solid form (ratio (E):(Z) about 47:53 determined by NMR$^1$H 200 MHz).

NMR$^1$H 200 MHz (CDCl$_3$): 0.95 (s, 6×0.53 H, 2 Me, isomer Z); 1.18 (s, 6×0.53H, 2 Me, isomer Z); 1.28 (s, 12×0.47H, 4 Me, isomer E); 1.55 (s, 4×0.47H, 2 —CH$_2$—, isomer E); 1.68 (s, 4×0.53H, 2 —CH$_2$—, isomer Z); 2.25 (s, 3×0.47H, vinyl Me, isomer E); 2.37 (s, 3×0.47H, vinyl Me, isomer Z); 3.91 (s, 3×0.53H, —OMe, isomer Z); 3.93(s, 3×0.53H, —OMe, isomer E); 6.60–6.85 (m, 2H); 7.00–7.40 (m, 2H, ArH); 7.60 (m, 1H, ArH); 8.05–8.45 (m, 1H, ArH); 9.15–9.25 (m, 1H).

b) Acid (Z) 2-[1-(5,6,7,8-tetrahydro-5,5,8,8-tetramethyl-2-naphthalenyl)-2-propenyl]pyridinyl-5-carboxylic acid (compound CB38416)

A suspension of the (E) and (Z) methyl 2-[1-(5,6,7,8-tetrahydro-5,5,8,8-tetramethyl-2-naphthalenyl)-2-propenyl] pyridinyl-5-carboxylates (0.64 g, 1.76 mmol) in solution in alcoholic potassium hydroxide (0.5 g, 9 mmol KOH in 2.2 ml $H_2O$ and 19 ml MeOH) is heated to reflux under magnetic stirring for 12 hours. The methanol is evaporated in a rotary evaporator, the product taken up in water (50 ml), acidified with 3N HCl and extracted with ether (3×50 ml). The ether phase is dried over $MgSO_4$, filtered and evaporated. The raw product is purified by preparative HPLC on a Waters HR $C_{18}$ column (25×100 mm) with, as eluent MeOH:$H_2O$=85:15=0.1% TFA. 108 mg of a white solid is obtained, the acid (Z) 2-[1-(5,6,7,8-tetrahydro-5,5,8,8-tetramethyl-2-naphthalenyl)-2-propenyl]pyridinyl-5-carboxylic acid (compound CB38416) (yield=17%).

m.pt. (° C.)=234–236.

NMR[1]H 200 MHz (DMSO-$d_6$) 0.91 (s, 6H, 2 Me); 1.13 (s, 6H, 2 Me); 1.52 (s, 4H, 2 —$CH_2$—); 2.12 (s, 3H, vinyl Me); 3.40 (m, 1H); 6.67 (m, 1H, vinyl H); 6.70 (m, 1H, ArH); 7.10 (d, 1H, ArH, J 8 Hz); 7.24 (d, 2H, ArH J 8 Hz); 8.10 (dd, 1H, ArH J 2 Hz J 8 Hz); 9.15 (m, 1H, ArH).

MS EI 70 ev (m/z, % intensity): 349 (56%); 348 (100); 334 (39); 278 (11); 262 (19).

HRMS EI 70 ev: $M_{tr}$=349.1968 for $C_{23}H_{27}NO_2$ $M_{th}$=349.2042.

HPLC Waters HR $C_{18}$ column, 8×100 mm, 6μ, Waters UV detector 486 to 260 nm, flow rate 3 ml/min, eluent MeOH:$H_2O$=85:15=0.1% TEA, acid (CB38416) tr=2.8 min 98.5%.

EXAMPLE 19

Preparation of the acid (E) 5-[1-(5,6,7,8-tetrahydro-5,5,8,8-tetramethyl-2-naphthalenyl)-2-propenyl] pyridinyl-2-carboxylic acid (compound CB12273) of formula

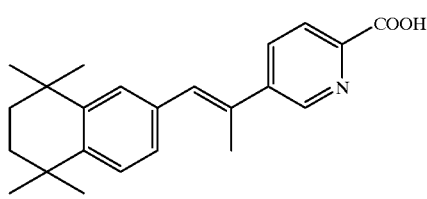

a) Preparation of the (E) and (Z) compounds 5-[1-(5,6,7,8-tetrahydro-5,5,8,8-tetramethyl-2-naphthalenyl)-2-propenyl]pyridinyl-2-(N,N,-diisopropyl)carboxamides of the following respective formulae

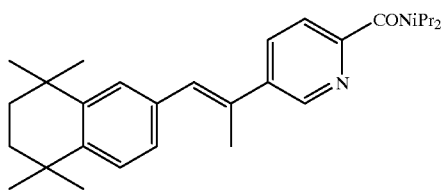

(E)

-continued

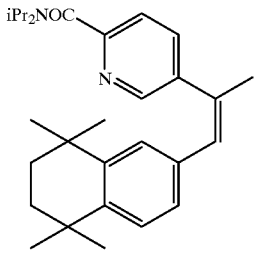

(Z)

A solution of tBuOK (2.13 g, 18.1 mmol) in 18.1 ml of THF is added at −70° C. to a solution of (5,6,7,8 -tetrahydro-5,5,8,8-tetramethyl-2-naphthalenyl) methyltriphenylphosphonium bromide (9.34 g, 17.2 mmol) in 25 ml of THF. The agitation is continued at −70° C. for 1 hour before adding N,N-diisopropyl-5-acetyl-pyridine-2-carboxamide at this temperature.

The reaction medium is brought to ambient temperature and the agitation continued for 90 hours. It is the hydrolysed at 0° C. by a solution of 3N HCl (30 ml). After returning to ambient temperature, it is extracted with ether, dried over $MgSO_4$, filtered and the solvents evaporated. The raw product is purified by flash chromatography on silica (eluent: petroleum ether:ether=100:25). 0.60 g of a solid is obtained, (E) 5-[1-(5,6,7,8-tetrahydro-5,5,8,8-tetramethyl-2-naphthalenyl)-2-propenyl]pyridinyl-2-(N,N,-diisopropyl) carboxamide and then 0.50 g of a white solid, (Z) 5-[1-(5,6,7,8-tetrahydro-5,5,8,8-tetramethyl-2-naphthalenyl)-2-propenyl]pyridinyl-2-(N,N,-diisopropyl)carboxamide and 0.78 g of a mixture of the two isomers (overall yield=60%).

Isomer (E)

NMR[1]H 200 MHz ($CDCl_3$): 1.05–1.25 (s, 6H, 2 Me); 1.30 (s, 12H, 4 Me); 1.40–1.60 (m, 6H, 2 Me); 1.70 (s, 4H, 2 —$CH_2$—); 2.30 (s, 3H, Me); 3.50 (m, 1H, —CH—N—); 3.90 (m, 1H, —CH—N—); 6.80 (m, 1H, vinyl H); 7.10–7.18 (m, 1H, ArH); 7.25–7.35 (m, 2H, ArH); 7.45 (d, 1H, ArH, J 8 Hz); 7.62 (dd, 1H, ArH J 2 Hz and J 8 Hz); 8.70 (m, 1H, ArH).

Isomer (Z)

NMR[1]H 200 MHz ($CDCl_3$): 0.97 (s, 6H, 2 Me); 1.05–1.25 (s, 12H, 4 Me); 1.40–1.70 (m, 10H, 2 —$CH_2$— and 2 Me); 2.22 (s, 3H, Me); 3.47 (m, 1H, —CH—N—); 4.92 (m, 1H, —CH—N—); 6.52 (s, 1H, vinyl H); 6.72 (dd, 1H, ArH J 2 Hz and J 8 Hz); 6.85 (m, 1H, ArH); 7.05 (d, 1H, ArH J 8 Hz); 7.30–7.40 (m, 1H, ArH); 7.57 (dd, 1H, ArH J 2 Hz J 8 Hz); 8.37 (m, 1H, ArH).

b) Preparation of the (E) compound 5-[1-(5,6,7,8-tetrahydro-5,5,8,8-tetramethyl-2-naphthalenyl)-2-propenyl]-2-formylpyridine of formula

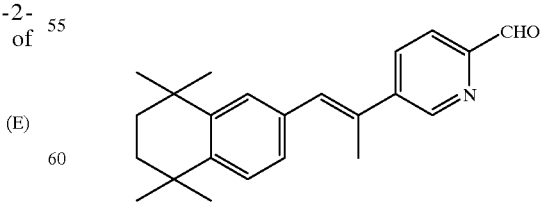

A 1.5 M solution of di-isobutyl aluminium hydride in toluene (1 ml, 1.47 mmol) is added at −70° C. to a solution of (E) 5-[1-(5,6,7,8-tetrahydro-5,5,8,8-tetramethyl-2-naphthalenyl)-2-propenyl]pyridinyl-2-(N,N,-diisopropyl)

carboxamide (0.51 g, 1.40 mmol) in 7 ml of THF. The mixture is agitated at this temperature for 30 minutes and hydrolysed by an aqueous solution of 3N HCl (5 ml). After rising to ambient temperature, it is extracted with dichloromethane (5×20 ml) and tine organic phase dried over MgSO$_4$, filtered and evaporated. The raw product is purified by flash chromatography on silica (eluent petroleum ether:ether=100:20). 0.14 g of a white solid is obtained, (E) 5-[1-(5,6,7,8-tetrahydro-5,5,8,8-tetramethyl-2-naphthalenyl)-2-propenyl]-2-formylpyridine (yield=29%).

NMR$^1$H 200 MHz (CDCl$_3$): 1.27 (s, 12H, 4 Me); 1.67 (s, 4H, 2 —CH$_2$—); 2.30 (s, 3H, Me); 6.93 (s, 1H, vinyl H); 7.10–7.20 (m, 1H, ArH); 7.28–7.37 (m, 2H, ArH); 7.93 m, 2H, ArH); 8.90 (m, 1H, ArH); 10.07 (s, 1H, —CHO).

c) Preparation of the (Z) compound 5-[1-(5,6,7,8-tetrahydro-5,5,8,8-tetramethyl-2-naphthalenyl)-2-propenyl]-2-formylpyridine of formula

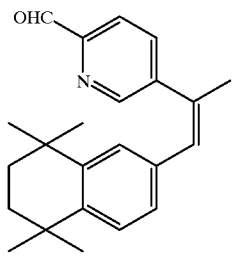

A 1.5 M solution of di-isobutyl aluminium hydride in toluene (0.5 ml, 0.75 mmol) is added at −70° C. to a solution of (Z) 5-[1-(5,6,7,8-tetrahydro-5,5,8,8-tetramethyl-2-naphthalenyl)-2-propenyl]pyridinyl-2-(N,N,-diisopropyl) carboxamide (0.26 g, 0.71 mmol) in 3.5 ml of THF. The mixture is agitated at this temperature for 30 minutes and is hydrolysed by an aqueous solution of 3N HCl (5 ml). After rising to ambient temperature, it is extracted with dichloromethane (5×20 ml) and the organic phase dried over MgSO$_4$, filtered and evaporated. The raw product is purified by flash chromatography on silica (eluent petroleum ether:ether=100:20). 0.15 g of a solid is obtained, (Z) 5-[1-(5,6,7,8-tetrahydro-5,5,8,8-tetramethyl-2-naphthalenyl)-2-propenyl]-2-formylpyridine (yield=63%).

NMR$^1$H 200 MHz (CDCl$_3$): 0.93 (s, 6H, 2 Me); 1.20 (s, 6H, 2 Me); 1.55 (s, 4H, 2 —CH$_2$—); 2.20 (s, 3H, Me); 6.62 (s, 1H, vinyl H); 6.67–6.78 (m, 2H, ArH); 7.05 (d, 1H, ArH J 8 Hz); 7.65–7.72 (m, 1H, ArH); 7.87 (d, 1H, ArH J 8 Hz); 8.55 (m, 1H, ArH); 9.98 (s, 1H, —CHO).

d) Preparation of the (E) and (Z) methyl 5-[1-(5,6,7,8-tetrahydro-5,5,8,8-tetramethyl-2-naphthalenyl)-2-propenyl] pyridinyl-2-carboxylates of the following respective formulae

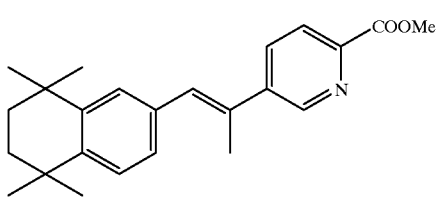

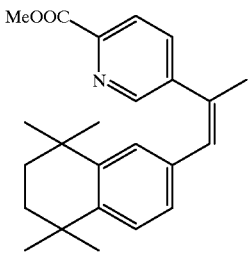

0.185 ml of acetic acid, manganese oxide (3.98 g, 43.3 mmol) and sodium cyanide (0.53 g, 10.85 mmol) was added successively at ambient temperature to a solution of a mixture of the (E) and (Z) 5-[1-(5,6,7,8-tetrahydro-5,5,8,8-tetramethyl-2-naphthalenyl)-2-propenyl]-2-formylpyridines (0.72 g, 2.17 mmol) in 60 ml of methanol. The reaction medium is agitated at this temperature for 15 hours. It is filtered on paper, evaporated, taken up in 20 ml water, extracted with ether (5×50 ml), dried over MgSO$_4$, filtered and evaporated. The raw product is purified by flash chromatography on silica (eluent petroleum ether:ether 100:20 then 100:25). After evaporation of the fractions, 0.13 g of a solid is obtained, (Z) methyl 5-[1-(5,6,7,8-tetrahydro-5,5,8,8-tetramethyl-2-naphthalenyl)-2-propenyl]pyridinyl-2-carboxylate (yield=16%) and then 0.11 g of a solid, (E) methyl 5-[1-(5,6,7,8-tetrahydro-5,5,8,8-tetramethyl-2-naphthalenyl)-2-propenyl]pyridinyl-2-carboxylate (yield=14%).

Isomer (E)

NMR$^1$H 200 MHz (CDCl$_3$): 1.25 (s, 12H, 4 Me); 1.70 (s, 4H, 2 —CH$_2$—); 2.35 (s, 3H, Me); 4.00 (s, 3H, —OMe); 6.90 (s, 1H, vinyl H); 7.12 (dd, 1H, ArH J 2 Hz J 8 Hz); 7.25–7.35 (m, 2H, ArH); 7.87 (dd, 1H, ArH J 2 Hz J 8 Hz); 8.10 (d, 1H, ArH J 8 Hz); 8.85 (m, 1H, ArH).

Isomer (Z)

NMR$^1$H 200 MHz (CDCl$_3$): 0.90 (s, 6H, 2 Me); 1.17 (s, 6H, 2 Me); 1.52 (s, 4H, 2 —CH$_2$—); 2.40 (s, 3H, Me); 4.00 (s, 3H, —OMe); 6.50–6.85 (s, 3H, vinyl H and ArH); 6.95–7.15 (m, 1H, ArH); 7.20–7.75 (m, 2H, ArH); 8.02 (d, 1H, ArH J 8 Hz); 8.47 (m, 1H, ArH).

e) Preparation of the (E) acid 5-[1-(5,6,7,8-tetrahydro-5,5,8,8-tetramethyl-2-naphthalenyl)-2-propenyl]pyridinyl-2-carboxylic acid (CB12273)

A suspension of the (E) methyl 5-[1-(5,6,7,8-tetrahydro-5,5,8,8-tetramethyl-2-naphthalenyl)-2-propenyl]pyridinyl-2-carboxylate (80 mg, 0.22 mmol) in solution in alcoholic potassium hydroxide (120 mg, 2.18 mmol KOH in 0.3 ml H$_2$O and 2.4 ml MeOH) is heated to reflux under magnetic stirring for 3 hours 30 minutes. The methanol is evaporated in a rotary evaporator, the product taken up in water (10 ml), acidified with 3N HCl and extracted with ether (3×20 ml). The ether phase is dried over MgSO$_4$, filtered and evaporated. The raw product is washed in pentane and then filtered. 70 mg of a white solid is obtained, the acid (E) 5-[1-(5,6,7,8-tetrahydro-5,5,8,8-tetramethyl-2-naphthalenyl)-2-propenyl]pyridinyl-2-carboxylic acid (compound CB12273) (yield=91%).

m.pt. (° C.)=192

NMR$^1$H 200 MHz (CDCl$_3$): 1.28 (s, 12H, 4 Me); 1.69 (s, 4H, 2 —CH$_2$—); 2.34 (s, 3H, Me); 6.85–7.05 (m, 1H, vinyl H); 7.10–7.20 (m, 1H, ArH); 7.30–7.40 (m, 2H, ArH); 8.0–8.10 (m, 1H, ArH); 8.15–8.30 (m, 1H, ArH); 8.75–8.95 (m, 1H, ArH).

MS EI 70 ev (m/z, % intensity): 349 (M+, 100%); 334 (96); 316 (20); 190 (20).

HRMS EI 70 ev: $M_{tr}$=349.2045 for $C_{23}H_{27}NO_2$ $M_{th}$= 349.2042.

IR (cm$^{-1}$): 3738; 2994; 1706; 1578; 1464.

EXAMPLE 20

Preparation of the (E) acid 2-[1-(5,6,7,8-tetrahydro-5,5,8,8-tetramethyl-2-naphthalenyl)-2-propenyl)] thienyl-4-carboxylic acid compound (CB80660) of formula

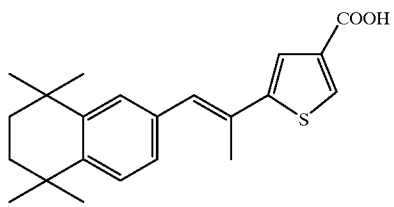

a) Preparation of 4-bromo-2-(1'-hydroxyethyl)thiophene

A solution of 4-bromo-2-thiophenecarboxaldehyde (Aldrich, 1.20 g, 6.28 mmol) in 15 ml of anhydrous ethyl ether is brought to −70° C. in a flask fitted with a thermometer, under an atmosphere of argon and with magnetic stirring. Then a 1.6 M solution of MeLi in ether (4.12 ml, 6.59 mmol) is added drop by drop between −70° C. and −60° C. The reaction is followed by CCM (eluent ether:petroleum ether=20:80). The mixture is hydrolysed in the cold with 5 ml of saturated NH$_4$Cl solution, 20 ml of distilled water is added and the mixture is extracted with ether (3×40 ml). The ether phase is dried over MgSO$_4$, filtered and evaporated to obtain 1.28 g of a slightly yellowish oil, 4-bromo-2-(1'-hydroxyethyl)thiophene (gross yield= 98.5%).

NMR$^1$H 200 MHz (CDCl$_3$): 1.53 (d, 3H, Me J 6 Hz); 2.3–2.5 (s broad, 1H mobile, —OH); 5.02 (q, 1H, —CHOH J 6.0 Hz); 6.84 (d, 1H, ArH J 1.5 Hz); 7.09 (d, 1H, ArH J 1.5 Hz).

b) Preparation of 4-bromo-2-acetyl-thiophene

A solution of raw 4-bromo-2-(1'-hydroxyethyl)thiophene (1.28 g, 6.18 mmol) and PCC (2.6 g, 13.26 mmol) in 20 ml of dichloromethane is put into a flask fitted with magnetic stirring and under an atmosphere of argon. It is agitated vigorously for 2 hours at ambient temperature, the reaction medium becoming progressively black. It is then filtered on a column of florisil (eluent ether), the solvent evaporated and the raw product produced is purified by flash chromatography on silica (eluent pure petroleum ether). 1.10 g of a white solid is obtained 4-bromo-2-acetyl-thiophene (yield=87%).

NMR$^1$H 200 MHz (CDCl$_3$): 2.50 (s, 3H, Me); 7.50 (s, 1H, ArH); 7.54 (s, 1H, ArH).

c) Preparation of the (E) and (Z) 2-[1-(5,6,7,8-tetrahydro-5,5,8,8-tetramethyl-2-naphthalenyl)-2-propenyl)]-4-bromothiophenes of the following respective formulae

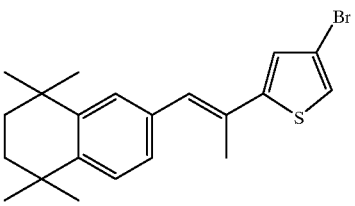

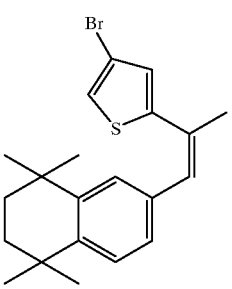

(5,6,7,8-tetrahydro-5,5,8,8-tetramethyl-2-naphthalenyl) methyl-triphenylphosphonium bromide (7.00 g, 12.56 mmol) is weighed into a twin-necked 100 ml flask fitted with a thermometer, magnetic stirring and under an atmosphere of argon and dissolved in 20 ml of anhydrous THF. 1M tBuOK in THF is added at −70° C. and the agitation continued at −70° C. for 1 hour. Then the 4-bromo-2-acetyl-thiophene (1.29 g, 6.28 mmol) in solution in 15 ml of anhydrous THF is added and the reaction medium is allowed to slowly come back to ambient temperature and the agitation is continued for 72 hours. Then the reaction mixture is poured into an ice/water solution and extracted with ether (5×50 ml). The organic phase is dried with MgSO$_4$, filtered and evaporated to give a raw product that is purified by flash chromatography on silica (eluent pure petroleum ether). 1.97 g of a colourless oil is obtained made up of a mixture of the (E) and (Z) isomers, the 2-[1-(5,6,7,8-tetrahydro-5,5,8,8-tetramethyl-2-naphthalenyl)-2-propenyl)]-4-bromothiophenes (overall yield=80%) (ratio (E):(Z)=60:40 determined by NMR$^1$H).

NMR$^1$H 200 MHz (CDCl$_3$): 1.15 (s, 6×0.40 H, 2 Me, isomer Z); 1.25 (s, 6×0.40H, 2 Me, isomer Z); 1.30 (s, 12×0.60H, 4 Me, isomer E); 1.62 (s, 4×0.40H, 2 —CH$_2$—, isomer Z); 1.70 (s, 4×0.60H, 2 —CH$_2$, isomer E); 2.20 (d, 3×0.40H, Me J 2.9 Hz, isomer Z); 2.27 (d, 3×0.60H, Me J 2.9 Hz, isomer E); 6.51 (s broad, 1×0.40H, vinyl H, isomer Z); 6.75–7.35 (m, 5H, ArH isomers E and Z and 1×0.60H, vinyl H, isomer E).

d) Preparation of (E) methyl 2-[1-(5,6,7,8-tetrahydro-5,5,8,8-tetramethyl-2-naphthalenyl)-2-propenyl)]thienyl-4-carboxylate of the following formula

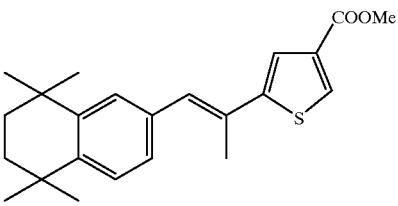

A solution of (E) and (Z) 2-[1-(5,6,7,8-tetrahydro-5,5,8, 8-tetramethyl-2-naphthalenyl)-2-propenyl)]-4- bromothiophenes (1.22 g, 3.13 mmol) in 12.5 ml of anhydrous THF is put into a 25 ml flask fitted with magnetic stirring, a thermometer and under an atmosphere of argon. The reaction medium is brought to −70° C. and a 1.7 M solution of t-butyl lithium in pentane (3.78 ml, 6.42 mmol) is added drop by drop. The reaction medium darkens and it is agitated for 20 minutes at −70° C. and then methyl chloroformate (1.5 eq., 4.70 mmol) is added and the reaction medium is brought to ambient temperature during 30 minutes. At 0° C., 25 ml of distilled water is added and the mixture extracted with ether (3×50 ml). The organic phase is dried over MgSO₄, filtered and evaporated. A raw product is obtained that is purified by flash chromatography on silica (eluent petroleum ether then ether:petroleum ether=2:98). 0.10 g of a white solid is obtained (E) methyl 2-[1-(5,6,7,8-tetrahydro-5,5,8,8-tetramethyl-2-naphthalenyl)-2-propenyl)]thienyl-4-carboxylate after recrystallisation in hexane (yield=8%).

NMR¹H 200 MHz (CDCl₃): 1.28 (s, 12H, Me); 1.68 (s, 4H, 6,7-CH₂—); 2.29 (d, 3H, Me J 2.9 Hz); 3.87 (s, 3H, —OMe); 7.02–7.33 (m, 5H, ArH and vinyl H); 7.68 (d, 1H, ArH J 10 Hz).

e) Preparation of the acid (E) 2-[1-(5,6,7,8-tetrahydro-5,5,8,8-tetramethyl-2-naphthalenyl)-2-propenyl)]thienyl-4-carboxylic acid (compound CB80660)

A suspension of (E) methyl 2-[1-(5,6,7,8-tetrahydro-5,5,8,8-tetramethyl-2-naphthalenyl)-2-propenyl)]thienyl-4-carboxylate (88 mg, 0.24 mmol) in 3 ml of methanol and 1.5 ml of a 5N aqueous solution of KOH was put into a 10 ml flask fitted with a condenser and magnetic stirring. It was brought to reflux for 6 hours, the reaction medium was cooled, acidified with 3N HCl to pH 1 and extracted with ether (3×30 ml). The ether phase was dried over MgSO₄, filtered and evaporated. The raw product is washed in a minimum of hexane and 40 mg of a white solid, (E) 2-[1-(5,6,7,8-tetrahydro-5,5,8,8-tetramethyl-2-naphthalenyl)-2-propenyl)]thienyl-4-carboxylic acid (compound CB80660) is obtained (yield=47%).

m.pt. (° C.)=232–235

NMR¹H 200 MHz (CDCl₃): 1.28 (s, 12H, 4 Me); 1.69 (s, 4H, —CH₂—); 2.30 (s, 3H, Me); 7.00–7.35 (m, 5H, ArH and vinyl H), 7.77 (d, 1H, ArH J 10 Hz).

MS EI 70 ev (m/z, % intensity): 354 (M⁺, 100%); 339 (M⁺—CH₃, 76); 297 (5); 155 (5).

HRMS EI 70 ev: $M_{tr}$=354.1661 for $C_{22}H_{26}O_2S$ $M_{th}$=364.1654.

IR (NaCl discs, cm⁻¹): 1668 (C=O).

HPLC: ODS Column Ultrasphere, 5μ, 250×4.6 mm, UV detection, 260 nm, flow rate 1 ml/min, eluent MeOH:H₂O= 100:0=0.1% TFA, acid (CB80660) tr=4.6 min 98.9%, impurity tr=4.1 min 1.1%.

EXAMPLES 21 AND 22

Preparation of the acid (Z) 2-[1-(5,6,7,8-tetrahydro-5,5,8,8-tetramethyl-2-naphthalenyl)-2-propenyl)] thienyl-5-carboxylic acid (compound CB30382) of formula

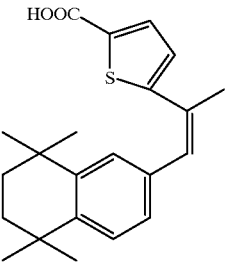

Preparation of the acid (E) 2-[1-(5,6,7,8-tetrahydro-5,5,8,8-tetramethyl-2-naphthalenyl)-2-propenyl)]thienyl-5-carboxylic acid (compound CB38973) of formula:

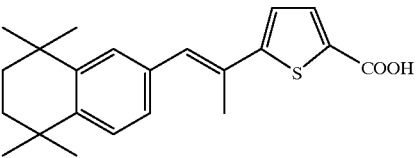

a) (E) and (Z) 2-[1-(5,6,7,8-tetrahydro-5,5,8,8-tetramethyl-2-naphthalenyl)-2-propenyl)]-5-bromothiophenes of the following respective formulae (E)

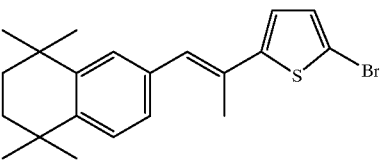

(Z)

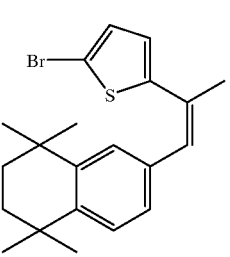

A 1M solution of potassium tert-butylate in THF (6.50 ml, 6.50 mmol) is added at −70° C. to a solution of (5,6,7,8-tetrahydro-5,5,8,8-tetramethyl-2-naphthalenyl)methyl-triphenylphosphonium bromide (3.34 g, 6.15 mmol) in 9 ml of THF. Agitation is continued at −70° C. for 1 hour before adding 2-acetyl-5-bromothiophene (0.63 g, 3.10 mmol). The reaction medium is brought to ambient temperature and agitated for 20 hours. Then the mixture is hydrolysed at 0° C. by a solution of 3N HCl. After returning to ambient temperature, it is extracted with ether, dried over MgSO₄, filtered and the solvent, evaporated. The raw product is purified by flash chromatography on silica (eluent petroleum ether). 0.46 g of the (E) and (Z) 2-[1-(5,6,7,8-tetrahydro-5, 5,8,8-tetramethyl-2-naphthalenyl)-2-propenyl)]-5-bromothiophenes are obtained (yield=38%) (ratio (Z):(E)=70:30 determined by NMR$^1$H).

NMR$^1$H 200 MHz (CDCl$_3$): 1.25–1.40 (m, 12H 4 Me); 1.65 (s, 0.3×4H, 2 —CH$_2$— isomer E); 1.70 (s, 0.7×4H, 2 —CH$_2$— isomer Z); 2.18 (s, 0.3×3H, vinyl Me isomer E); 2.25 (s, 0.7×3H, vinyl Me isomer Z); 6.45 (s, 0.30×1H, vinyl H isomer E); 6.67 (d, 0.7×1H, vinyl H isomer Z J 5 Hz); 6.80–6.87 (m, 2H, AH); 6.92–7.00 (m, 1H, ArH); 7.05–7.30 (m, 2H, ArH).

b) Preparation of the acids (E) and (Z) 2-[1-(5,6,7,8-tetrahydro-5,5,8,8-tetramethyl-2-naphthalenyl)-2-propenyl)]thienyl-5-carboxylic acids, respectively designated compounds CB38973 and CB30382 and corresponding to the formulae

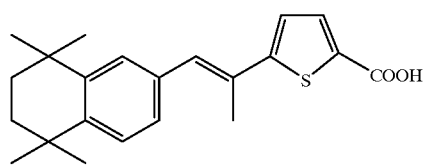

(E)

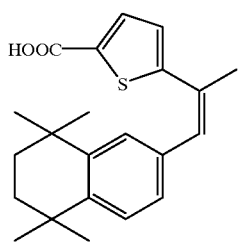

(Z)

A 1.6 M solution of n-butyl lithium in hexane (0.8 ml, 1.18 mmol) is added at −70° C. to a solution of the (E) and (Z) 2-[1-(5,6,7,8-tetrahydro-5,5,8,8-tetramethyl-2-naphthalenyl)-2-propenyl)]-5-bromothiophenes (0.46 g 1.18 mmol) in 14 ml of THF and agitated for 30 minutes. A stream of carbon dioxide is bubbled through the reaction medium and it is agitated for 30 minutes at −70° C. The temperature is allowed to rise to −10° C. and the mixture is hydrolysed by a solution of 3N HCl (15 ml). It is extracted with ether, dried over MgSO$_4$, filtered and evaporated. The raw product is purified by preparative HPLC on a Waters HR C$_{18}$ column (25×100 mm) with eluent MeOH:H$_2$O=90:10=0.1% TFA. 101.2 mg of a yellowish solid is obtained, the (E) 2-[1-(5,6,7,8-tetrahydro-5,5,8,8-tetramethyl-2-naphthalenyl)-2-propenyl)]thienyl-5-carboxylic acid (CB38973) (yield=25%) and 62.9 mg of a yellowish solid (Z) 2-[1-(5,6,7,8-tetrahydro-5,5,8,8-tetramethyl-2-naphthalenyl)-2-propenyl)]thienyl-5-carboxylic acid (CB30382) (yield=16%).

Acid (Z) 2-[1-(5,6,7,8-tetrahydro-5,5,8,8-tetramethyl-2-naphthalenyl)-2-propenyl)]thienyl-5-carboxylic acid (CB30382):

m.pt. (° C.)=165–167

NMR$^1$H 200 MHz (CDCl$_3$): 1.09 (s, 6H, 2 Me); 1.23 (s, 6H, 2 Me); 1.62 (s, 4H, 2 —CH$_2$—); 2.22 (s, 3H, Me); 6.57 (s, 1H, vinyl H); 6.87 (m, 2H, ArH); 7.06 (m, 1H, ArH); 7.18 (m, 1H, ArH); 7.64 (d, 1H, ArH J 1.9 Hz).

MS EI 70 ev (m/z, % intensity): 354 (100%); 339 (92).

HRMS EI 70 ev: M$_{tr}$=354.1669 for C$_{22}$H$_{26}$O$_2$S M$_{th}$=354.1654.

HPLC Waters HR C$_{18}$ column, 8×100 mm, 6µ, Waters UV detector 486 to 260 nm, flow rate 2 ml/min, eluent MeOH:H$_2$O=90:10=0.1% TFA, acid (CB30382) tr=4.4 min 97.5%; impurity tr=6.0 min 1.8%.

Acid (E) 2-[1-(5,6,7,8-tetrahydro-5,5,8,8-tetramethyl-2-naphthalenyl)-2-propenyl)]thienyl-5-carboxylic acid (CB38973)

m.pt. (° C.)=239

NMR$^1$H 200 MHz (CDCl$_3$): 1.28 (s, 12H, 4 Me); 1.66 (s, 4H, 2 —CH$_2$—); 2.30 (s, 3H, Me); 7.15 (m, 3H, vinyl H and ArH); 7.28 (m, 2H, ArH); 7.77 (d, 1H, ArH J 2 Hz).

MS EI 70 ev (m/z, % intensity): 354 (100%); 339 (95).

HRMS EI 70 ev: M$_{tr}$=354.1667 for C$_{22}$H$_{26}$O$_2$S M$_{th}$=354.1654.

HPLC Waters HR C$_{18}$ column, 8×100 mm, 6µ, Waters UV detector 486 to 260 nm, flow rate 3 ml/min, eluent MeOH:H$_2$O=90:10=0.1% TFA, acid (CB38973) tr=4.1 min 98.1%; impurity tr=3.1 min 1.5%.

EXAMPLE 23

Preparation of the acid (Z) 5-[1-(5,6,7,8-tetrahydro-5,5,8,8-tetramethyl-2-naphthalenyl)-2-propenyl)]-isoxazole-3-carboxylic acid (CB73069) and the acid (E) 5-[1-(5,6,7,8-tetrahydro-5,5,8,8-tetramethyl-2-naphthalenyl)-2-propenyl)]-isoxazole-3-carboxylic acid (CB57201)

(E) and (Z) ethyl 5-[1-(5,6,7,8-tetrahydro-5,5,8,8-tetramethyl-2-naphthalenyl)-2-propenyl)]-isoxazole-3-carboxylates A 1M solution of t-BuOK in THF (6.50 ml, 6.50 mmol) is added at −70° C. to a solution of (5,6,7,8-tetrahydro-5,5,8,8-tetramethyl-2-naphthalenyl)-6-methyltriphenylphosphonium bromide (4.75 g, 8.74 mmol) in 10 ml of anhydrous THF. The agitation is continued at −70° C. for 1 hour before adding a solution of ethyl acetylisoxazole- 3-carboxylate (0.80 g, 4.37 mmol) in 5 ml of anhydrous THE. The reaction medium is brought to ambient temperature and agitated for 16 hours. Then the reaction medium is poured over an ice-water mixture (150 ml) and then extracted with ether (3×70 ml), dried over MgSO$_4$, filtered and the solvents evaporated. The raw product is purified by flash chromatography on silica (eluent ether:petroleum ether=2:98 then 5:95). 0.37 g of a yellowish oil is obtained, (Z) ethyl 5-[1-(5,6,7,8-tetrahydro-5,5,8,8-tetramethyl-2-naphthalenyl)-2-propenyl)]-isoxazole-3-carboxylate (yield=23%) and then 0.65 g of a yellowish solid, (E) ethyl 5-[1-(5,6,7,8-tetrahydro-5,5,8,8-tetramethyl-2-naphthalenyl)-2-propenyl)]-isoxazole-3-carboxylate (yield=40.5%).

Isomer (Z):

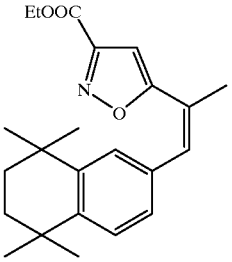

NMR$^1$H 200 MHz (CDCl$_3$): 1.16 and 1.25 (2s, 12H, 5,5,8,8-Me); 1.31 (t, 3H, Me J 7.1 Hz); 1.64 (s, 4H, 6,7-CH$_2$—); 2.23 (d, 3H, vinyl Me J 1.5 Hz); 4.37 (q, 2H, —OCH$_2$— J 7.1 Hz); 6.29 (s, 1H, isoxazole H); 6.74 (s broad, 1H, vinyl H); 6.91 (dd, 1H, ArH J 1.8 Hz J 8.1 Hz); 7.11 (d, 1H, ArH J 1.8 Hz); 7.24 (s, 1H, ArH).

MS EI 70 ev (m/z, % intensity): 367 (M⁺, 48%); 352 (M⁺—CH₃, 100); 253 (17); 74 (12); 59 (21); 57 (15); 55 (15).

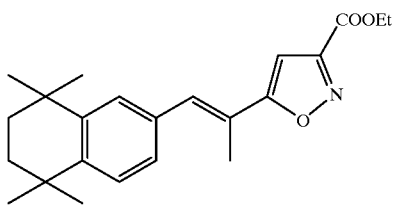

Isomer (E)

m.pt. (° C.)=89.

NMR¹H 200 MHz (CDCl₃): 1.29 and 1.31 (2s, 12H, 5,5,8,8-Me); 1.42 (t, 3H, Me J 7.1 Hz); 1.68 (s, 4H, 6,7-CH₂—); 2.26 (d, 3H, vinyl Me J 1.4 Hz); 4.44 (q, 2H, —OCH₂— J 7.1 Hz); 6.64 (s, 1H, isoxazole H); 7.19 (dd, 1H, ArH J 1.7 Hz J 8.2 Hz); 7.27–7.40 (m, 3H, 2 ArH and vinyl H).

MS EI 70 ev (m/z, % intensity): 367 (M⁺, 62%); 352 (M⁺—CH₃, 100); 253 (18).

b) (Z) 5-[1-(5,6,7,8-tetrahydro-5,5,8,8-tetramethyl-2-naphthalenyl)-2-propenyl)]-isoxazole-3-carboxylic acid (CB73069)

(Z) ethyl 5-[1-(5,6,7,8-tetrahydro-5,5,8,8-tetramethyl-2-naphthalenyl)-2-propenyl)]-isoxazole-3-carboxylate (0.35 g, 0.95 mmol) in suspension in 6.6 ml ethanol and 1.1 ml of distilled water was put into a 25 ml flask fitted with a condenser and under magnetic stirring. Potassium hydroxide (0.53 g, 9.5 mmol) is added and the reaction medium is brought to reflux for 8 hours. After cooling the reaction medium, it is acidified with 3N HCl to pH=1 and extracted with ether (3×50 ml). The ether phase is dried over MgSO₄, filtered and evaporated. The raw product is purified by preparative HPLC on a Waters HR column C₁₈ (25×100 mm) with eluent MeOH:H₂O=85:15=0.1% TFA. 0.31 g of a white solid is obtained, (Z) 5-[1-(5,6,7,8-tetrahydro-5,5,8,8-tetramethyl-2-naphthalenyl)-2-propenyl)]-isoxazole-3-carboxylic acid (CB73069) (yield=96%).

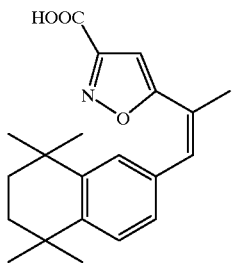

m.pt. (° C.)=114

NMR¹H 200 MHz (CDCl₃): 1.16 and 1.25 (2s, 12H, 5,5,8,8-Me); 1.65 (s, 4H, 6,7-CH₂—); 2.24 (s, 3H, vinyl Me); 6.33 (s, 1H, isoxazole H); 6.77 (s, 1H, vinyl H); 6.92 (d, 1H, ArH J 1.8 Hz); 7.12 (s, 1H, ArH); 7.24 (d, 1H, ArH J 8.0 Hz); 7.50 (s broad, 1H, —COOH).

MS EI 70 isobutane (m/z, % intensity) 340 (M⁺+1, 100%); 296 (57).

HRMS (FAB+NOBA): MH⁺_tr=340.1916 for C₂₁H₂₅NO₃ MH⁺_th=340.1913.

HPLC: Waters HR C₁₈ column, 8×100 mm, 6μ, Waters UV detector 486 to 260 nm, flow rate 3 ml/min, eluent MeOH:H₂O=85:15=0.1% TFA, acid (CB73069) tr=3.37 min 97.6%.

c) (E) 5-[1-(5,6,7,8-tetrahydro-5,5,8,8-tetramethyl-2-naphthalenyl)-2-propenyl)]-isoxazole-3-carboxylic acid (CB57201)

(E) ethyl 5-[1-(5,6,7,8-tetrahydro-5,5,8,8-tetramethyl-2-naphthalenyl)-2-propenyl)]-isoxazole-3-carboxylate (0.70 g, 1.90 mmol) in suspension in 13.2 ml ethanol and 2.2 ml of distilled water was put into a 50 ml flask fitted with a condenser and under magnetic stirring. Potassium hydroxide (1.06 g, 19.00 mmol) is added and the reaction medium is brought to reflux for 1 hour 15 minutes. After cooling the reaction medium, it is acidified with 3N HCl to pH=1 and extracted with ether (3×50 ml). The ether phase is dried over MgSO₄, filtered and evaporated. The raw product is taken up in a minimum of ethyl ether and hexane is added until precipitation. After filtration and drying, 0.36 g of a white solid is obtained, (E) 5-[1-(5,6,7,8-tetrahydro-5,5,8,8-tetramethyl-2-naphthalenyl)-2-propenyl)]-isoxazole-3-carboxylic acid (CB57201) (yield=96%).

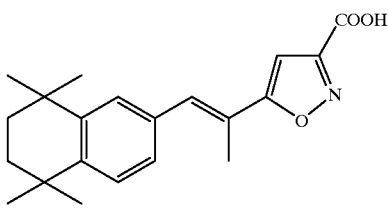

m.pt. (° C.)=205

NMR¹H 200 MHz (CDCl₃): 1.29 and 1.30 (2s, 12H, 5,5,8,8-Me); 1.69 (s, 4H, 6,7-CH₂—); 2.28 (d, 3H, vinyl Me J 1.1 Hz); 6.71 (s, 1H, isoxazole H); 7.19 (dd, 1H, ArH J 0.8 Hz J 4.0 Hz); 7.25–7.45 (m, 3H, ArH and vinyl H).

MS FAB+NOBA (m/z, % intensity): 340 (MH⁺, 100%); 324 (31); 154 (49); 136 (40).

HRMS (FAB+NOBA): MH⁺_tr=340.1917 for C₂₁H₂₅NO₃ MH⁺_th=340.1913.

HPLC: Waters HR C₁₈ column, 8×100 mm, 6μ, Waters UV detector 486 to 260 nm, flow rate 3 ml/min, eluent MeOH:H₂O=85:15=0.1% TFA, acid (CB57201) tr=5.21 min 98.8%.

EXAMPLE 24

Preparation of (Z) 5-[1-(5,6,7,8-tetrahydro-3,5,5,8,8-pentamethyl-2-naphthalenyl)-2-propenyl)]isoxazole-3-carboxylic acid (CB54647) and (E) 5-[1-(5,6,7,8-tetrahydro-3,5,5,8,8-pentamethyl-2-naphthalenyl)-2-propenyl)]isoxazole-3-carboxylic acid (CB 82718)

a) (E) and (Z) ethyl 5-[1-(5,6,7,8-tetrahydro-3,5,5,8,8-pentamethyl-2-naphthalenyl)-2-propenyl)]isoxazole-3-carboxylates A 1M solution of t-BuOK in THF (8.73 ml, 8.73 mmol) is added at −70° C. to a solution of (5,6,7,8-tetrahydro-3,5,5,8,8-pentamethyl-2-naphthalenyl)-6-methyltriphenylphosphonium bromide (4.86 g, 8.73 mmol) in 10 ml of anhydrous THF. The agitation is continued at −70° C. for 1 hour before adding a solution of ethyl acetylisoxazole-3-carboxylate (0.80 g, 4.37 mmol) in 5 ml of anhydrous THF. The reaction medium is brought to ambient temperature and agitated for 3 hours 30 minutes. Then the reaction medium is poured over a mixture of ice-water (150 ml) and 1N HCl (50 ml) and then extracted with ether (2×75 ml)and dichloromethane (2×75 ml). The organic phases are collected together, dried over MgSO$_4$, filtered and evaporated. The raw product is purified by flash chromatography on silica (eluent ether:petroleum ether=2:98 to 10:90). 1.80 g of a colourless oil is obtained, the mixture of (E) and (Z) ethyl 5-[1-(5,6,7,8-tetrahydro-3,5,5,8,8-pentamethyl-2-naphthalenyl)-2-propenyl)]-isoxazole-3-carboxylate (yield=54%) in a ratio determined by NMR$^1$H 200 MHz E:Z=66:33.

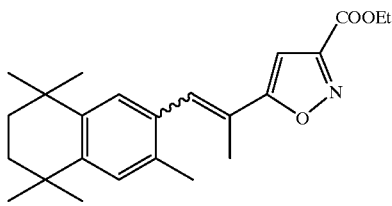

NMR$^1$H 200 MHz (CDCl$_3$) 1.12 (s, 0.33×6H, 2 Me isomer Z); 1.26 (m, 0.66×12H and 0.33×6H, 4 Me isomer E and 2 Me isomer Z); 1.32 (t, 0.33×3H, Me isomer Z J 7.1 Hz); 1.42 (t, 0.66×3H, Me isomer Z J 7.1 Hz); 1.63 (s, 0.33×4H, 6,7-CH$_2$— isomer Z); 1.67 (s, 0.66×4H, 6,7-CH$_2$— isomer E); 2.15 (d, 0.66×3H, vinyl Me isomer E J 1.4 Hz); 2.16 (s, 0.33×3H, aromatic Me isomer Z); 2.25 (s, 0.66×3H, aromatic Me isomer E); 2.29 (d, 0.33×3H, vinyl Me isomer Z J 1.4 Hz); 4.33 (q, 0.33×2H, —OCH$_2$— isomer z J 7.1 Hz); 4.45 (q, 0.66×2H, —OCH$_2$— isomer E J 7.1 Hz); 5.95 (s, 0.33×1H, isoxazole H isomer Z); 6.64 (s, 0.66×1H, isoxazole H isomer E); 6.78 (s, 0.33 1H, vinyl H isomer Z); 7.01 (s, 0.33×1H, ArH isomer Z); 7.10–7.20 (m, 0.33×2H and 0.66×2H, ArH isomer Z and ArH isomer E); 7.42 (s, 0.66×1H, vinyl H isomer E).

b) E) and (Z) 5-[1-(5,6,7,8-tetrahydro-3,5,5,8,8-pentamethyl-2-naphthalenyl)-2-propenyl)]isoxazole-3-carboxylic acids CB54647 and CB82178

A mixture of E) and (Z) ethyl 5-[1-(5,6,7,3-tetrahydro-3,5,5,8,8-pentamethyl-2-naphthalenyl)-2-propenyl)] isoxazole-3-carboxylates (1.80 g, 4.72 mmol) in suspension in 26.0 ml ethanol and 4.5 ml distilled water is put into a 50 ml flask fitted with a condenser and under magnetic stirring. Potassium hydroxide (2.12 g, 38.0 mmol) is added and the reaction mixture brought to reflux for 1 hour 15 minutes. After cooling the reaction medium, it is acidified with 3N HCl to pH=1 and extracted with ether (3×70 ml). The ether phase is dried over MgSO$_4$, filtered and evaporated to obtain 0.92 g of a mixture of (E) and (Z) acids (gross yield=55%). A part of the raw product is purified by preparative HPLC on a Waters HR column C$_{18}$ (25×100 mm) with eluent MeOH:H$_2$O=87:13=0.1% TFA. 0.12 g of a white solid is obtained, (Z) 5-[1-(5,6,7,8-tetrahydro-3,5,5,8,83-pentamethyl-2-naphthalenyl)-2-propenyl)]isoxazole-3-carboxylic acid (CB54647) and 0.23 g of a white solid (E) 5-[1-(5,6,7,8-tetrahydro-3,5,5,8,8-pentamethyl-2-naphthalenyl)-2-propenyl)]isoxazole-3-carboxylic acid (CB82178).

(Z) 5-[1-(5,6,7,8-tetrahydro-3,5,5,8,8-pentamethyl-2-naphthalenyl)-2-propenyl)]isoxazole-3-carboxylic acid (CB54647)

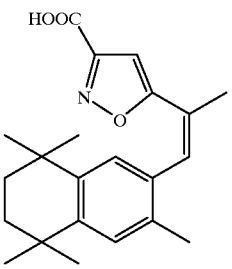

m.pt. (° C.)=162–163
NMR$^1$H 200 MHz (CDCl$_3$): 1.11 and 1.26 (2s, 12H, 5,5,8,8-Me); 1.63 (s, 4H, 6,7-CH$_2$—); 2.17 (s, 3H, aromatic Me); 2.29 (s, 3H, vinyl Me); 5.99 (s, 1H, isoxazole H); 6.80 (s, 1H, vinyl H); 6.99 (s, 1H, ArH); 7.12 (s, 1H, ArH).
MS FAB+NOBA (m/z, % intensity): 354 (MH$^+$, 100%); 338 (35); 154 (34); 136 (29).
HRMS (FAB+NOBA): MH$^+_{tr}$=354.2072 for C$_{22}$H$_{27}$NO$_3$ MH$^+_{th}$=354.2069.
HPLC: Waters HR C$_{18}$ column, 8×100 mm, 6$\mu$, Waters UV detector 486 to 260 nm, flow rate 3 ml/min, eluent MeOH:H$_2$O=87:13=0.1% TFA, acid CB54641 tr=3.28 min 99.1%; impurity isomer (E) (CB82178) tr=4.45 min 0.9%.

(E) 5-[1-(5,6,7,8-tetrahydro-3,5,5,8,8-pentamethyl-2-naphthalenyl)-2-propenyl)]isoxazole-3-carboxylic acid (CB82178)

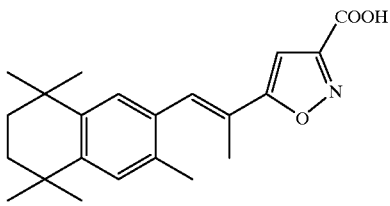

m.pt. (° C.)=204 (dec.)
NMR$^1$H 200 MHz (CDCl$_3$) 1.27 and 1.28 (2s, 12H, 5,5,8,8-Me); 1.68 (s, 4H, 6,7-CH$_2$—); 2.16 (d, 3H, vinyl Me J 1.2 Hz); 2.26 (d, 3H, aromatic Me); 5.63 (s broad, 1H, —COOH); 6.70 (s, 1H, oxazole H); 7.14 (s, 1H, ArH); 7.18 (s, 1H, ArH); 7.45 (d, 1H, vinyl H J 1.2 Hz).
MS FAB+NOBA (m/z, % intensity): 354 (MH$^+$, 100%); 338 (36); 154 (25); 136 (19); 69 (12).
HRMS (FAB+NOBA): MH$^+_{tr}$=354.2069 for C$_{22}$H$_2$7NO$_3$ MH$^+_{th}$=354.2069.
HPLC: Waters HR C$_{18}$ column, 8×100 mm, 6$\mu$, Waters UV detector 486 to 260 nm, flow rate 3 ml/min, eluent MeOH:H$_2$O=85:15+0.1% TFA, acid CB82178 tr=4.53 min 99.6%; impurity isomer (Z) (CB54647) tr=3.28 min 0.2%.

EXAMPLE 25

Preparation of (E) 4-[1-(5,6,7,8-tetrahydro-5,5,8,8-tetramethyl-2-naphthalenyl)-3-ethoxy-2-propenyl] benzoic acid (CB17231)

a) (E) 4-[1-(5,6,7,8-tetrahydro-5,5,8,8-tetramethyl-2-naphthalenyl)-3-bromo-2-propenyl]benzonitrile A solution of (E) 4-[1-(5,6,7,8-tetrahydro-5,5,8,8-tetramethyl-2-naphthalenyl)-2-propenyl]benzonitrile (0.27 g, 0.76 mmol), N-bromosuccinimide (0.16 g, 0.90 mmol), benzoyl peroxide (6 mg) in 3 ml of CCl$_4$ is brought to reflux for 2 hours under an atmosphere of argon and irradiation by a 500-W tungsten lamp. After cooling, the reaction medium is concentrated, taken up in ether and blended onto silica. It is purified by flash chromatography on silica (eluent ether-:petroleum ether=4:96) to obtain, after evaporation, a raw product that is recrystallised with hexane. 0.12 g of a white solid is obtained (E) 4-[1-(5,6,7,8-tetrahydro-5,5,8,8-tetramethyl-2-naphthalenyl)-3-bromo-2-propenyl]benzonitrile (yield=36.5%).

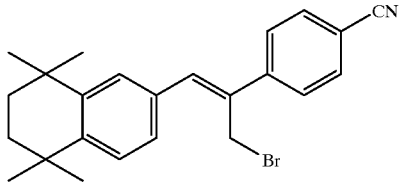

m.pt. (° C.)=151

NMR[1]H 200 MHz (CDCl$_3$): 1.29 and 1.32 (s, 12H, 5,5,8,8-CH$_3$); 1.70 (s, 4H, 6,7-CH$_2$—); 4.54 (s, 2H, BnzH); 7.02 (s, 1H, vinyl H); 7.25 (dd, 1H, ArH J 2 Hz J 8 Hz); 7.37 (d, 1H, ArH J 8 Hz); 7.54 (d, 1H, ArH J 2Hz); 7.67 (s, 4H, ArH).

b) (E) 4-[1-(5,6,7,8-tetrahydro-5,5,8,8-tetramethyl-2-naphthalenyl)-3-ethoxy-2-propenyl]benzoic acid (CB17231)

Potassium hydroxide (0.50 g, 8.42 mmol) is added to a suspension of (E) 4-[1-(5,6,7,8-tetrahydro-5,5,8,8-tetramethyl-2-naphthalenyl)-3-bromo-2-propenyl]benzonitrile in ethanol and water (H$_2$O 0.55 ml and EtOH 3.3 ml). It is heated to reflux under magnetic stirring for 20 hours. After cooling, it is acidified with 10 ml of 1N HCl solution, extracted with ether (3×50 ml), dried over MgSO$_4$, filtered and evaporated. The raw product is purified by preparative HPLC on a Waters HR column C$_{18}$ (25×100 mm) with eluent MeOH:H$_2$O=85:15=0.1% TFA. 0.03 g of a white solid is obtained (E) 4-[1-(5,6,7,8-tetrahydro-5,5,8,8-tetramethyl-2-naphthalenyl)-3-ethoxy-2-propenyl]benzoic acid (CB172.31) (yield=27%).

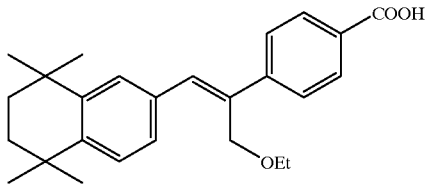

m.pt. (° C.)=135

NMR[1]H 200 MHz (CDCl$_3$): 1.27 (t, 3H, Me J 7 Hz); 1.29 and 1.31 (s, 12H, 5,5,8,8-CH$_3$); 1.70 (s, 4H, 6,7-CH$_2$—); 3.59 (q, 2H, —OCH$_2$— J 7 Hz); 7.15 (s, 1H, vinyl H); 7.15–7.45 (m, 3H, ArH); 7.89 (dm, 2H, ArH meta to the —COOH J 8 Hz); 8.09 (dm, 2H, ArH ortho to the —COOH J 8 Hz).

MS EI 70 ev (m/z, % intensity): (M$^+$, 95%); 377 (66); 323 (14); 281 (37); 215 (22), 149 (100); 91 (21); 71 (16); 69 (44); 57 (47); 55 (46).

HRMS EI 70 ev: M$_{tr}$=398.2359 for C$_{26}$H$_{32}$O$_3$ M$_{th}$=392.2351.

HPLC: Waters HR C$_{18}$ column, 8×100 mm, 6$\mu$, Waters UV detector 486 to 260 nm, flow rate 3 ml/min, eluent MeOH:H$_2$O=85:15=0.1% TFA, acid (CB17231) tr=7.12 min 98.3%; impurity tr=4.73 min 1.40%.

EXAMPLE 26

Preparation of (E) N-Carbethoxy-4-[1-(5,6,7,8-tetrahydro-5,5,8,8-tetramethyl-2-naphthalenyl)-2-propenyl]aniline (CB21282)

Diphenylphosphoryl azide (0.37 ml, 1.70 mmol) and triethylamine (0.24 ml, 1.69 mmol) are added successively with a syringe to a suspension of (E) 4-[1-(5,6,7,8-tetrahydro-5,5,8,8-tetramethyl-2-naphthalenyl)-2-propenyl] benzoic acid (CB24159) (0.56 g, 1.61 mmol) in 5 ml of toluene. The mixture is brought to 80° C. under an atmosphere of argon and with magnetic stirring for 1 hour. After cooling, 0.95 ml of ethanol is added and it is then brought to 80° C. for 3 hours. After cooling the mixture is evaporated to dryness, taken up in ether and blended onto silica. The raw mixture is purified by flash chromatography on silica (eluent ether:petroleum ether=3:97 to 5:95). After evaporation, 0.50 g of a white solid is obtained, (E) N-Carbethoxy-4-[1-(5,6,7,8-tetrahydro-5,5,8,8-tetramethyl-2-naphthalenyl)-2-propenyl]aniline (CB21282) (yield=79.5%).

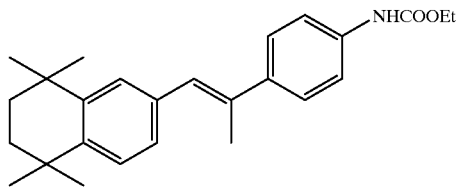

m.pt. (° C.)=124–5

NMR[1]H 200 MHz (CDCl$_3$): 1.31 and 1.32 (2s, 12H, 5,5,8,8-CH$_3$); 1.30 (t, 3H, Me J 7.1 Hz); 1.71 (s, 4H, 6,7-CH$_2$—); 2.28 (d, 3H, vinyl Me J 1.2 Hz); 4.24 (q, 2H, —OCH$_2$— J 7.1 Hz); 6.76 (s broad, 1H, —NH—); 6.79 (s, 1H, vinyl H); 7.15 (dd, 1H, ArH J 1.8 Hz J 8.5 Hz); 7.25–7.35 (m, 2H, ArH); 7.38 (d, 2H meta to the —NH— J 8.7 Hz); 7.48 (d, 2H ortho to the —NH— J 8.7 Hz).

MS EI 70 ev (m/z, % intensity): 391 (M$^+$, 100%) 376 (69); 330 (17); 69 (25); 57 (17).

HRMS EI 70 ev: M$_{tr}$=391.2502 for C$_{26}$H$_{33}$NO$_2$ M$_{th}$=391.2512.

HPLC: Waters HR C$_{18}$ column, 8×100 mm, 6$\mu$, Waters UV detector 486 to 260 nm, flow rate 3 ml/min, eluent MeOH:H$_2$O=90:10=0.1% TFA, N-carbethoxyaniline (CB21282) tr=4.04 min purity 97.6%; impurity tr=3.20 min 2.1%.

EXAMPLE 27

Preparation of (Z) N-Carbethoxy-4-[1-(5,6,7,8-tetrahydro-5,5,8,8-tetramethyl-2-naphthalenyl)-2-propenyl]aniline (CB96682)

Diphenylphosphoryl azide (0.29 ml, 1.34 mmol) and triethylamine (0.19 ml, 1.33 mmol) are added successively with a syringe to a suspension of (Z) 4-[1-(5,6,7,8-tetrahydro-5,5,8,8-tetramethyl-2-naphthalenyl)-2-propenyl] benzoic acid (CB28628) (0.44 g, 1.26 mmol) in 4 ml of toluene. The mixture is brought to 80° C. under an atmosphere of argon and with magnetic stirring for 1 hour. After cooling, 1.0 ml of ethanol is added and it is then brought to 80° C. for 3 hours. After cooling the mixture is evaporated to dryness, taken up in ether and blended onto silica. The raw mixture is purified by flash chromatography on silica (eluent ether:petroleum ether=3:97 to 5:95). After evaporation, 0.40 g of a colourless oil is obtained, (Z)N-Carbethoxy-4-[1-(5, 6,7,8-tetrahydro-5,5,8,8-tetramethyl-2-naphthalenyl)-2-propenyl]aniline (CB96682) (yield 81%).

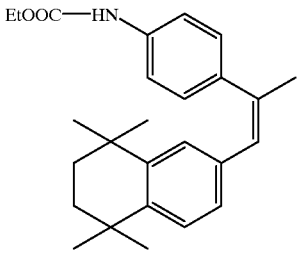

m.pt. (° C.)=47.

NMR¹H 200 MHz (CDCl₃): 1.00 and 1.19 (2s, 12H, 5,5,8,8-CH₃); 1.30 (t, 3H, Me J 7.1 Hz); 1.57 (s, 4H, 6,7-CH₂—); 2.14 (d, 3H, vinyl Me J 1.3 Hz); 4.21 (q, 2H, —OCH₂— J 7.0Hz); 6.37 (d, 1H vinyl H J 1.3 Hz); 6.56 (s broad, 1H, —NH—); 6.74 (dd, 1H, ArH J 1.9 Hz J 8.2 Hz); 6.86 (d, 1H, ArH J 1.9 Hz); 7.04 (d, 1H, ArH J 8.2 Hz); 7.14 (dm, 2H, ArH meta to the —NH— J 8.6 Hz); 7.48 (dm, 2H ortho to the —NH— J 8.6 Hz).

MS EI 70 ev (m/z, % intensity): 391 (M⁺, 100%); 376 (49); 330 (14); 215 (31); 57 (14).

HRMS EI 70 ev: $M_{tr}$=391.2512 for $C_{26}H_{33}NO_2$ $M_{th}$= 391.2512.

HPLC: Waters HR $C_{18}$ column, 8×100 mm, 6μ, Waters UV detector 486 to 260 nm, flow rate 3 ml/min, eluent MeOH:H₂O=90:10=0.1% TFA, N-carbethoxyaniline (CB96682) tr=3.17 min purity 98.8%; impurity tr=1.45 min 0.6%.

EXAMPLE 28

Preparation of (E) 1-[4-[1-(5,6,7,8-tetrahydro-5,5,8,8-tetramethyl-2-naphthalenyl)-2-propenyl]phenyl]-5-trifluoromethyl-1H-tetrazole (CB59741)

a) (E) 4-[1-(5,6,7,8-tetrahydro-5,5,8,8-tetramethyl-2-naphthalenyl)-2-propenyl]aniline A suspension of (E)N-Carbethoxy-4-[1-(5,6,7,8-tetrahydro-5,5,8,8-tetramethyl-2-naphthalenyl)-2-propenyl]aniline (CB21282) (0.50 g, 1.28 mmol) in 10N sodium hydroxide (3.84 ml, 38.4 mmol) and 1.5 ml of ethanol is brought to 80° C. for 3 hours under an atmosphere of argon and with magnetic stirring. After cooling, the mixture is extracted with dichloromethane (4×25 ml), dried over MgSO₄, filtered and evaporated to obtain 0.31 g of a raw yellowish oil (E) 4-[1-(5,6,7,8-tetrahydro-5,5,8,8-tetramethyl-2-naphthalenyl)-2-propenyl]aniline (yield= 76%).

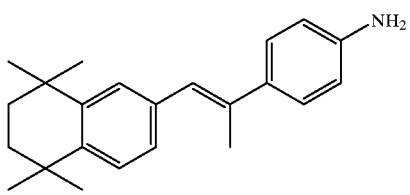

NMR¹H 200 MHz (CDCl₃): 1.37 and 1.38 (2s, 12H, 5,5,8,8-CH₃); 1.77 (s, 4H, 6,7-CH₂—); 2.33 (d, 3H, vinyl Me J 1.2 Hz); 3.70 (s broad, 2H, —NH₂—); 6.72 (dm, 2H, ArH J 8.6 Hz); 6.81 (d, 1H, vinyl H J 1.3 Hz); 7.21 (dd, 1H, ArH J 1.7 Hz J 8.2 Hz); 7.30–7.50 (m, 4H, ArH).

b) (E) N-(trifluoroacetyl)-4-[1-(5,6,7,8-tetrahydro-5,5,8,8-tetramethyl-2-naphthale(nyl)-2-propenyl]aniline A solution of (E) 4-[1-(5,6,7,8-tetrahydro-5,5,8,8-tetramethyl-2-naphthalenyl)-2-propenyl]aniline (0.31 g, 0.97 mmol) and 2-(trifluoroacetoxy)pyridine (0.15 ml, 1.07 mmol) in 3 ml of anhydrous ether is mixed for 30 minutes at ambient temperature under an atmosphere of argon. The ether phase is ihen washed with distilled water, dried over MgSO₄, filtered and evaporated. 0.40 g of a yellowish solid is obtained (E) N-(trifluoroacetyl)-4-[1-(5,6,7,8-tetrahydro-5,5,8,8-tetramethyl-2-naphthalenyl)-2-propenyl]aniline (gross yield=99%).

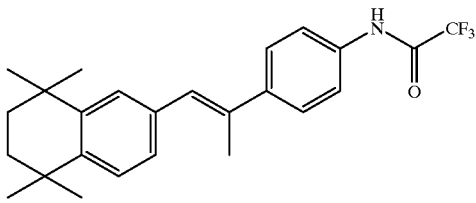

m.pt. (° C.)=124.

NMR¹H 200 MHz (CDCl₃): 1.28 and 1.29 (2s, 12H, 5,5,8,8-CH₃); 1.69 (s, 4H, 6,7-CH₂—); 2.27 (d, 3H, vinyl Me J 1.0 Hz); 6.80 (s, 1H, vinyl H); 7.13 (dd, 1H, ArH J 1.8 Hz J 8.0 Hz); 7.27 (s, 1H, ArH); 7.30 (d, 1H, ArH J 8.0 Hz); 7.54 (s, 4H, ArH); 7.88 (s broad, 1H, —NH—).

NMR¹⁹F 50 MHz (CDCl₃) −76.23 (s, 0.77×3F, CF₃ amide trans); −76.62 (s, 0.23×3F, CF₃ amide cis).

c) (E) N-[4-[1-(5,6,7,8-tetrahydro-5,5,8,8-tetramethyl-2-naphthalenyl)-2-propenyl]phenyl]-2,2,2-trifluoroacetimidoyl chloride A solution of (E) N-(trifluoroacetyl)-4-[1-(5,6,7,8-tetrahydro-5,5,8,8-tetrametlhyl-2-naphthalenyl)-2-propenyl]aniline (0.40 g, 0.96 mmol), triphenylphosphine (0.60 g, 2.30 mmol) in 3.5 ml of anhydrous carbon tetrachloride is brought to reflux for 6 hours under an atmosphere of argon and with magnetic stirring. After cooling, the solvent is evaporated, the product taken up in dichloromethane and blended onto silica. The raw product is purified by flash chromatography on silica (eluent ether:petroleum ether=4:96). After evaporation, 0.32 g of a white solid is obtained (E) N-[4-[1-(5,6,7,8-tetrahydro-5,5,8,8-tetramethyl-2-naphthalenyl)-2-propenyl]phenyl]-2,2,2-trifluoroacetimidoyl chloride (yield=77%).

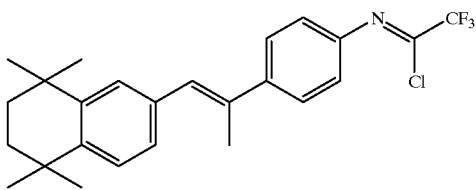

m.pt. (° C.)=60.

NMR¹H 200 MHz (CDCl₃): 1.30 and 1.31 (2s, 12H, 5,5,8,8-CH₃); 1.50 (s, 4H, 6,7-CH₂—); 2.31 (s, 3H, vinyl Me); 6.87 (s, 1H, vinyl H); 7.10–7.20 (m, 3H, ArH); 7.25–7.35 (m, 2H, ArH); 7.59 (d, 2H, ArH J 8.5 Hz).

NMR¹⁹F 50 MHz (CDCl₃): −71.94 (s, 3F, CF₃).

d) (E) 1-[4-[1-(5,6,7,8-tetrahydro-5,5,8,8-tetramethyl-2-naphthalenyl)-2-propenyl]phenyl]-5-trifluoro-methyl-1H-tetrazole (CB59741)

A solution of (E) N-[4-[1-(5,6,7,8-tetrahydro-5,5,8,8-tetramethyl-2-naphthalenyl)-2-propenyl]phenyl]-2,2,2-trifluoroacetimidoyl chloride (0.32 g, 0.74 mmol), sodium azide (0.10 g, 1.48 mmol) in 1.5 ml of glacial acetic acid is brought to 70° C. for 2 hours, under an atmosphere of argon and with magnetic stirring. After cooling of the reaction medium, the solvent is evaporated, the product taken up in dichloromethane and blended onto silica. It is purified by flash chromatography on silica (eluent ether:petroleum ether=7:93). After evaporation of the solvents, 0.30 g of a colourless oil is obtained (E) 1-[4-[1-(5,6,7,8-tetrahydro-5,5,8,8-tetramethyl-2-naphthalenyl)-2 -propenyl]phenyl]-5-trifluoro-methyl-1H-tetrazole (CB59741) (yield=92%).

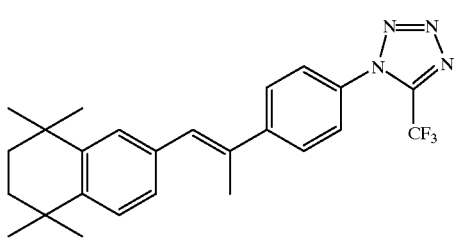

NMR$^1$H 200 MHz (CDCl$_3$): 1.30 and 1.31 (2s, 12H, 5,5,8,8-CH$_3$); 1.70 (s, 4H, 6,7-CH$_2$—); 2.34 (s, 3H, vinyl Me); 6.91 (s, 1H, vinyl H); 7.16 (dd, 1H, ArH J 1.9 Hz J 8.1 Hz); 7.27–7.37 (m, 2H, ArH); 7.47 (d, 2H, ArH J 8.6 Hz); 7.72 (d, 2H, ArH J 8.6 Hz).

NMR$^{19}$F 50 MHz (CDCl$_3$): –60.39 (s, 3F, CF$_3$).

MS EI 70 ev (m/z, % intensity): 440 (M$^+$, 100%); 397 (100); 343 (15); 248 (36); 215 (46); 111 (24); 69 (57).

HRMS EI 70 ev: M$_{tr}$=440.2180 for C$_{25}$H$_{27}$N$_4$F$_3$ M$_{th}$=440.2188.

HPLC: Waters HR C$_{18}$ column, 8×100 mm, 6μ, Waters UV detector 486 to 260 nm, flow rate 3 ml/min, eluent MeOH:H$_2$O=90:10=0.1% TFA, tetrazole (CB59741) tr=3.88 min purity 96.6%; impurity tr=3.24 min 2.7%.

EXAMPLE 29

Preparation of (Z) 1-[4-[1-(5,6,7,8-tetrahydro-5,5,8,8-tetramethyl-2-naphthalenyl)-2-propenyl]-phenyl]-5-trifluoromethyl-1H-tetrazole (CB29830)

a) (Z) 4-[1-(5,6,7,8-tetrahydro-5,5,8,8-tetramethyl-2-naphthalenyl)-2-propenyl]aniline A suspension of (Z) N-Carbethoxy-4-[1-(5,6,7,8-tetrahydro-5,5,8,8-tetramethyl-2-naphthalenyl)-2-propenyl]aniline (CB96682) (0.28 g, 1.28 mmol) in 10N sodium hydroxide (3.84 ml, 38.4 mmol) and 1.5 ml of ethanol is brought to 80° C. for 3 hours under an atmosphere of argon and with magnetic stirring. After cooling, the mixture is extracted with dichloromethane (4×25 ml), dried over MgSO$_4$, filtered and evaporated to obtain 0.22 g of a raw orange coloured oil (Z) 4-[1-(5,6,7,8-tetrahydro-5,5,8,8-tetramethyl-2-naphthalenyl)-2-propenyl]aniline (yield=96.5%).

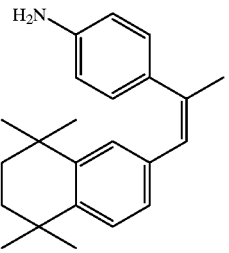

NMR$^1$H 200 MHz (CDCl$_3$): 1.04 and 1.20 (2s, 12H, 5,5,8,8-CH$_3$); 1.59 (s, 4H, 6,7-CH$_2$—); 2.14 (d, 3H, vinyl Me J 1.4 Hz); 3.62 (s broad, 2H, —NH$_2$—); 6.32 (s, 1H, vinyl H); 6.72 (dm, 2H, ArH J 8.4 Hz); 6.78 (dd, 1H, ArH J 1.8 Hz J 8.2 Hz); 6.93 (d, 1H, ArH J 1.8 Hz); 7.01 (dm, 2H, ArH J 8.4 Hz); 7.05 (d, 1H, ArH J 8.2 Hz).

b) (Z) N-(trifluoroacetyl)-4-[1-(5,6,7,8-tetrahydro-5,5,8,8-tetramethyl-2-naphthalenyl)-2-propenyl]aniline A solution of (Z) 4-[1-(5,6,7,8-tetrahydro-5,5,8,8-tetramethyl-2-naphthalenyl)-2-propenyl]aniline (0.22 g, 0.69 mmol) and 2-(trifluoroacetoxy)pyridine (0.11 ml, 0.76 mmol) in 2.5 ml of anhydrous ether is mixed for 30 minutes at ambient temperature under an atmosphere of argon. The ether phase is then washed with distilled water, dried over MgSO$_4$, filtered and evaporated. The product is taken up in ether and blended onto silica in order to purify it by flash chromatography on silica (eluent ether:petroleum ether 7:93). After evaporation of the solvents, 0.20 g of a colourless oil is obtained (Z) N-(trifluoroacetyl)-4-[1-(5,6,7,8-tetrahydro-5,5,8,8-tetramethyl-2-naphthalenyl)-2-propenyl] aniline (yield=70%).

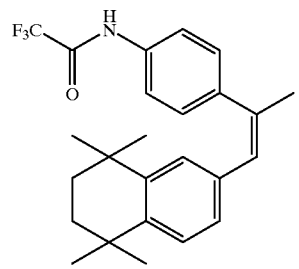

NMR$^1$H 200 MHz (CDCl$_3$) 1.00 and 1.20 (2s, 12H, 5,5,8,8-CH$_3$); 1.58 (s, 4H, 6,7-CH$_2$—); 2.16 (d, 3H, vinyl Me J 1.4 Hz); 6.43 (s, 1H, vinyl H); 6.73 (dd, 1H, ArH J 1.8 Hz J 8.2 Hz); 6.85 (d, 1H, ArH J 1.8 Hz); 7.05 (d, 1H, ArH J 8.2 Hz); 7.23 (dm, 2H, ArH J 8.6 Hz); 7.49 (dm, 2H, ArH J 8.6 Hz); 7.92 (s broad, 1H, —NH—).

NMR$^{19}$F 50 MHz (CDCl$_3$): –76.15 (s, 3F, CF$_3$).

c) (Z) N-[4-[1-(5,6,7,8-tetrahydro-5,5,8,8-tetramethyl-2-naphthalenyl)-2-propenyl]phenyl]-2,2,2-trifluoroacetimidoyl chloride A solution of (Z) N-(trifluoroacetyl)-4-[1-(5,6,7,8-tetrahydro-5,5,8,8-tetramethyl-2-naphthalenyl)-2-propenyl] aniline (0.20 g, 0.48 mmol), triphenylphosphine (0.30 g, 1.15 mmol) in 3 ml of anhydrous carbon tetrachloride is brought to reflux for 18 hours under an atmosphere of argon and with magnetic stirring. After cooling, the solvent is evaporated, the product taken up in dichloromethane and blended onto silica. The raw product is purified by flash chromatography on silica (eluent pure petroleum ether). After evaporation, 0.16 g of a white solid is obtained (Z)

N-[4-[1-(5,6,7,8-tetrahydro-5,5,8,8-tetramethyl-2-naphthalenyl)-2-propenyl]phenyl]-2,2,2-trifluoroacetimidoyl chloride (yield=77%).

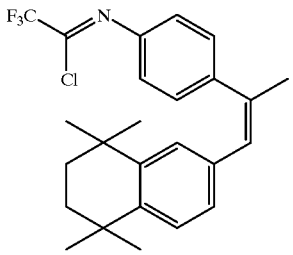

m.pt. (° C.)=76.

NMR¹H 200 MHz (CDCl₃): 0.96 and 1.18 (2s, 12H, 5,5,8,8-CH₃); 1.55 (s, 4H, 6,7-CH₂—); 2.17 (s, 3H, vinyl Me J 1.4 Hz); 6.43 (s, 1H, vinyl H); 6.76 (dd, 1H, ArH J 1.9 Hz J 8.1 Hz); 6.84 d, 1H ArH J 1.9 Hz); 7.00–7.15 (m, 3H, ArH); 7.27 (dm, 2H, ArH J 8.6 Hz).

NMR¹⁹F 50 MHz (CDCl₃): –72.01 (s, 3F, CF₃).

d) (Z) 1-[4-[1-(5,6,7,8-tetrahydro-5,5,8,8-tetramethyl-2-naphthalenyl)-2-propenyl]phenyl]-5-trifluoro-methyl-1H-tetrazole (CB29830)

A solution of (Z) N-[4-[1-(5,6,7,8-tetrahydro-5,5,8,8-tetramethyl-2-naphthalenyl)-2-propenyl]phenyl]-2,2,2-trifluoroacetimidoyl chloride (0.16 g, 0.37 mmol), sodium azide (0.05 g, 1.74 mmol) in 0.75 ml of glacial acetic acid is brought to 70° C. for 20 hours, under an atmosphere of argon and with magnetic stirring. After cooling of the reaction medium, the solvent is evaporated, the product taken up in dichloromethane and blended onto silica. It is purified by flash chromatography on silica (eluent ether:petroleum ether=4:96). After evaporation of the solvents, 0.07 g of a white solid is obtained (Z) 1-[4-[1-(5,6,7,8-tetrahydro-5,5,8,8-tetramethyl-2-naphthalenyl)-2-propenyl]phenyl]-5-trifluoro-methyl-1H-tetrazole (CB29830) (yield=43%).

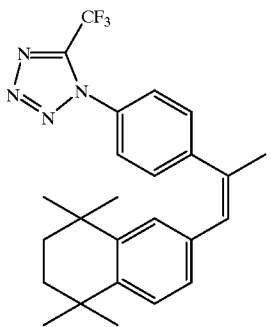

m.pt. (° C.)=111

NMR¹H 200 MHz (CDCl₃) 0.97 and 1.20 (2s, 12H, 5,5,8,8-CH₃); 1.57 (s, 4H, 6,7-CH₂—); 2.22 (d, 3H, vinyl Me J 1.4 Hz); 6.54 (s, 1H, vinyl H); 6.76 (dd, 1H, ArH J 1.7 Hz J 8.1 Hz); 6.83 (d, 1H, ArH J 1.7 Hz); 7.10 (d, 1H, ArH J 8.1 Hz); 7.42 (m, 4H, ArH).

NMR¹⁹F 50 MHz (CDCl₃): –60.32 (s, 3F, CF₃).

MS EI 70 ev (m/z, % intensity): 440 (M⁺, 100%); 397 (63); 248 (9); 69 (33).

HRMS EI 70 ev: $M_{tr}$=440.2173 for $C_{25}H_{27}N_4F_3$ $M_{th}$=440.2188.

HPLC: Waters HR $C_{18}$ column, 8×100 mm, 6µ, Waters UV detector 486 to 260 nm, flow rate 3 ml/min, eluent MeOH:H₂O=90:10=0.1% TFA, tetrazole (CB29830) tr=3.37 min purity 98.7%; impurity tr=4.05 min 0.8%.

EXAMPLE 30

Preparation of (Z) 2-[1-(5,6,7,8-tetrahydro-5,5,8,8-tetramethyl-2-naphthalenyl)-2-propenyl]thienyl-5-phosphonic acid (CB46802)

a) (E) and (Z) diethyl 2-[1-(5,6,7,8-tetrahydro-5,5,8,8-tetramethyl-2-naphthalenyl)-2-propenyl]thienyl-5-phosphonates A suspension of (Z) 2-[1-(5,6,7,8-tetrahydro-5,5,8,8-tetramethyl-2-naphthalenyl)-2-propenyl]-5-bromothiophene (2.52 g, 6.47 mmol), diethyl phosphite (1.67 ml, 12.94 mmol), triethylamine (1.80 ml, 12.94 mmol) and tetrakis (triphenylphosphine)palladium (0.87 g, 0.75 mmol) in 3 ml of anhydrous THF is brought to reflux for 15 hours, under an atmosphere of argon and with magnetic stirring. After cooling the reaction medium, it is taken up with ethyl acetate (100 ml) and washed with a solution of 1N HCl and then by a saturated solution of NaCl. After evaporation of the solvent, the raw product is purified by flash chromatography on silica (eluent ether:petroleum ether=50:50 then 70:30). After evaporation, 0.83 g of a yellowish oil is obtained (yield=29% made up of a mixture of (E) and (Z) diethyl 2-[1-(5,6,7,8-tetrahydro-5,5,8,8-tetramethyl-2-naphthalenyl)-2-propenyl]thienyl-5-phosphonates (ratio (E):(Z)=75:25 by NMR¹H 80 MHz).

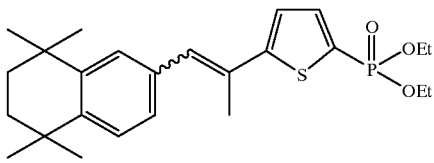

NMR¹H 80 MHz (CDCl₃): 1.05–1.50 (m, 18H, 6Me); 1.55–1.70 (m, 4H, 6,7-CH₂); 2.20 (s, 0.25×3H, vinyl Me isomer Z); 2.30 (s, 0.75×3H, vinyl Me isomer E); 3.90–4.35 (m, 4H, —OCH₂—); 6.50–7.65 (m, 6H, ArH and vinyl H).

b) (E) 2-[1-(5,6,7,8-tetrahydro-5,5,8,8-tetramethyl-2-naphthalenyl)-2-propenyl]thienyl-5-phosphonic aced (CB46802)

Bromotrimethylsilane (1.58 ml, 11.97 mmol) is added with a syringe to a suspension of the mixture of (E) and (Z) diethyl 2-[1-(5,6,7,8-tetrahydro-5,5,8,8-tetramethyl-2-naphthalenyl)-2-propenyl]thienyl-5-phosphonates (0.83 g, 1.86 mmol) in 12 ml of acetonitrile. The reaction mixture is brought to reflux for 2 hours, under an atmosphere of argon and with magnetic stirring. After cooling, it is evaporated to dryness and taken up in ethanol. It is once again evaporated and a white solid is precipitated by a minimum of ethyl ether. This is filtered and dried to obtain 0.11 g of a white solid (E) 2-[1-(5,6,7,8-tetrahydro-5,5,8,8-tetramethyl-2-naphthalenyl)-2-propenyl]thienyl-5-phosphonic acid (CB46802) (yield=15%).

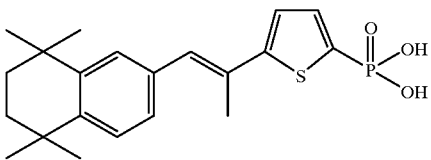

m.pt. (° C.)=175–176

NMR[1]H 200 MHz (CDCl$_3$): 1.26 and 1.27 (2s, 12H, 5,5,8,8-Me); 1.69 (s, 4H, 6,7-CH$_2$); 2.26 (d, 3H, vinyl Me J 0.9 Hz); 7.02 (s, 1H, vinyl H); 7.09 (dd, 1H, ArH J 1.7 Hz J 8.6 Hz); 7.15–7.35 (m, 4H, ArH); 7.45 (dd, 1H, ArH J=3.7 Hz J=8.6 Hz).

MS EI 70 ev (m/z, % intensity): 390 (M$^+$, 0.1%); 375 (0.4%); 310 (87); 295 (100); 262 (35); 183 (27).

HPLC: Waters HR C$_{18}$ column, 8×100 mm, 6µ, Waters UV detector 486 to 260 nm, flow rate 3 ml/min, eluent MeOH:H$_2$O=85:15=0.1% TFA, acid (CB46802) tr=2.93 min 98.8%; impurity tr=1.36 min 0.7%.

EXAMPLE 31

Preparation of (Z) 4-[1-(5,6,7,8-tetrahydro-5,5,8,8-tetramethyl-2-naphthalenyl)-1-(phenyl)-2-ethenyl] benzoic acid (CB59892)

1) (Z) 4-[1-(5,6,7,8-tetrahydro-5,5,8,8-tetramethyl-2-naphthalenyl)-1-(phenyl)-2-ethenyl]benzonitrile Copper cyanide (0.52 g, 5.81 mmol) is added at ambient temperature to a solution of the (Z) compound 4-[1-(5,6,7,8-tetrahydro-5,5,8,8-tetramethyl-2-naphthalenyl)-1-(phenyl)-2-ethenyl]bromobenzene (2.21 g, 4.96 mmol) in 18.5 ml of anhydrous DMF. The reaction medium is refluxed for 15 hours. After returning to ambient temperature, the reaction medium is diluted with ether (200 ml) and filtered on celite. The organic phase is washed with a saturated solution of NaHCO$_3$ (3×50 ml), dried over MgSO$_4$, filtered and evaporated. The raw product is purified by flash chromatography on silica (eluent petroleum ether:ether=100:2). 1.29 g of a yellowish oil is obtained, the (Z) compound 4-[L1-(5,6,7,8-tetrahydro-5,5,8,$^8$-tetramethyl-2-naphthalenyl)-1-(phenyl)-2-ethenyl]benzonitrile (yield=66%).

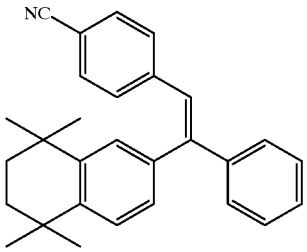

NMR[1]H 200 MHz (CDCl$_3$): 1.05 and 1.35 (2s, 12H, 5,5,8,8 Me); 1.65 (s, 4H, 6,7-CH$_2$—); 6.80–6.90 (m, 2H, vinyl H and ArH); 7.00–7.10 (m, 3H, ArH); 7.20–7.50 (m, 8H, ArH).

2 (Z) 4-[1-(5,6,7,8-tetrahydro-5,5,8,8-tetramethyl-2-naphthalenyl)-1-(phenyl)-2-ethenyl]benzoic acid (CB59892)

A suspension of compound (Z) 4-[1-(5,6,7,8-tetrahydro-5,5,8,8-tetramethyl-2-naphthalenyl)-1-(phenyl)-2-ethenyl] benzonitrile (0.50 g, 1.27 mmol) in solution in alcoholic potassium hydroxide (1.4 g, 25 mmol KOH in 1.8 ml H$_2$O and 17.5 ml EtOH) is heated to reflux under magnetic stirring for 48 hours. The ethanol is evaporated in a rotary evaporator, the product taken up in water (10 ml), acidified with 3N HCl and extracted with ether (3×50 ml). The ether phase is dried with MgSO$_4$, filtered and evaporated. The product is washed with pentane, filtered and dried. 521 mg of a white solid is obtained, (Z) 4-[1-(5,6,7,8-tetrahydro-5,5,8,8-tetramethyl-2-naphthalenyl)-1-(phenyl)-2-ethenyl] benzoic acid (CB59892) (yield=63%).

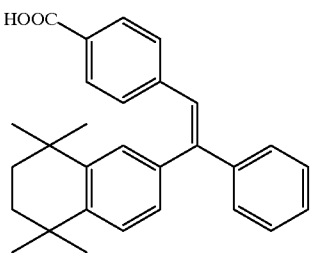

m.pt. (° C.)=222

IR (cm$^{-1}$): 2954; 1676; 1604; 1416; 1284.

NMR[1]H 200 MHz (CDCl$_3$) 1.03 and 1.20 (2s, 12H, 5,5,8,8-Me); 1.65 (s, 4H, 6,7-CH$_2$—); 6.85 (dd, 1H, J 2 Hz and J 8 Hz); 6.92 (s, 1H, vinyl H); 7.04–7.08 (m, 3H, ArH); 7.21–7.39 (m, 6H, ArH); 7.82 (d, 2H, J 8 Hz).

MS EI 70 eV (m/z, % intensity): 410 (M$^+$, 100%); 395 (48).

HRMS EI 70 eV: M$_{tr}$=410.2246 for C$_{29}$H$_{30}$O$_2$ M$_{th}$=410.2246.

HPLC: Waters HR C$_{18}$ column, 8×100 mm, 6µ, Waters UV detector 486 to 260 nm, flow rate 3 ml/min, eluent MeOH:H$_2$O=90:10=0.1% TFA, acid (CB59892) tr=5.34 min 99.8%.

EXAMPLE 32

Preparation of (Z) 5-[4-[1-(5,6,7,8-tetrahydro-5,5,8,8-tetramethyl-2-naphthalenyl)-1-(phenyl)-2-ethenyl] phenyl]-1H-tetrazole (CB96561)

Dibutyl tin oxide (22.8 mg, 0.09 mmol) and trimethylsilyl azide (0.235 ml, 1.78 mmol), are added successively to a solution of (Z) 4-[1-(5,6,7,8-tetrahydro-5,5,8,8-tetramethyl-2-naphthalenyl)-1-(phenyl)-2-ethenyl]-benzonitrile (0.35 g, 0.89 mmol) in anhydrous toluene (1.8 ml). The reaction medium is heated for 18 hours at reflux (110° C.) under an atmosphere of argon and with magnetic stirring. The mixture is purified by flash chromatography on silica (eluent MeOH:CH$_2$Cl$_2$=5:95) to obtain, after evaporation, 260 mg of a white powder (Z) 5-[4-[1-(5,6,7,8-tetrahydro-5,5,8,8-tetramethyl-2-naphthalenyl)-1-(phenyl)-2-ethenyl]phenyl]-1H-tetrazole (CB96561) (yield 67%).

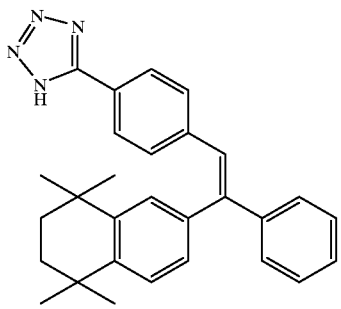

m. pt. (° C.)=232

IR (cm$^{-1}$): 2958; 1604; 1496; 1446; 1060; 880.

NMR$^1$H 200 MHz (CDCl$_3$): 1.03 and 1.26 (2s, 12H, 5,5,8-CH$_3$); 1.63 (s, 4H, 6,7-CH$_2$); 6.88–6.90 (m, 2H); 7.08–7.35 (m, 9H, ArH); 7.79 (d, 2H, ArH, J 8 Hz).

MS EI 70 eV (m/z, % intensity): 434 (M$^+$, 62%); 406 (100); 204 (65); 178 (13).

HRMS EI 70 eV: M$_{tr}$=434.2484 for C$_{29}$H$_{30}$N$_4$ M$_{th}$=434.2470.

HPLC: Waters HR C$_{18}$ column, 8×100 mm, 6μ, Waters UV detector 486 to 260 nm, flow rate 3 ml/min, eluent MeOH:H$_2$O=90:10=0.1% TFA, tetrazole (CB96561) tr=3.69 min 99.7%.

EXAMPLE 33

Preparation of (E) 5-[4-[1-(5,6,7,8-tetrahydro-5,5,8,8-tetramethyl-2-naphthalenyl)-1-(phenyl)-2-ethenyl]phenyl]-1H-tetrazole (CB56898)

Dibutyl tin oxide (23.3 mg, 0.089 mmol) and trimethylsilyl azide (0.200 ml, 1.48 mmol), are added successively to a solution of (E) 4-[1-(5,6,7,8-tetrahydro-5,5,8,8-tetramethyl-2-naphthalenyl)-1-(phenyl)-2-ethenyl]-benzonitrile (0.29 g, 0.74 mmol) in anhydrous toluene (1.5 ml). The reaction medium is heated for 15 hours at reflux (110° C.) under an atmosphere of argon and with magnetic stirring. The mixture is purified by flash chromatography on silica (eluent MeOH:CH$_2$Cl$_2$=5:95) to obtain, after evaporation, 40 mg of a white powder (E) 5-[4-[1-(5,6,7,8-tetrahydro-5,5,8,8-tetramethyl-2-naphthalenyl)-1-(phenyl)-2-ethenyl]phenyl]-1H-tetrazole (CB56898) (yield 12%).

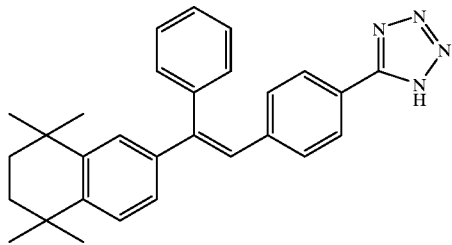

m. pt. (° C.)=254

IR (cm$^{-1}$): 2958; 1666; 1610; 1496; 1456; 1404; 1362; 1272; 1056; 878.

NMR$^1$H 200 MHz (CDCl$_3$) 1.22 and 1.26 (2s, 12H, 5,5,8,8-CH$_3$); 1.67 (s, 4H, 6,7-CH$_2$); 6.95 (s, 1H, vinyl H); 7.14 (dd, 1H, ArH J 2 Hz and J 8 Hz); 7.21 (m, 9H, ArH) 7.78 (d, 2H, ArH, J 8 Hz).

MS EI 70 eV (m/z, % intensity): 434 (M$^+$, 66%); 406 (100); 219 (39); 204 (57).

HRMS EI 70 eV: M$_{tr}$=434.2473 for C$_{29}$H$_{30}$N$_4$ M$_{th}$=434.2470.

HPLC: Waters HR C$_{18}$ column, 8×100 mm, 6μ, Waters UV detector 486 to 260 nm, flow rate 3 ml/min, eluent MeOH:H$_2$O=90:10=0.1% TFA, tetrazole (CB56898) tr=4.17 min 99.4%.

EXAMPLE 34

Preparation of (E) and (Z) 5-[2-[1-(5,6,7,8-tetrahydro-5,5,8,8-tetramethyl-2-naphthalenyl)-2-propenyl)]-5-thienyl]-1H-tetrazoles (CB07734 and CB92855)

1) (E) and (Z) 2-[1-(5,6,7,8-tetrahydro-5,5,8,8-tetramethyl-2-naphthalenyl)-2-propenyl)]-5-cyanothiophenes A 1M solution of t-BuOK in THF (14 ml, 14 mmol) is added at −70° C. to a solution of (5,6,7,8-tetrahydro-5,5,8,8-tetramethyl-2-naphthalenyl)-6-methyl-triphenylphosphonium bromide (7.28 g, 13.22 mmol) in 20 ml of anhydrous THF. Agitation is continued at −70° C. for 1 hour before adding 2-acetyl-5-cyanothiophene (1 g, 6.61 mmol) in solution in 10 ml of THE. The reaction medium is brought to ambient temperature and agitated for 14 hours. It is then hydrolysed at 0° C. by a solution of 3N HCl. After returning to ambient temperature, the mixture is extracted with ether, dried over MgSO$_4$, filtered and the solvents evaporated. The raw product is purified by flash chromatography on silica (eluent petroleum ether:ethyl ether=100:1). 0.41 g of a yellow oil is obtained (Z) 2-[1-(5,6,7,8-tetrahydro-5,5,8,8-tetramethyl-2-naphthalenyl)-2-propenyl)]-5-cyanothiophene and 0.39 g of a white powder (E) 2-[1-(5,6,7,8-tetrahydro-5,5,8,8-tetramethyl-2-naphthalenyl)-2-propenyl)]-5-cyanothiophene and 0.70 g of a mixture of the two (Z) and (E) isomers (overall yield=68%).

Isomer (Z)

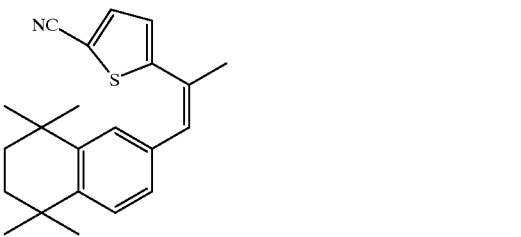

NMR$^1$H 200 MHz (CDCl$_3$) 1.10 and 1.25 (2s, 12H, 5,5,8,8-Me); 1.67 (s, 4H, 6,7-CH$_2$); 2.20 (s, 3H, vinyl Me); 6.65 (s, 1H vinyl H); 6.90 (d, 2H, ArH, J 4 Hz); 7.05 (s, 1H, ArH); 7.22 (d, 2H, ArH, J 8 Hz); 7.40 (d, 1H, ArH, J 4 Hz).

Isomer (E)

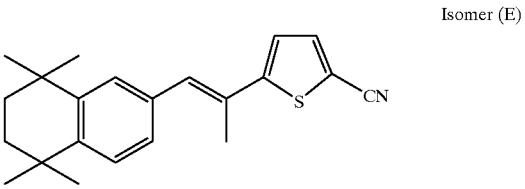

m.pt. (° C.)=108

NMR$^1$H 200 MHz (CDCl$_3$): 1.30 (s, 12H, 5,5,8,8-Me); 1.70 (s, 4H, 6,7-CH$_2$); 2.30 (s, 3H, vinyl Me); 7.02 (s, 1H vinyl H); 7.10–7.20 (m, 2H, ArH); 7.25–7.35 (m, 2H, ArH); 7.55 (d, 1H, ArH, J 4 Hz).

2) (E) 5-[2-[1-(5,6,7,8-tetrahydro-5,5,8,8-tetramethyl-2-naphthalenyl)-2-propenyl)]-5-thienyl]-1H-tetrazole (CB07734)

Dibutyl tin oxide (38.3 mg, 0.14 mmol) and trimethylsilyl azide (0.31 ml, 2.32 mmol), are added successively to a solution of (E) 2-[1-(5,6,7,8-tetrahydro-5,5,8,8-tetramethyl-2-naphthalenyl)-2-propenyl)]-5-cyanothiophene (0.39 g, 1.16 mmol) in anhydrous toluene (2.3 ml). The reaction medium is heated for 14 hours at reflux (110° C.) under an atmosphere of argon and with magnetic stirring. The mixture is purified by flash chromatography on silica (eluent MeOH:$CH_2Cl_2$=10:90) to obtain, after evaporation, 118.8 mg of a white powder (E) 5-[2-[1-(5,6,7,8-tetrahydro-5,5,8,8-tetramethyl-2-naphthalenyl)-2-propenyl)]-5-thienyl]-1H-tetrazole (CB07734) (yield=27%).

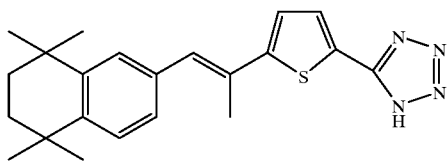

m.pt. (° C.)=186–189

IR ($cm^{-1}$): 3644; 3272; 1594; 1458; 1406.

NMR$^1$H 200 MHz (CDCl$_3$): 1.27 and 1.28 (2s, 12H, 5,5,8,8-Me); 1.67 (s, 4H, 6,7-CH$_2$—); 2.28 (s, 3H, vinyl Me); 7.02 (s, 1H, vinyl H); 7.08–7.15 (m, 2H, ArH); 7.24–7.30 (m, 2H, ArH) 7.74 (d, 1H, ArH, J 4 Hz).

MS EI 70 eV (m/z, % intensity): 378 (M$^+$, 100%); 358 (83); 69 (67).

HRMS EI 70 eV: M$_{tr}$=378.1880 for C$_{22}$H$_{26}$N$_4$S M$_{th}$=378.1878.

HPLC: Waters HR C$_{18}$ column, 8×100 mm, 6μ, Waters UV detector 486 to 260 nm, flow rate 3 ml/min, eluent MeOH:H$_2$O=90:10=0.1% TFA, tetrazole (CB07734) tr=3.49 min 98.9%.

3) (Z) 5-[2-[1-(5,6,7,8-tetrahydro-5,5,8,8-tetramethyl-2-naphthalenyl)-2-propenyl)]-5-thienyl]-1H-tetrazole (CB92855)

Dibutyl tin oxide (39.2 mg, 0.15 mmol) and trimethylsilyl azide (0.325 ml, 2.44 mmol), are added successively to a solution of (Z) 2-[1-(5,6,7,8-tetrahydro-5,5,8,8-tetramethyl-2-naphthalenyl)-2-propenyl)]-5-cyanothiophene (0.41 g, 1.22 mmol) in anhydrous toluene (2.4 ml). The reaction medium is heated for 15 hours at reflux (110° C.) under an atmosphere of argon and with magnetic stirring. The mixture is purified by flash chromatography on silica (eluent MeOH:$CH_2Cl_2$=5:95) followed by preparative HPLC (eluent MeOH:H$_2$O=92:8=0.1% TFA) to obtain, after evaporation, 192.6 mg of a white powder (Z) 5-[2-[1-(5,6,7,8-tetrahydro-5,5,8,8-tetramethyl-2-naphthalenyl)-2-propenyl)]-5-thienyl]-1H-tetrazole (CB92855) (yield 42%).

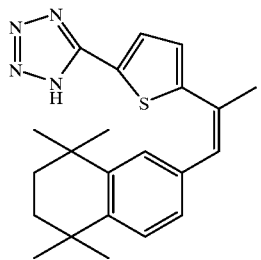

m.pt. (° C.)=126

IR ($cm^{-1}$): 2950; 1552; 1460; 1408; 1362.

NMR$^1$H 200 MHz (CDCl$_3$): 1.07 and 1.20 (2s, 12H, 5,5,8,8-Me); 1.58 (s, 4H, 6,7-CH$_2$—); 2.22 (s, 3H, vinyl Me); 6.56 (s, 1H, vinyl H); 6.88–7.09 (m, 2H, ArH); 7.10–7.16 (m, 2H, ArH) 7.66 (d, 1H, ArH, J 4 Hz).

MS EI 70 eV (m/z, % intensity): 378 (M$^+$, 86%); 350 (74%); 319 (11%); 165 (15%); 69 (100%)

HRMS EI 70 eV: M$_{tr}$=378.1889 for C$_{22}$H$_{26}$N$_4$S M$_{th}$=378.1878.

HPLC: Waters HR C$_{18}$ column, 8×100 mm, 6μ, Waters UV detector 486 to 260 nm, flow rate 3 ml/min, eluent MeOH:H$_2$O=90:10=0.1% TFA, tetrazole (CB07734) tr=2.87 min 98.9%.

EXAMPLE 35

Preparation of (Z) 5-[1-(5,6,7,8-tetrahydro-5,5,8,8-tetramethyl-2-naphthalenyl)-2-propenyl]pyridinyl-2-carboxylic acid (CB16279)

A suspension of (Z) methyl 5-[1-(5,6,7,8-tetrahydro-5,5,8,8-tetramethyl-2-naphthalenyl)-2-propenyl]pyridinyl-2-carboxylate (0.3 g, 0.82 mmol) in solution in methanolic potassium hydroxide (0.46 g, 2.18 mmol KOH, 1.1 ml H$_2$O and 9 ml MeOH) is heated at reflux under magnetic stirring for 3 hours. The methanol is evaporated in a rotary evaporator and the product taken up in water (10 ml), acidified with 3N HCl, extracted with dichloromethane (5×30 ml). The organic phase is dried over MgSO$_4$, filtered and evaporated. The raw product is washed with pentane and then filtered. 0.28 g of a white solid is obtained (Z) 5-[1-(5,6,7,8-tetrahydro-5,5,8,8-tetramethyl-2-naphthalenyl)-2-propenyl]pyridinyl-2-carboxylic acid (CB16279) (yield=98%).

m.pt. (° C.)=62–64

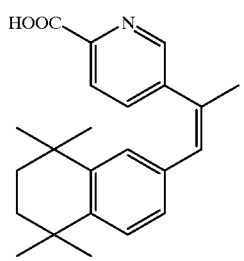

IR ($cm^{-1}$): 3250; 2954; 1898; 1706; 1590.

NMR$^1$H 200 MHz (CDCl$_3$): 0.94 and 1.19 (2s, 12H, 5,5,8,8-Me); 1.56 (s, 4H, 6,7-CH$_2$—); 2.23 (s, 3H, vinyl Me J 1.3 Hz); 6.67 (m, 1H, vinyl H); 6.73 (s, 2H, ArH); 7.09 (d, 1H, ArH J 8 Hz) 7.82 (d, 1H, ArH, J 8 Hz); 8.15 (d, 1H, ArH J 8 Hz); 8.41 (s, 1H, ArH).

MS EI 70 eV (m/z, % intensity): 349 (M⁺, 76%); 334 (100); 316 (5).

HRMS EI 70 eV: $M_{tr}$=349.2059 for $C_{22}H_{27}NO_2$ $M_{th}$=349.2042.

HPLC: Waters HR $C_{18}$ column, 8×100 mm, 6µ, Waters UV detector 486 to 260 nm, flow rate 3 ml/min, eluent MeOH:$H_2O$=90:10=0.1% TFA, acid (CB16279) tr=5.86 min 99.7%.

EXAMPLE 36

Preparation of (E) and (Z) 2-[1-(5,6,7,8-tetrahydro-3,5,5,8,8-pentamethyl-2-naphthalenyl)-2-propenyl] pyridinyl-5-carboxylic acids (CB90525 and CB93634)

1) (E) and (Z) methyl 2-[1-(5,6,7,8-tetrahydro-3,5,5,8,8-pentamethyl-2-naphthalenyl)-2-propenyl]pyridinyl-5-carboxylates A 1M solution of t-BuOK in THF (10 ml, 10 mmol) is added at −70° C. to a solution of (5,6,7,8-tetrahydro-3,5,5,8,8-pentamethyl-2-naphthalenyl)-6-methyl-triphenylphosphonium bromide (5.28 g, 9.48 mmol) in 15 ml of THF. Agitation is continued at −10° C. for 45 minutes before adding methyl 2-acetylpyridine-5-carboxylate (0.85 g, 4.74 mmol) in solution in 7 ml of THF at this temperature. The reaction medium is brought to ambient temperature and agitated for 13 hours. It is then hydrolysed at 0° C. by a solution of 3N HCl (30 ml). After returning to ambient temperature, the mixture is extracted with dichloromethane, dried over $MgSO_4$, filtered and the solvents evaporated. The raw product is purified by flash chromatography on silica (eluent petroleum ether:ethyl ether=100:10 then 100:15). 0.59 g of the (E) and (Z) esters the (E) and (Z) methyl 2-[1-(5,6,7,8-tetrahydro-3,5,5,8,8-pentamethyl-2-naphthalenyl)-2-propenyl]pyridinyl-5-carboxylates are obtained (yield 34%) ((E):(Z)=64:34).

Isomer (Z):

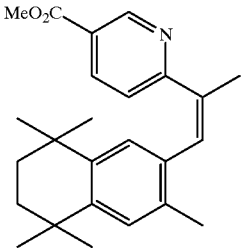

NMR¹H 200 MHz (CDCl₃): 0.60 and 1.15 (2s, 12H, 5,5,8,8-Me); 1.40–1.60 (m, 4H, 6,7-$CH_2$—); 2.25 (s, 3H); 2.32 (s, 3H); 3.95 (s, 3H, MeO—); 6.60 (s, 1H); 6.75 (s, 1H); 7.05 (s, 1H, ArH); 7.62 (m, 1H, ArH); 7.92 (dd, 1H, ArH J 2 Hz and J 8 Hz); 9.15–9.25 (s, 1H, ArH).

Isomer (E)

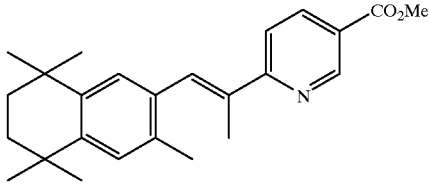

NMR¹H 200 MHz (CDCl₃): 1.30 and 1.32 (2s, 12H, 5,5,8,8-Me); 1.40 (m, 4H, 6,7-$CH_2$—); 2.21 (s, 3H); 2.32 (s, 3H); 3.97 (s, 3H, MeO—); 6.82 (s, 1H); 6.90 (s, 1H); 7.08 (s, 1H, ArH); 7.20 (m, 1H, ArH); 8.02 (dd, 1H, ArH J 2 Hz and J 8 Hz); 9.15–9.25 (s, 1H, ArH).

2) (E) and (Z) 2-[1-(5,6,7,8-tetrahydro-3,5,5,8,8-pentamethyl-2-naphthalenyl)-2-propenyl]pyridinyl-5-carboxylic acids (CB90525 and CB93634)

A suspension of the (E) and (Z) methyl 2-[1-(5,6,7,8-tetrahydro-3,5,5,8,8-pentamethyl-2-naphthalenyl)-2-propenyl]pyridinyl-5-carboxylates ((Z):(E)=64:36), (0.59 g, 1.56 mmol) in solution in methanolic potassium hydroxide (0.87 g, 15.6 mmol KOH, 2 ml $H_2O$ and 17.6 ml MeOH) is heated at reflux under magnetic stirring for 3 hours. The methanol is evaporated in a rotary evaporator and the product taken up in water (10 ml), acidified with 3N HCl, extracted with dichloromethane (5×30 ml). The organic phase is dried over $MgSO_4$, filtered and evaporated. The raw product is purified by preparative HPLC (eluent MeOH:$H_2O$:86:14). 138 mg of a white solid is obtained (Z) 2-[1-(5,6,7,8-tetrahydro-3,5,5,8,8-pentamethyl-2-naphthalenyl)-2-propenyl]pyridinyl-5-carboxylic acid (CB90525) (yield=25%) and 126 mg of a white solid (E) 2-[1-(5,6,7,8-tetrahydro-3,5,5,8,8-pentamethyl-2-naphthalenyl)-2-propenyl]pyridinyl-5-carboxylic acid (CB93634) (yield=22%).

(Z) 2-[1-(5,6,7,8-tetrahydro-3,5,5,8,8-pentamethyl-2-naphthalenyl)-2-propenyl]pyridinyl-5-carboxylic acid (CB90525)

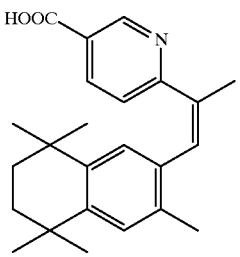

m.pt. (° C.)=85

IR (cm⁻¹): 2956; 2866; 1722; 1898; 1602; 1450; 1390.

NMR¹H 200 MHz (CDCl₃) 0.79 and 1.19 (2s, 12H, 5,5,8,8-Me); 1.23–1.51 (m, 4H, 6,7-$CH_2$—); 2.27 (s, 3H); 2.37 (s, 3H); 6.51 (s, 1H); 6.95 (s, 1H); 7.02 (s, 1H, ArH); 7.16 (s, 1H); 8.30 (d, 1H, ArH J 5 Hz); 9.40 (s, 1H, ArH); 12.7 (s, 1H mobile H).

MS IC negative 200 eV (m/z, % intensity): 363 (M⁺, 67%); 362 (100).

HPLC: Waters HR $C_{18}$ column, 8×100 mm, 6µ, Waters UV detector 486 to 260 nm, flow rate 3 ml/min, eluent MeOH:$H_2O$=85:15=0.1% TFA, acid (CB90525) tr=3.32 min 98.4%.

(E) 2-[1-(5,6,7,8-tetrahydro-3,5,5,8,8-pentamethyl-2-naphthalenyl)-2-propenyl]pyridinyl-5-carboxylic acid (CB93634)

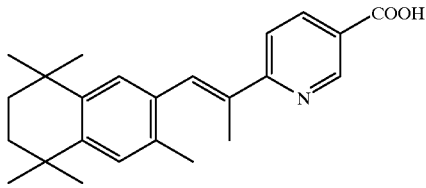

m.pt. (° C.)=157

IR (cm$^{-1}$): 3106; 2956; 2595; 1734; 1644; 1600; 1440; 1392; 1242; 1194; 1142.

NMR$^1$H 200 MHz (CDCl$_3$): 1.27 and 1.29 (2s, 12H, 5,5,8,8-Me); 1.69 (s, 4H, 6,7-CH$_2$—); 2.29 (s, 3H); 2.35 (s, 3H); 7.16 (s, 1H); 7.21 (s, 1H); 7.55 (m, 1H, mobile H); 7.65 (s, 1H); 7.92 (d, 1H, ArH J 8 Hz); 8.73 (d, 1H, J 8 Hz); 9.47 (s, 1H).

MS IC negative 200 eV (m/z, % intensity): 363 (M$^+$, 84%); 362 (100).

HPLC: Waters HR C$_{18}$ column, 8×100 mm, 6µ, Waters UV detector 486 to 260 nm, flow rate 3 ml/min, eluent MeOH:H$_2$O=90:10=0.1% TFA, acid (CB93634) tr=4.72 min 98.1%.

EXAMPLE 37

Preparation of (E) and (Z) 5-[1-(5,6,7,8-tetrahydro-3,5,5,8,8-pentamethyl-2-naphthalenyl)-2-propenyl] pyridinyl-2-carboxylic acids (CB56004) and (CB71329)

1) (E) and (Z) 5-[1-(5,6,7,8-tetrahydro-3,5,5,8,8-pentamethyl-2-naphthalenyl)-2-propenyl]pyridinyl-2-(N,N-diisopropyl)amides A 1M solution of t-BuOK in THF (21 ml, 21 mmol) is added at −70° C. to a solution of (5,6,7,8-tetrahydro-3,5,5,8,8-pentamethyl-2-naphthalenyl)-6-methyl-triphenylphosphonium bromide (11.1 g, 19.9 mmol) in 31 ml of THF. Agitation is continued at −70° C. for 1 hour before adding 5-acetyl-2-(N,N-diisopropyl)amide (2.47 g, 9.94 mmol) at this temperature. The reaction medium is brought to ambient temperature and agitated for 18 hours. It is then hydrolysed at 0° C. by a solution of 3N HCl (25 ml). After returning to ambient temperature, the mixture is extracted with dichloromethane, dried over MgSO$_4$, filtered and the solvents evaporated. The raw product is purified by flash chromatography on silica (eluent petroleum ether:ethyl ether=100:10 and 100:20). 3.59 g of a yellowish gum is obtained (E) and (Z) 5-[1-(5,6,7,8-tetrahydro-3,5,5,8,8-pentamethyl-2-naphthalenyl)-2-propenyl]pyridinyl-2-(N,N-diisopropyl)amides (overall yield 83%) ((E):(Z)=1:2).

Isomer (Z)

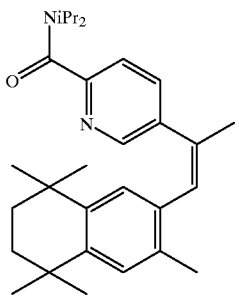

NMR$^1$H 200 MHz (CDCl$_3$): 0.85 (s, 6H); 1.05–1.20 (m, 12H); 1.25 (s, 6H); 1.40–1.60 (m, 4H, 6,7-CH$_2$); 2.20 (s, 3H); 2.25 (s, 3H); 3.35–3.65 (m, 2H); 6.60 (s, 1H); 6.65 (s, 1H); 7.00 (s, 1H); 7.30 (m, 1H); 7.45 (m, 1H); 8.25 (m, 1H).

Isomer (E)

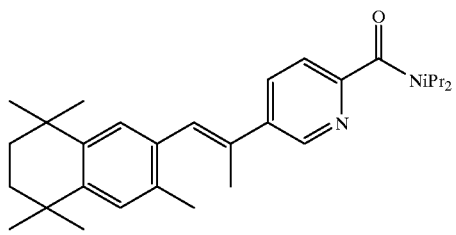

NMR$^1$H 200 MHz (CDCl$_3$) 0.9 (s, 12H, 5,5,8,8-Me); 1.05–1.20 (m, 12H); 1.30 (s, 4H, 6,7-CH$_2$); 2.17 (s, 3H); 2.22 (s, 3H); 3.70–3.95 (m, 2H); 6.92 (m, 1H); 7.10 (m, 1H); 7.20 (m, 1H); 7.50 (m, 1H); 7.80–1.90 (m, 1H); 8.45 (m, 1H).

2) (E) and (Z) 5-[1-(5,6,7,8-tetrahydro-3,5,5,8,8-pentamethyl-2-naphthalenyl)-2-propenyl]-2-formyl pyridines A 1.5 M solution of di-isobutyl aluminium hydride in toluene (15.9 ml, 8.8 mmol) is added at −70° C. to a solution of the (E) and (Z) 5-[1-(5,6,7,8-tetrahydro-3,5,5,8,8-pentamethyl-2-naphthalenyl)-2-propenyl]pyridinyl-2-(N,N-diisopropyl)amides ((E):(Z)=1:2) (2.56 g, 5.86 mmol) in 28 ml of THF. The temperature is allowed to rise to ambient and the mixture is agitated at this temperature for 2 hours. It is cooled to −70° C. and hydrolysed by an aqueous solution of 3N HCl (25 ml). The temperature rises again to ambient and the mixture is extracted with dichloromethane (5×50 ml). The organic phase is dried over MgSO$_4$, filtered and evaporated. The raw product is purified by flash chromatography on silica (eluent petroleum ether:ether 100:10). 0.57 g of a yellow oil is obtained (E) and (Z) 5-[1-(5,6,7,8-tetrahydro-3,5,5,8,8-pentamethyl-2-naphthalenyl)-2-propenyl]-2-formyl pyridines (yield=28%) (E:Z=1:1).

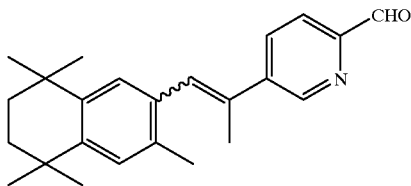

NMR¹H 200 MHz (CDCl₃): 0.76 (s, 0.5×6H); 1.20 (s, 0.5×6H); 1.28 (s, 0.5×12H); 1.40–1.60 (m, 0.5×4H); 1.68 (s, 0.5×4H); 2.15–2.30 (m, 6H); 6.51 (s, 0.5×1H); 6.72 (s, 0.5×1H); 6.95–7.05 (m, 1H) 7.14 (s, 0.5×1H); 7.18 (s, 0.5×1H); 7.55–7.70 (m, 0.5×1H); 7.80 (d, 0.5×1H J 8 Hz); 7.96 (m, 1H); 8.45 (m, 0.5×1H); 9.96 (s, 0.5×1H); 10.08 (s, 0.5×1H).

3) (E) and (Z) methyl 5-[1-(5,6,7,8-tetrahydro-3,5,5,8,8-pentamethyl-2-naphthalenyl)-2-propenyl]pyridinyl-2-carboxylates 0.145 ml of acetic acid, manganese oxide (1.43 g, 16.5 mmol) and sodium cyanide (0.40 g, 8.20 mmol) are successively added at ambient temperature to a solution of the mixture of (E) and (Z) 5-[1-(5,6,7,8-tetrahydro-3,5,5,8,8-pentamethyl-2-naphthalenyl)-2-propenyl]-2-formyl pyridines (0.57 g, 1.64 mmol) in 41 ml of methanol. The reaction medium is agitated at this temperature for 4 hours. It is filtered on paper, evaporated and taken up again in 20 ml of water. This is extracted with ether (5×50 ml), dried over MgSO₄, filtered and evaporated. The raw product is purified by flash chromatography on silica (eluent petroleum ether:ether=70:30). After evaporation 0.11 g of a yellow paste is obtained (Z) methyl 5-[1-(5,6,7,8-tetrahydro-3,5,5,8,8-pentamethyl-2-naphthalenyl)-2-propenyl]pyridinyl-2-carboxylate (yield=18%) and 0.09 g of a white powder (E) methyl 5-[1-(5,6,7,8-tetrahydro-3,5,5,8,8-pentamethyl-2-naphthalenyl)-2-propenyl]pyridinyl-2-carboxylate (yield=14%).

Isomer (Z)

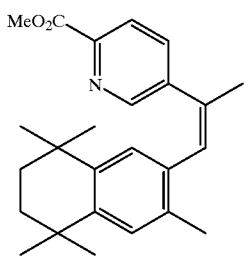

NMR¹H 200 MHz (CDCl₃) 0.78 and 1.18 (s, 6H, 5,5,8,8-Me); 1.40–1.65 (m, 4H, 6,7-CH₂); 2.21 (s, 3H ArMe); 2.24 (s, 3H, vinyl Me); 3.94 (s, 3H, —OMe); 6.52 (s, 1H); 6.67 (s, 1H); 6.98 (s, 1H, ArH); 7.55–7.59 (m, 1H, ArH); 7.94 (d, 1H, ArH, J 7 Hz); 8.38 (m, 1H, ArH).

Isomer (E)

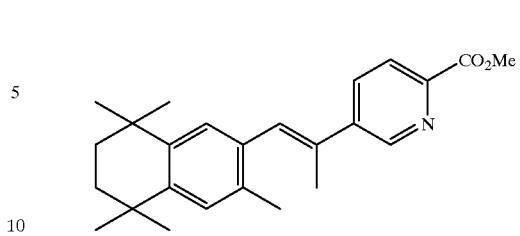

m.pt. (° C.)=132

NMR¹H 200 MHz (CDCl₃) 1.27 (s, 12H, 5,5,8,8-Me); 1.68 (m, 4H, 6,7-CH₂); 2.20 (s, 3H vinyl Me); 2.23 (s, 3H, ArMe); 4.00 (s, 3H, —OMe); 6.94 (s, 1H); 7.12 (s, 1H); (m, 2H, ArH); 7.18 (s, 1H); 7.89–7.94 (m, 1H, ArH); 8.11 (d, 1H, ArH, J 8 Hz); 8.89 (m, 1H, ArH).

4) (Z) 5-[1-(5,6,7,8-tetrahydro-3,5,5,8,8-pentamethyl-2-naphthalenyl)-2-propenyl]pyridinyl-2-carboxylic acid (CB56004)

A suspension of (Z) methyl 5-[1-(5,6,7,8-tetrahydro-3,5,5,8,8-pentamethyl-2-naphthalenyl)-2 -propenyl]pyridinyl-2-carboxylate (110 mg, 0.29 mmol) in solution in methanolic potassium hydroxide (160 mg, 2.90 mmol KOH, 0.3 ml H₂O and 3.1 ml MeOH) is heated at reflux under magnetic stirring for 6 hours. The methanol is evaporated in a rotary evaporator and the product taken up in water (10 ml), acidified with 3N HCl, extracted with dichloromethane (3×20 ml). The organic phase is dried over MgSO₄, filtered and evaporated. The raw product is washed with pentane and then filtered. 80 mg of a solid is obtained (Z) 5-[1-(5,6,7,8-tetrahydro-3,5,5,8,8-pentamethyl-2-naphthalenyl)-2-propenyl]pyridinyl-2-carboxylic acid (CB56004) (yield=76%).

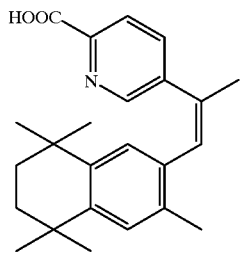

m.pt. (° C.)=66

IR (cm⁻¹) 3250; 2924; 1706; 1590; 1446; 1282; 1240; 1150; 1030.

NMR¹H 200 MHz (CDCl₃): 0.75 and 1.20 (2s, 12H, 5,5,8,8-Me); 1.23 (s, 3H, vinyl Me); 1.50–1.56 (m, 4H, 6,7-CH₂—); 2.26 (s, 3H, ArMe); 6.48 (s, 1H); 6.73 (s, 1H); 7.03 (s, 1H); 7.96 (dd, 1H, ArH J 1.7 Hz J 8 Hz); 8.05 (d, 1H, ArH J 8 Hz); 8.24 (s, 1H, ArH).

MS EI 70 eV (m/z, % intensity): 363 (M⁺, 70%); 348 (100); 330 (35).

HRMS EI 70 eV: $M_{tr}$=363.2201 for $C_{24}H_{29}NO_2$ $M_{th}$=363.2198.

HPLC: Waters HR $C_{18}$ column, 8×100 mm, 6μ, Waters UV detector 486 to 260 nm, flow rate 3 ml/min, eluent MeOH:H₂O=85:15=0.1% TFA, acid (CB56004) tr=3.22 min 97.3%.

5) (E) 5-[1-(5,6,7,8-tetrahydro-3,5,5,8,8-pentamethyl-2-naphthalenyl)-2-propenyl]pyridinyl-2-carboxylic acid (CB71329)

A suspension of (E) methyl 5-[1-(5,6,7,8-tetrahydro-3,5,5,8,8-pentamethyl-2-naphthalenyl)-2-propenyl]pyridinyl-2-carboxylate (90 mg, 0.23 mmol) in solution in methanolic potassium hydroxide (130 mg, 2.30 mmol KOH, 0.25 ml $H_2O$ and 2.5 ml MeOH) is heated at reflux under magnetic stirring for 2 hours. The methanol is evaporated in a rotary evaporator and the product taken up in water (10 ml), acidified with 3N HCl, extracted with dichloromethane (3×20 ml). The organic phase is dried over $MgSO_4$, filtered and evaporated. The raw product is washed with pentane and then filtered. 80 mg of a white solid is obtained (E) 5-[1-(5,6,7,8-tetrahydro-3,5,5,8,8-pentamethyl-2-naphthalenyl)-2-propenyl]pyridinyl-2-carboxylic acid (CB71329) (yield=95%).

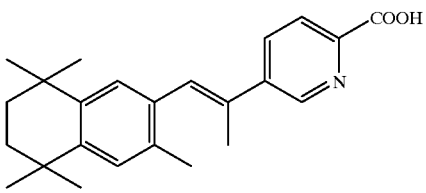

m.pt. (° C.)=172

IR ($cm^{-1}$) 3406; 2924; 2458; 1894; 1710; 1584; 1452; 1320; 1128; 1132.

NMR$^1$H 200 MHz ($CDCl_3$): 1.21 (s, 12H, 5,5,8,8-Me); 1.68 (s, 4H, 6,7-$CH_2$—); 2.21 (s, 3H); 2.24 (s, 3H); 6.98 (s, 1H, vinyl H); 7.13 (s, 1H, ArH); 7.17 (s, 1H); 8.03 (d, 1H, ArH J 8 Hz); 8.21 (d, 1H, ArH J 8 Hz); 8.17 (m, 1H, ArH).

MS EI 70 eV (m/z, % intensity): 363 ($M^+$, 75%); 348 (100); 330 (44); 304 (33).

HRMS EI 70 eV: $M_{tr}$=363.2195 for $C_{24}H_{29}NO_2$ $M_{th}$= 363.2198.

HPLC: Waters HR $C_{18}$ column, 8×100 mm, 6μ, Waters UV detector 486 to 260 nm, flow rate 3 ml/min, eluent MeOH:$H_2O$ 85:15=0.1% TFA, acid (CB71329) tr=4.67 min 97.8%.

What is claimed is:

1. A polycyclic aromatic compound of the retinoid type of general formula:

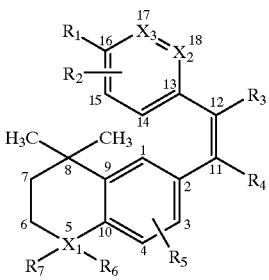

(I)

in which the groups $R_3$ and $R_4$ carried by the double bond between the 11 and 12 carbon are in a cis arrangement and $R_1$, $R_2$, $R_3$, $R_4$, $R_5$, $R_6$, $R_7$, $X_1$ $X_2$ and $X_3$ have the following meanings:

$R_1$ represents a tetrazoyl group, —$CH_2OH$, —CHO, —COOH, —$COR_8$, —$CH_2OCOR_9$, —SH, —S— alkyl, —$PO_3H_2$, p-hydroxyphenylaminocarbonyl, tetrazol-5-ylaminocarbonyl, tetrazol-5-yl, 5-trifluoromethyl-tetrazoyl, and a physiologically acceptable salt thereof, where $R_8$ and $R_9$ are:

a hydrogen atom, an —OH group, a $C_1$-$C_6$ alkyl group, or a group of formula —$OR_{10}$, where $R_{10}$ represents an alkyl group, which may be branched or not, having from 1 to 20 carbon atoms, an alkenyl group which may be branched or not, having from 2 to 20 carbon atoms, an aryl or aralkyl group, or an amine group of formula:

in which r and r', identical or different, represent a hydrogen atom, a $C_1$-$C_6$ alkyl group, an aryl or aralkyl group, an a-aminoacid group, a sugar group or a heterocyclic group in which r and r' taken together form a heterocyclic ring, $R_2$ represents a hydrogen atom, a halogen atom, a $C_1$-$C_6$ alkyl group, a group of formula —COOH, —$OR_{11}$, —$SR_{11}$, —$(CF_2)_nCF_3$ where n is a whole number between 0 and 10, or a —$OCOR_{11}$ group, and a physiologically acceptable salt thereof, or an amine group of formula:

in which r and r' have the same meaning as above, and $R_{11}$ represents a hydrogen atom, a $C_1$-$C_6$ alkyl group, a fluoroalkyl group having 1 to 6 carbon atoms and from 3 to 7 fluorine atoms, an aryl group or an aralkyl group;

$R_3$ represents a hydrogen atom, a trifluoromethyl group, an aryl group, an aralkyl group or a $C_1$-$C_6$ alkyl group, unsubstituted or substituted with a hydroxyl group or with one or more atoms of fluorine, with a $C_1$-$C_6$ alkoxy group or with a group of formula —(C=O)$R_{12}$, in which $R_{12}$ represents a hydrogen atom, a $C_1$-$C_6$ alkyl group, a hydroxyl group, a $C_1$-$C_6$ alkoxy group, or an amine group of formula:

in which r and r' have the same meaning as above, $R_4$ represents a hydrogen atom or an aryl group, $R_5$ represents a hydrogen atom, a $C_1$-$C_6$ alkyl group, a halogen atom, a fluoroalkyl group having 1 to 6 carbon atoms and from 3 to 7 atoms of fluorine, or a group of formula —$OR_{13}$ where $R_{13}$ represents a hydrogen atom, a $C_1$-$C_6$ alkyl group, an aryl group or an aralkyl group or a trifluoromethyl group, $X_1$ is carbon, and $R_6$ and $R_7$ are independently methyl or ethyl groups, $X_2$ and $X_3$, each represent carbon.

2. The compound according to claim 1, wherein in Formula (I), $R_4$ represents a hydrogen atom.

3. The compound according to claim 1, wherein in Formula (I), $R_3$ represents a $C_1$-$C_6$ alkyl group or a trifluoromethyl group or a —$(CH_2)_nCF_3$ group where n is a whole number between 0 and 10.

4. The compound according to claim 1, wherein in Formula (I), $R_2$ represents a hydrogen atom and $R_1$ represents a tetrazoyl group or a —COOH group.

5. A therapeutic, dermatological or cosmetic composition including at least one compound of Formula (I) defined in claim 1, in a free form or in the form of a pharmaceutically acceptable salt, in association with a physiologically acceptable vehicle or diluent.

6. A method for the manufacture of a therapeutic composition useful in for the treatment of cancers comprising the step of admixing a compound of claim 1 with a pharmaceutically acceptable carrier.

7. A method for the manufacture of a therapeutic composition for in the treatment of non-insulin dependent diabetes comprising the step of admixing a compound of claim 1 with a pharmaceutically acceptable carrier.

8. A method for the manufacture of a therapeutic composition for the treatment of inflammatory diseases comprising the step of admixing a compound of claim 1 with a pharmaceutically acceptable carrier.

9. A method for the manufacture of a therapeutic composition for the treatment of immunitary diseases comprising the step of admixing a compound of claim 1 with a pharmaceutically acceptable carrier.

10. A method for the manufacture of a therapeutic composition for the treatment of diseases of the skin comprising the step of admixing compound of claim 1 with a pharmaceutically acceptable carrier.

11. The compound according claim 1, wherein said compound is selected from the group consisting of:

cis 2-(1-(5,6,7,8-tetrahydro-5,5,8,8-tetramethyl-2-naphthalenyl)-2-propenyl)pyridinyl-5-carboxylic acid, trans 4-(1-trifluoromethyl-2-(5,6,7,8-tetrahydro-5,5,8,8-tetramethyl-2-naphthalenyl)-1-ethenyl)benzoic acid, cis 4-(1-(5,6,7,8-tetrahydro-3,5,5,8,8-pentamethyl-2-naphthalenyl)-2-propenyl)benzoic acid, trans 4-(1-trifluoromethyl-2-(5,6,7,8-tetrahydro-3,5,5,8,8-pentamethyl-2-naphthalenyl)-1-ethenyl)benzoic acid, cis 4-(1-(3',4'-dihydro-4',4'-dimethyl-1',1'-dioxide-2'H-1'-benzothiopyran-6'-yl)-2-propenyl)benzoic acid, cis 5-(4-(1-(5,6,7,8-tetrahydro-5,5,8,8-tetramethyl-2-naphthalenyl)-2-propenyl)phenyl)-1H-tetrazole, trans 5-(4-(1-trifluoromethyl-2-(5,6,7,8-tetrahydro-5,5,8,8-tetramethyl-2-naphthalenyl)-1-ethenyl)phenyl)-1H-tetrazole, cis 5-(4-(1-(5,6,7,8-tetrahydro-3,5,5,8,8-pentamethyl-2-naphthalenyl)-2-propenyl)phenyl)-1H-tetrazole, trans 5-(4-(1-trifluoromethyl-2-(5,6,7,8-tetrahydro-3,5,5,8,8-pentamethyl-2-naphthalenyl)-1-ethenyl)phenyl)-1H-tetrazole, cis 5-(4-(1-(3',4'-dihydro-4',4'-dimethyl-1',1'-dioxide-2'H-1'-benzothiopyran-6'-yl)-2-propenyl)phenyl)-1H-tetrazole cis 2-(1-(5,6,7,8-tetrahydro-5,5,8,8-tetramethyl-2-naphthalenyl)-2-propenyl)thienyl-5-carboxylic acid, cis 5-(2-(1-(5,6,7,8-tetrahydro-5,5,8,8-tetramethyl-2-naphthalenyl)-2-propenyl))5-thienyl-1H-tetrazole, cis 5-(1-(5,6,7,8-tetrahydro-5,5,8,8-tetramethyl-2-naphthalenyl)-2-propenyl)pyridinyl-2-carboxylic acid, cis 2-(1-(5,6,7,8-tetrahydro-3,5,5,8,8-pentamethyl-2-naphthalenyl)-2-propenyl)pyridinyl-5-carboxylic acid, cis 5-(1-(5,6,7,8-tetrahydro-3,5,5,8,8-pentamethyl-2-naphthalenyl)-2-propenyl)pyridinyl-2-carboxylic acid, cis 5-(1-(5,6,7,8-tetrahydro-5,5,8,8tetramethyl-2-naphthalenyl)-2-propenyl)isoxazole-3-carboxylic acid, cis 5-(1-(5,6,7,8-tetrahydro-3,5,5,8,8-pentamethyl-2-naphthalenyl)-2-propenyl)isoxazole-3-carboxylic acid, and cis 1-(4-(1-(5,6,7,8-tetrahydro-5,5,8,8-tetramethyl-2-naphthalenyl)-2-propenyl)phenyl)-5-trifluoromethyl-1H-tetrazole.

12. A polycyclic aromatic compound of the retinoid type of general formula (I):

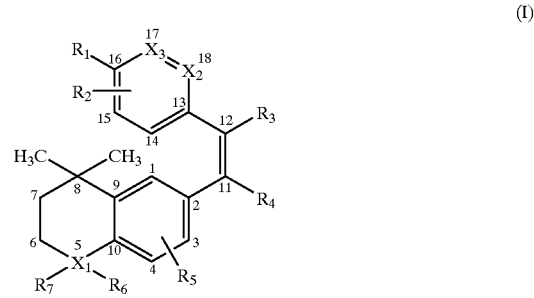

in which the groups $R_3$ and $R_4$ carried by the double bond between the 11 and 12 carbon are in a cis arrangement and wherein:

$R_1$ represents a tetrazoyl group or a —COOH radical, and a physiologically acceptable salt thereof, $R_2$ represents a hydrogen atom, a halogen atom, a $C_1$ to $C_6$ alkyl group, a group of formula —COOH, —$OR_{11}$, —$SR_{11}$, —$(CF_2)_n CF_3$ where n is a whole number between 0 and 10, or a —$OCOR_{11}$ group, and a physiologically acceptable salt thereof, or an amine group of formula:

in which r and r', identical or different, represent a hydrogen atom, a $C_1$ to $C_6$ alkyl group, an aryl or aralkyl group, an α-aminoacid group, a sugar group or a heterocyclic group in which r and r' taken together form a heterocyclic ring, and $R_{11}$ represents a hydrogen atom, a $C_1$ to $C_6$ alkyl group, a fluoroalkyl group having 1 to 6 carbon atoms and from 3 to 7 fluorine atoms, an aryl group or an aralkyl group;

$R_3$ represents a hydrogen atom, a trifluoromethyl group, an aryl group, an aralkyl group or a $C_1$ to $C_6$ alkyl group, unsubstituted or substituted with a hydroxyl group or with one or more atoms of fluorine, with a $C_1$ to $C_6$ alkoxy group or with a group of formula —(C═O)$R_{12}$, in which $R_{12}$ represents a hydrogen atom, a $C_1$ to $C_6$ alkyl group, a hydroxyl group, a $C_1$ to $C_6$ alkoxy group, or an amine group of formula:

in which r and r' have the same meaning as above, $R_4$ represents a hydrogen atom or an aryl group, $R_5$ represents a hydrogen atom, a $C_1$ to $C_6$ alkyl group, a halogen atom, a fluoroalkyl group having 1 to 6 carbon atoms and from 3 to 7 atoms of fluorine, or a group of formula —$OR_{13}$ where $R_{13}$ represents a hydrogen atom, a $C_1$ to $C_6$ alkyl group, an aryl group or an aralkyl group or a trifluoromethyl group, $X_1$ is an atom of carbon and $R_6$ and $R_7$ are, independently, methyl or ethyl groups; and $X_2$ and $X_3$ each represent carbon.

13. A method for treating cancer comprising administering an effective amount of a compound of claim 1.

14. A method for treating non-insulin diabetes comprising administering an effective amount of a compound of claim 1.

15. A method for treating inflammatory diseases comprising administering an effective amount of a compound of claim 1.

16. A method for treating immunitary diseases comprising administering an effective amount of a compound of claim 1.

17. A method for treating diseases of the skin comprising administering an effective amount of a compound of claim 1.

* * * * *